US010500361B2

(12) United States Patent
Phillips et al.

(10) Patent No.: US 10,500,361 B2
(45) Date of Patent: Dec. 10, 2019

(54) ENDOTRACHEAL TUBE RETENTION SYSTEM

(71) Applicant: Applied Medical Technology, Inc., Brecksville, OH (US)

(72) Inventors: Grant W. Phillips, Richfield, OH (US); Kathleen Walsh, Tallmadge, OH (US); Elizabeth A Meyer, Copley, OH (US); Derek M. Williams, Cuyahoga Falls, OH (US); George J. Picha, Brecksville, OH (US)

(73) Assignee: APPLIED MEDICAL TECHNOLOGY, INC., Brecksville, OH (US)

(*) Notice: Subject to any disclaimer, the term of this patent is extended or adjusted under 35 U.S.C. 154(b) by 769 days.

(21) Appl. No.: 15/255,984

(22) Filed: Sep. 2, 2016

(65) Prior Publication Data

US 2016/0367777 A1 Dec. 22, 2016

Related U.S. Application Data

(63) Continuation of application No. 14/216,257, filed on Mar. 17, 2014, now abandoned.

(60) Provisional application No. 61/791,663, filed on Mar. 15, 2013.

(51) Int. Cl.
*A61M 16/04* (2006.01)
*A61M 16/06* (2006.01)
*A61M 25/02* (2006.01)

(52) U.S. Cl.
CPC .... *A61M 16/0497* (2013.01); *A61M 16/0488* (2013.01); *A61M 16/0493* (2014.02); *A61M 16/0683* (2013.01); *A61M 2025/022* (2013.01); *A61M 2209/088* (2013.01); *A61M 2210/0618* (2013.01)

(58) Field of Classification Search
CPC .... A61M 2210/0618; A61M 2209/088; A61M 16/0683; A61M 16/0497; A61M 16/0493; A61M 16/0488; A61M 2025/022
See application file for complete search history.

(56) References Cited

U.S. PATENT DOCUMENTS

| 3,568,678 A | 3/1971 | Pourquier et al. |
| 3,927,676 A | 12/1975 | Schultz |
| 3,946,742 A | 3/1976 | Eross |

(Continued)

FOREIGN PATENT DOCUMENTS

| WO | 02/20082 A1 | 3/2002 |
| WO | 2011/159997 A1 | 12/2011 |

OTHER PUBLICATIONS

Dominguez, E., "Carbon Dioxide Monitoring during Deep Conscious Sedation . . . ," Anesthesiology 1999, vol. 91, No. 4, pp. 1177-1178, Oct. 1999.

(Continued)

*Primary Examiner* — Colin W Stuart
*Assistant Examiner* — Douglas Y Sul
(74) *Attorney, Agent, or Firm* — Pearne & Gordon, LLP

(57) ABSTRACT

A retention system for use with a bridle installed in a nose of a patient includes a member coupled to a medical device that is suspended from a nose of a patient and a connector for coupling to a bridle that is installed in a nose of a patient. The medical device extends into the mouth of a patient or is suspended adjacent the face of a patient.

20 Claims, 34 Drawing Sheets

(56) References Cited

U.S. PATENT DOCUMENTS

| | | |
|---|---|---|
| 3,972,321 A | 8/1976 | Proctor |
| 3,976,080 A | 8/1976 | Bronhorst et al. |
| 3,993,081 A | 11/1976 | Cussell |
| 4,142,527 A | 3/1979 | Garcia |
| 4,270,529 A | 6/1981 | Muto |
| 4,331,143 A | 5/1982 | Foster |
| 4,351,331 A | 9/1982 | Gereg |
| 4,378,012 A | 3/1983 | Brown |
| 4,392,857 A | 7/1983 | Beran |
| 4,449,527 A | 5/1984 | Hinton |
| 4,520,813 A | 6/1985 | Young |
| 4,530,354 A | 7/1985 | Froilan |
| 4,537,192 A | 8/1985 | Foster |
| 4,548,200 A | 10/1985 | Wapner |
| 4,658,814 A | 4/1987 | Anderson |
| 4,683,882 A | 8/1987 | Laird |
| 4,744,358 A | 5/1988 | McGinnis |
| 4,774,944 A | 10/1988 | Mischinski |
| 4,832,019 A | 5/1989 | Weinstein et al. |
| 4,906,234 A | 3/1990 | Voychehovski |
| 5,009,227 A | 4/1991 | Nieuwstad |
| 5,038,778 A | 8/1991 | Lott |
| 5,042,477 A | 8/1991 | Lewis |
| 5,069,206 A | 12/1991 | Crosbie |
| 5,076,269 A * | 12/1991 | Austin .............. A61M 16/0488 128/207.14 |
| 5,123,410 A | 6/1992 | Greene et al. |
| 5,146,913 A | 9/1992 | Khorsandian et al. |
| 5,185,005 A | 2/1993 | Ballantyne |
| 5,295,480 A | 3/1994 | Zemo |
| 5,305,742 A | 4/1994 | Styers et al. |
| 5,306,233 A | 4/1994 | Glover |
| 5,320,094 A | 6/1994 | Laube et al. |
| 5,320,097 A | 6/1994 | Clemens et al. |
| 5,345,931 A | 9/1994 | Battaglia, Jr. |
| 5,368,024 A | 11/1994 | Jones |
| 5,383,451 A | 1/1995 | Delulio |
| 5,398,679 A | 3/1995 | Freed |
| 5,402,776 A | 4/1995 | Islava |
| 5,411,484 A | 5/1995 | Shattuck |
| 5,437,273 A | 8/1995 | Bates et al. |
| 5,448,985 A | 9/1995 | Byrd |
| 5,490,504 A | 2/1996 | Vrona et al. |
| 5,513,633 A | 5/1996 | Islava |
| 5,555,881 A | 9/1996 | Rogers et al. |
| 5,558,090 A | 9/1996 | James |
| 5,626,565 A | 5/1997 | Landis et al. |
| 5,638,814 A | 6/1997 | Byrd |
| 5,653,228 A | 8/1997 | Byrd |
| 5,653,232 A | 8/1997 | Rogers et al. |
| 5,803,079 A | 9/1998 | Rogers et al. |
| 5,806,516 A | 9/1998 | Beattie |
| 5,829,430 A | 11/1998 | Islava |
| 5,868,132 A | 2/1999 | Winthrop et al. |
| 5,894,640 A | 4/1999 | Dewey |
| 5,894,840 A | 4/1999 | King |
| 5,934,276 A | 8/1999 | Fabro et al. |
| 5,937,858 A | 8/1999 | Connell |
| 5,941,246 A | 8/1999 | Roopchand |
| 5,996,581 A | 12/1999 | Duch |
| 6,050,263 A | 4/2000 | Choksi et al. |
| 6,067,985 A | 5/2000 | Islava |
| D434,496 S | 11/2000 | Choksi et al. |
| 6,159,158 A | 12/2000 | Lowe |
| 6,336,457 B1 | 1/2002 | Hudson et al. |
| 6,408,850 B1 | 6/2002 | Sudge |
| 6,464,668 B1 | 10/2002 | Pace |
| 6,488,664 B1 | 12/2002 | Solomon et al. |
| 6,526,978 B2 | 3/2003 | Dominguez |
| 6,561,192 B2 | 5/2003 | Palmer |
| 6,631,715 B2 | 10/2003 | Kim |
| 6,675,808 B2 | 1/2004 | Karasic |
| 6,810,878 B2 | 11/2004 | Palmer |
| 6,837,237 B2 | 1/2005 | Kim |
| 7,017,579 B2 | 3/2006 | Palmer |
| 7,063,088 B1 | 6/2006 | Christopher |
| 7,534,228 B2 | 5/2009 | Williams |
| 8,001,969 B2 | 8/2011 | Kanowitz |
| 8,056,562 B2 | 11/2011 | Sherman |
| 8,096,300 B2 | 1/2012 | Russo |
| 8,256,427 B2 | 9/2012 | Chang et al. |
| 2002/0026936 A1 | 3/2002 | Kim |
| 2004/0069309 A1 | 4/2004 | Kim |
| 2004/0231675 A1 | 11/2004 | Lyons |
| 2005/0092328 A1* | 5/2005 | Herrick .............. A61M 16/0488 128/207.17 |
| 2005/0133038 A1 | 6/2005 | Rutter |
| 2005/0236001 A1 | 10/2005 | Williams |
| 2006/0118119 A1 | 6/2006 | Berthon-Jones et al. |
| 2008/0006275 A1 | 1/2008 | Nickelson et al. |
| 2008/0142019 A1 | 6/2008 | Lewis et al. |
| 2008/0202529 A1 | 8/2008 | Flory et al. |
| 2009/0211573 A1 | 8/2009 | Russo |
| 2009/0255538 A1 | 10/2009 | Thomson et al. |
| 2010/0180900 A1 | 7/2010 | Talsma et al. |
| 2010/0252049 A1 | 10/2010 | Kost |
| 2011/0108038 A1 | 5/2011 | Pierson |
| 2011/0126839 A1 | 6/2011 | Levine |
| 2011/0180065 A1 | 7/2011 | Hajgato et al. |
| 2011/0240034 A1 | 10/2011 | Ciccone |
| 2012/0085348 A1 | 4/2012 | Chalvignac et al. |
| 2012/0168571 A1* | 7/2012 | Bond ................ A61M 16/0488 248/70 |
| 2012/0227747 A1 | 9/2012 | Levine |
| 2013/0087152 A1* | 4/2013 | Kirn ................ A61M 16/0488 128/207.14 |

OTHER PUBLICATIONS

Dominguez, E., "Another Use for Nasopharyngeal Airway," Anesthesiology 2000, vol. 93, No. 1, pp. 298-299, Jul. 2000.

Lee, Christopher R., "Who Nose Where the Airway Is?", Agency for Healthcare Research and Quality (AH RQ) WebM&M, Cases & Commentary, Oct. 2009. http://www.webmm.ahrq.gov.

Kotler, R., et al., "Introducing . . . The Kotler Nasal Airway™", The Kotler Nasal Airway Official Website, "A Strategy and New Device to Ensure Patient Safety . . . ," copyright 2011 . www.kotlernasalairway.com.

Rhino Rocket® with Applicator, Shippert Medical Technologies Incorporated on-line catalog, vol. IX, p. 11, copyright 2013. www.shippertmedical.com.

Rapid Rino® 900, ArthroCare Corporation, on-line Technique Guide, 2 pgs., copyright 2009. www.arthrocareENT.com.

AMT Bridle Nasal Tube Retaining System brochure, 4 pgs., Applied Medical Technology, Inc., copyright 2010. www.appliedmedical.net.

International Search Report for PCT Application No. PCT/US2014/030499; dated Aug. 7, 2014.

\* cited by examiner

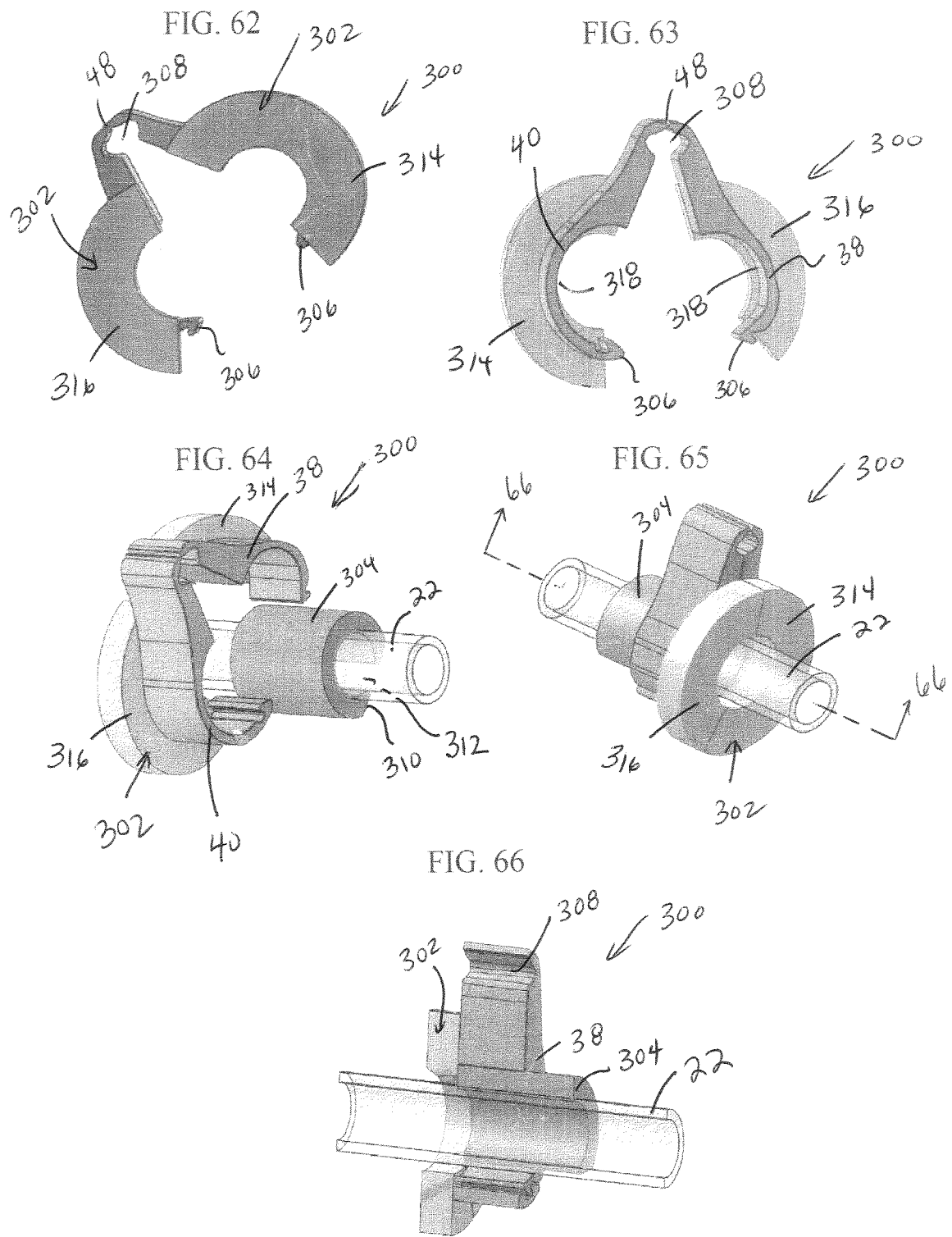

SECTION 68-68

SECTION 77-77

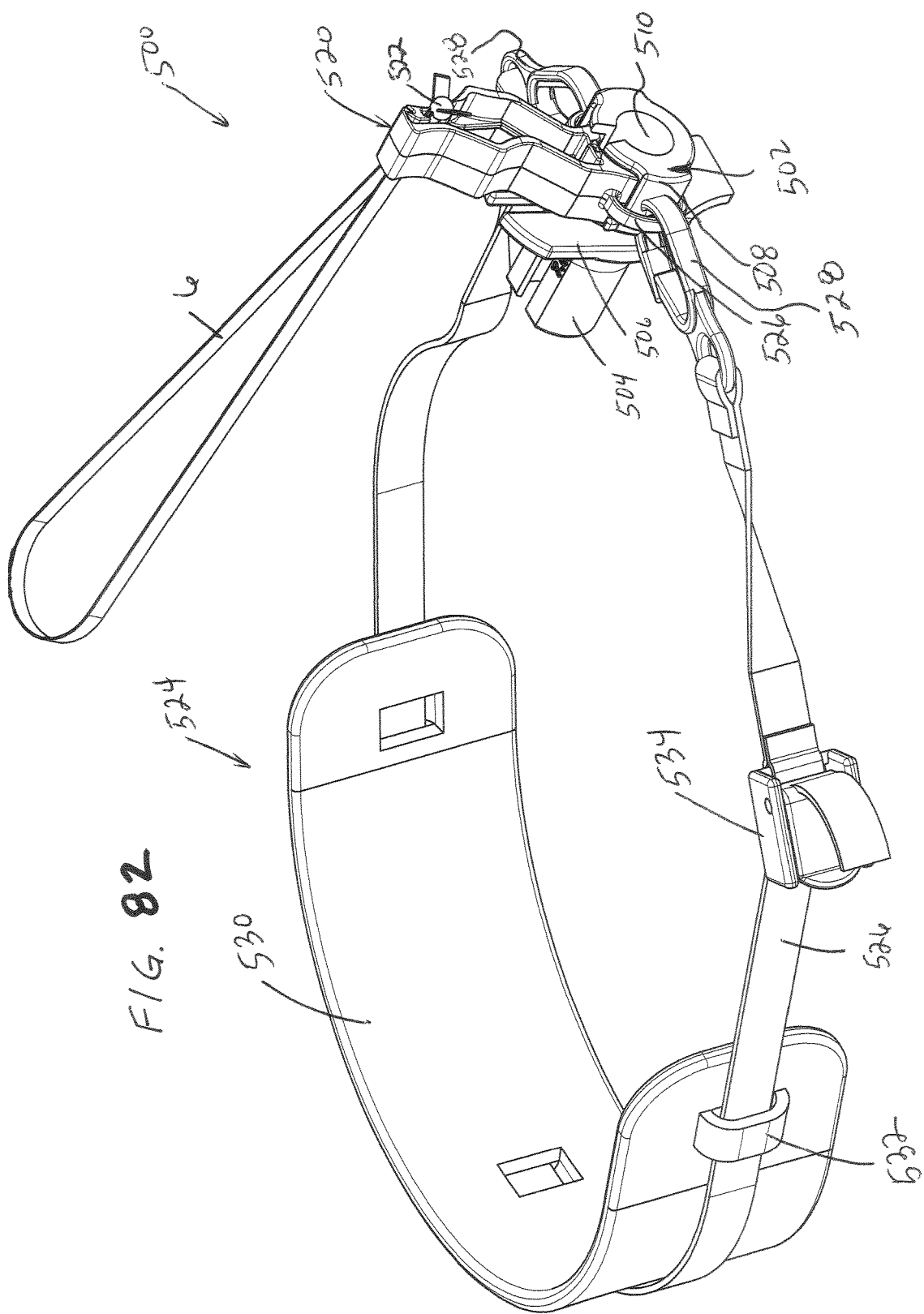

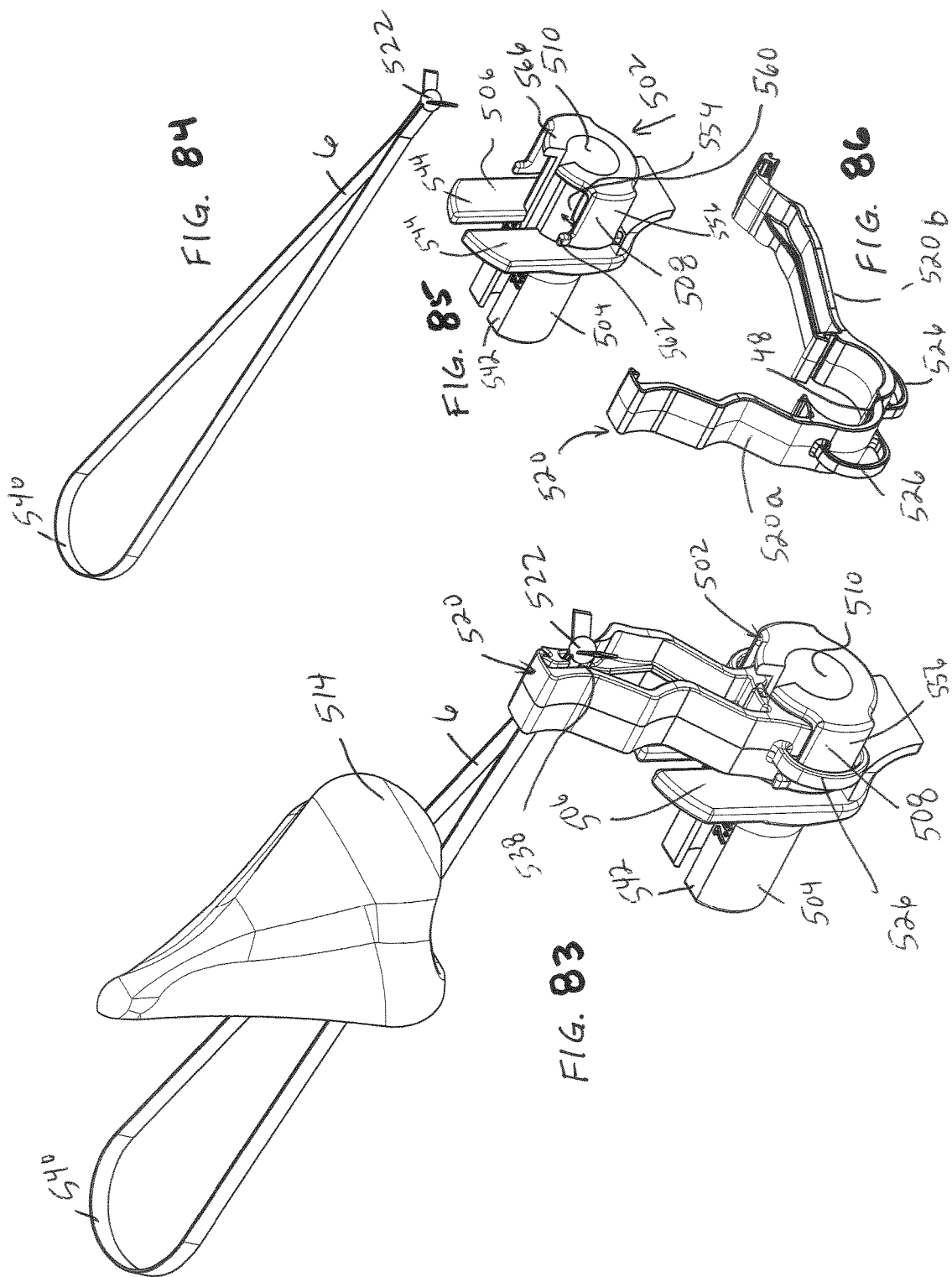

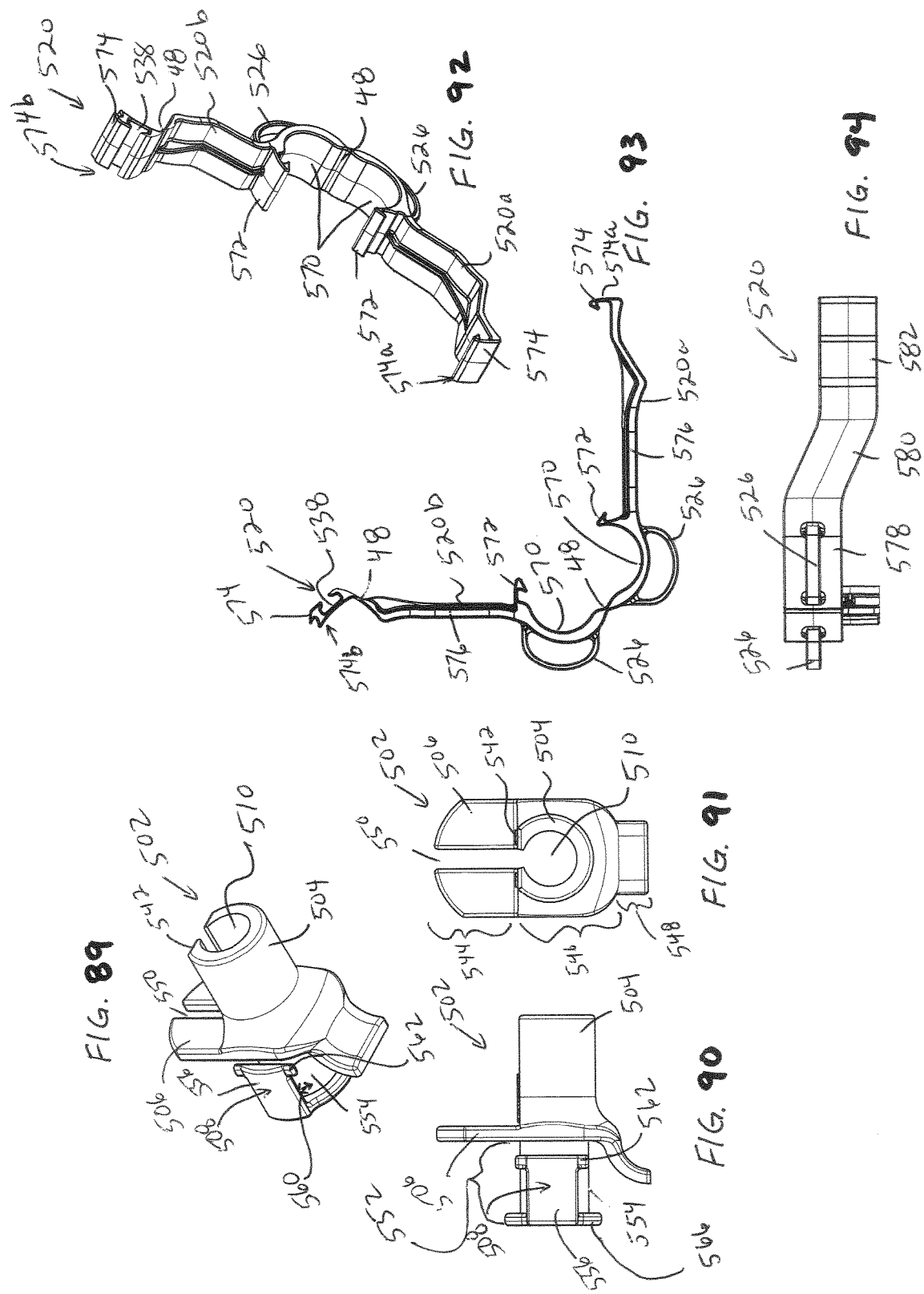

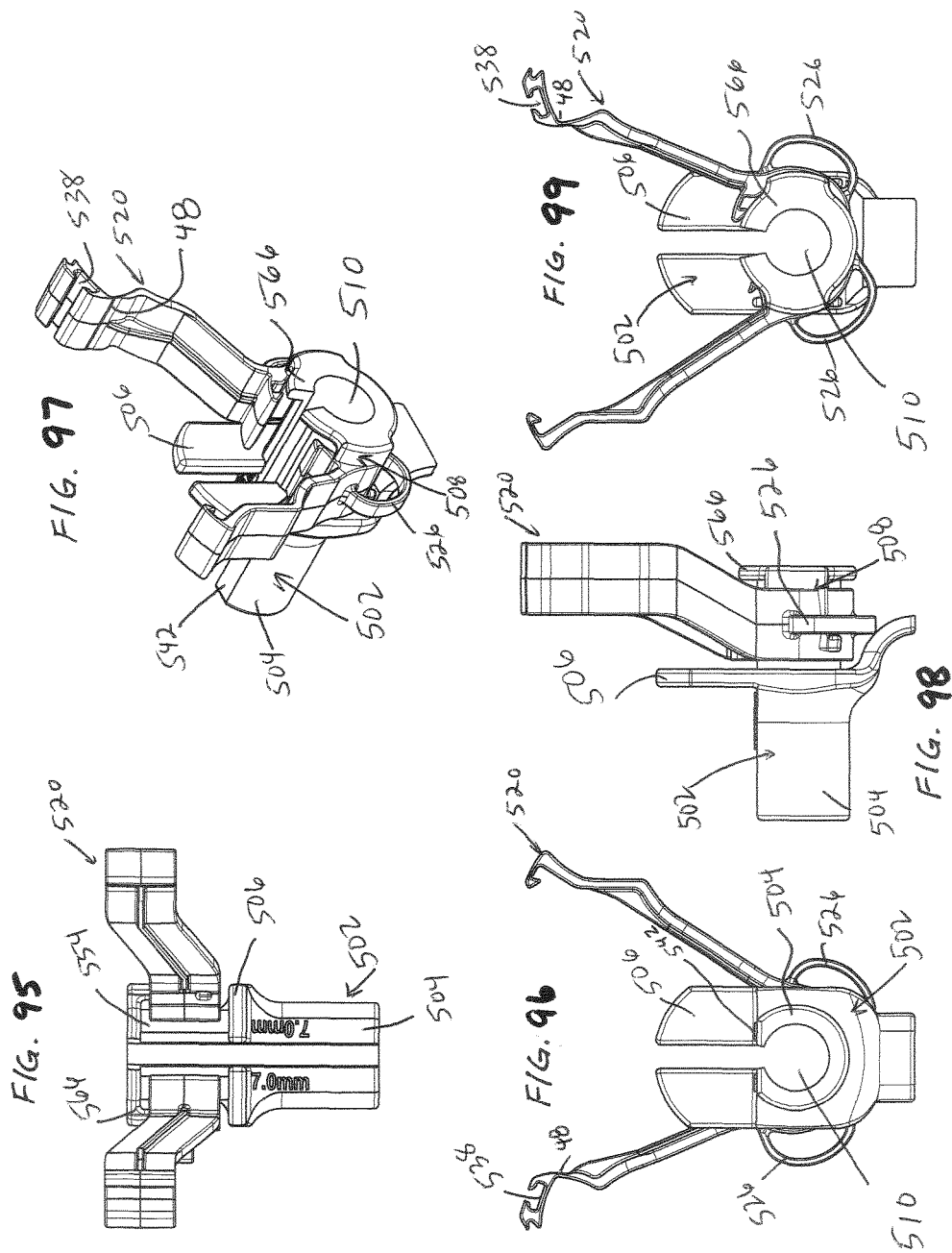

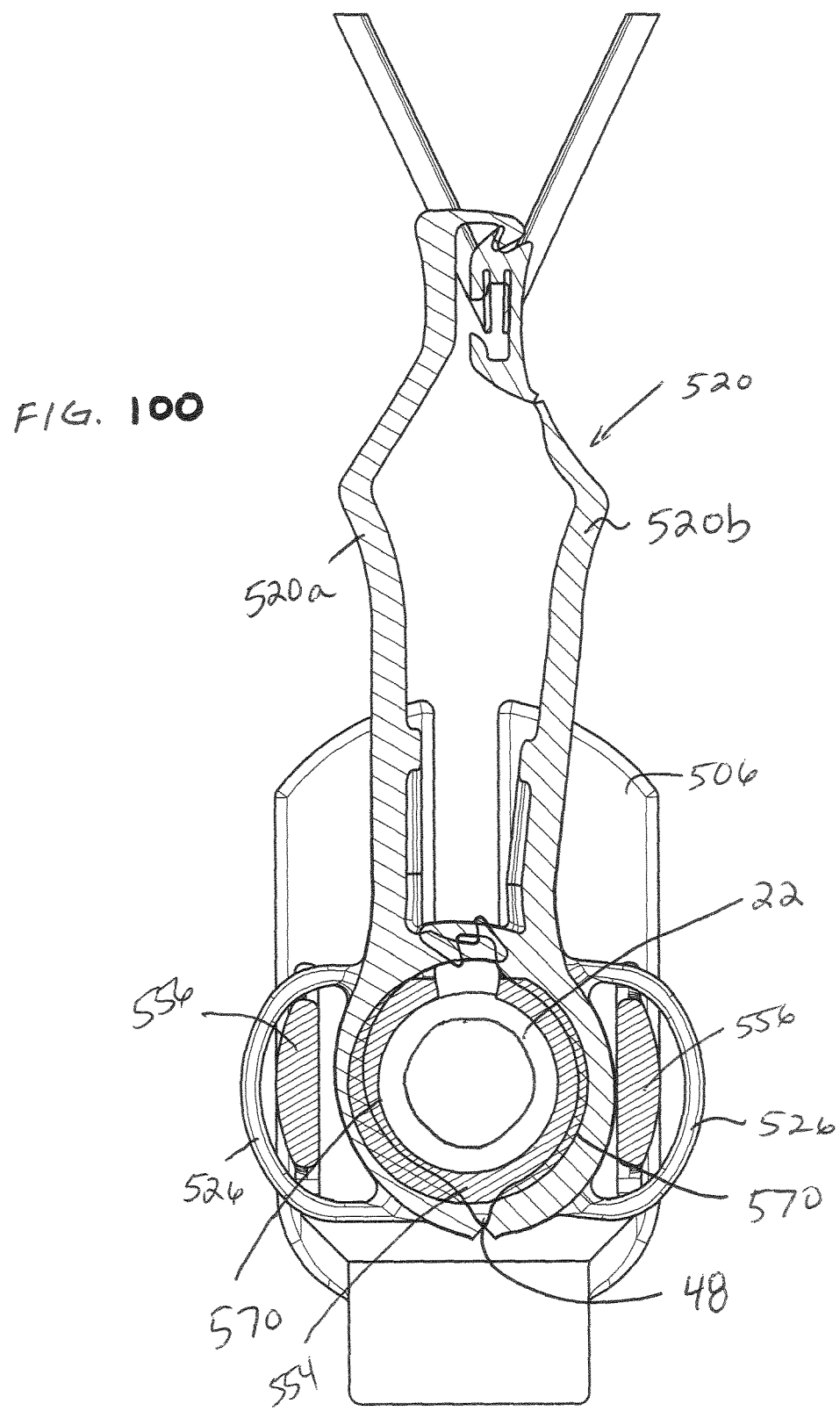

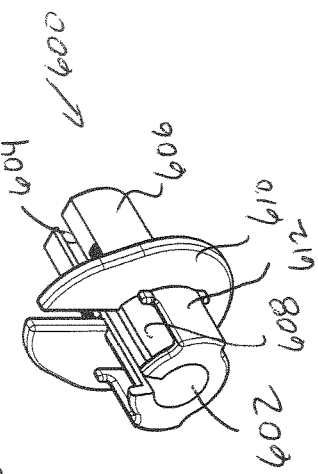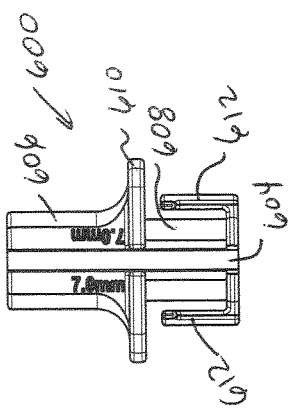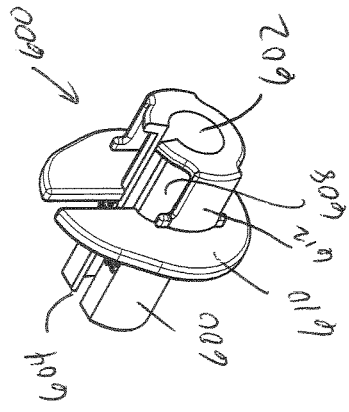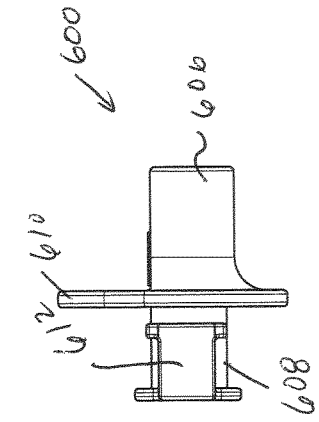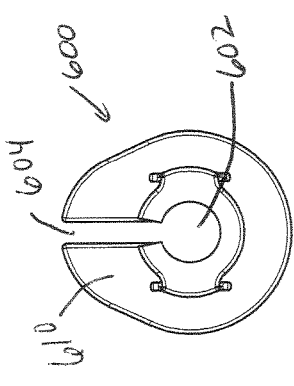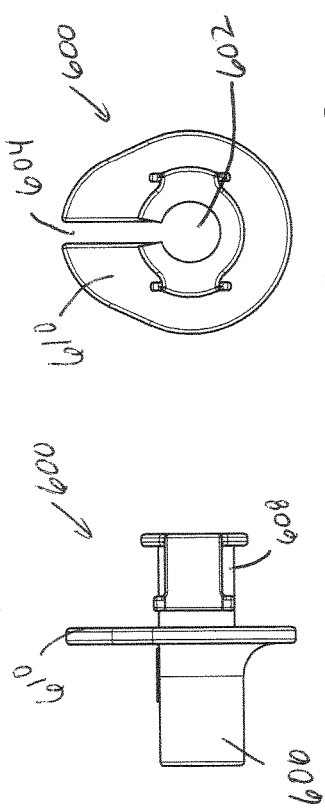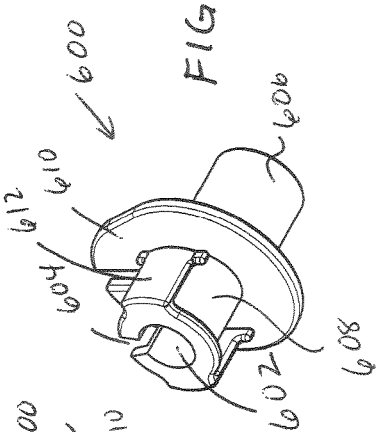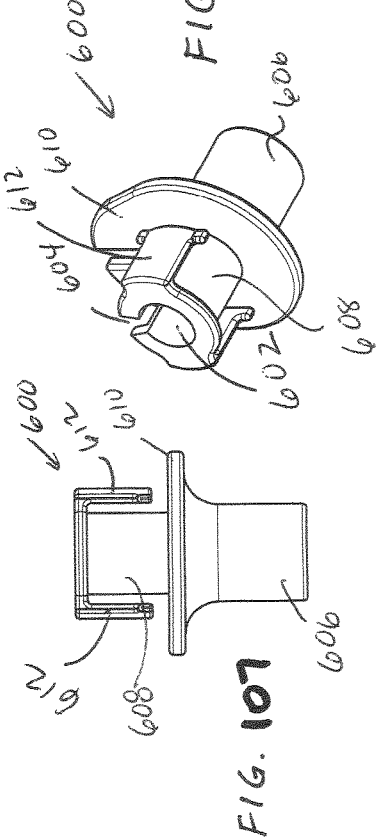

ENDOTRACHEAL TUBE RETENTION SYSTEM

CROSS-REFERENCE TO RELATED APPLICATIONS

This application is a continuation of U.S. application Ser. No. 14/216,257, filed Mar. 17, 2014, which claims the benefit of provisional U.S. Appl. No. 61/791,663, filed Mar. 15, 2013. U.S. application Ser. No. 14/216,257 is hereby incorporated by reference.

FIELD

The technology described herein relates to an endotracheal tube retention system.

BACKGROUND

For many patients in Intensive Care Units ("ICUs"), an endotracheal tube is the only lifeline that connects the ICU patient to a critical supply of oxygen. If an endotracheal tube becomes dislodged or is accidentally removed, the patient only has mere moments for the endotracheal tube to be replaced before the damaging effects of hypoxia start to occur. If the patient is accidentally extubated and no healthcare professional is cognizant of the situation, the patient could die within minutes as a result of cerebral hypoxia. Thus, it is a matter of life and death that the endotracheal tube remains securely in place to maintain consistent and reliable oxygen delivery.

A bridling system is presently used with feeding tubes, as described in U.S. Pat. No. 7,534,228 to Williams, entitled "Bridle Catheter with Umbilical Tape," the disclosure of which is incorporated herein by reference in its entirety. Williams discloses a device that uses a flexible member 2 with a magnet 4 attached to one end of the flexible member 2 and an umbilical tape 6 attached to the flexible member 2. The flexible member 2 is inserted into a first naris 8 of a patient's nose 10 using an insertion tool 12 which makes the flexible member 2 stiff enough to be inserted into the nasal cavity. A retrieving tool 14 having a magnetic end 4 is inserted into a second naris 16 of the patient's nose 10 and couples with the magnet 4 of the flexible member 2. Once the retrieving tool 14 and the flexible member 2 are coupled magnetically behind the posterior nasal septum of the patient 24, the retrieving tool 14 is pulled out of the second naris 16 and the flexible member 2 follows around the vomer bone and out the second naris 16, pulling the umbilical tape 6 with it. The flexible member 2 is pulled entirely out of the second naris 16, leaving the umbilical tape 6 in position behind the vomer bone.

The Williams bridling system uses a flexible tape 6 that is inserted behind the vomer bone in the patient's nose 10 so that a portion of the tape 6 extends from each naris 8, 16 and is coupled to a feeding tube to hold the feeding tube in place. The feeding tube is clipped to the tape 6 (also known as a "bridle"). The patient is deterred from removing the feeding tube because pulling on the feeding tube will result in pulling on the tape 6. Because of the position of the tape 6 behind the vomer bone, pulling on the tape 6 will cause the patient pain or discomfort. In this manner, a patient is deterred from removing the feeding tube. The use of an umbilical tape 6 provides other important benefits, as described in the Williams patent.

A number of endotracheal tube anchoring devices are presently available in the healthcare market. These often require that adhesive tape be applied to a patient's face or involve some sort of stabilizing component to rest against a patient's face. One drawback to adhesive use is that adhesive applied to the skin may cause the skin to break down, which can cause patient discomfort and lead to infection. If the retention of the endotracheal tube is dependent upon adhesive, the adhesive may also break down resulting in failure of the system. In addition, stabilizers positioned against a patient's skin may result in skin ulcers or other complications. The use of adhesive and stabilizers is contradicted in the case of burn patients. There is a need in the medical field for a device that can assist in consistently retaining an endotracheal tube within a patient's airway without the use of stabilizers or adhesive.

SUMMARY

In accordance with the teachings described herein, a floating clip for holding a tube that is inserted into a facial orifice of a patient is disclosed. In addition, a clip system for holding a tube that is inserted into a facial orifice of a patient is disclosed. Furthermore, a system and a method for suspending a tube that is inserted into a facial orifice or a mouth of a patient are disclosed.

BRIEF DESCRIPTION OF THE DRAWING FIGURES

Figure 9:
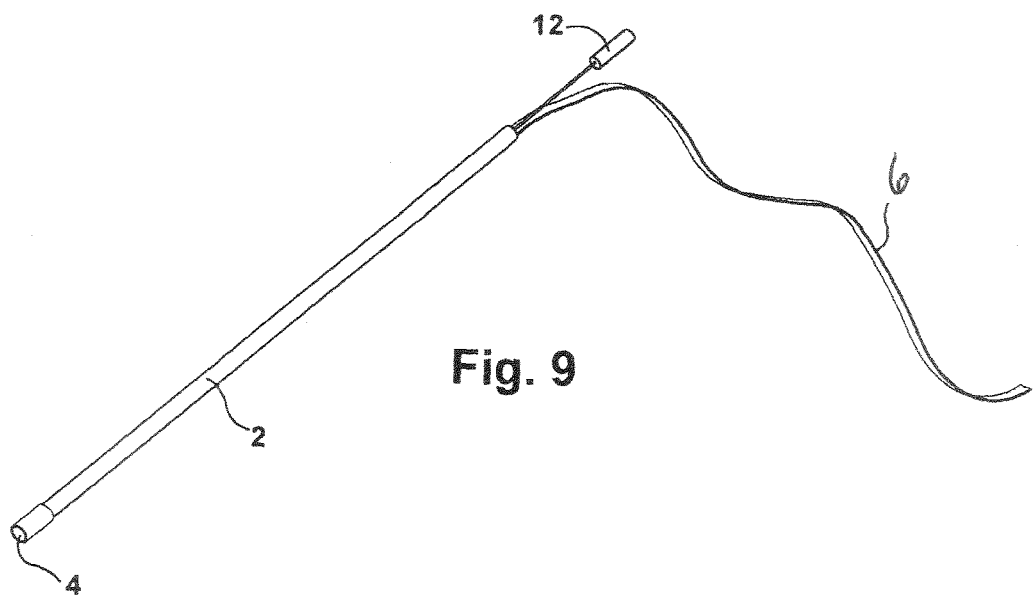
Figure 10:
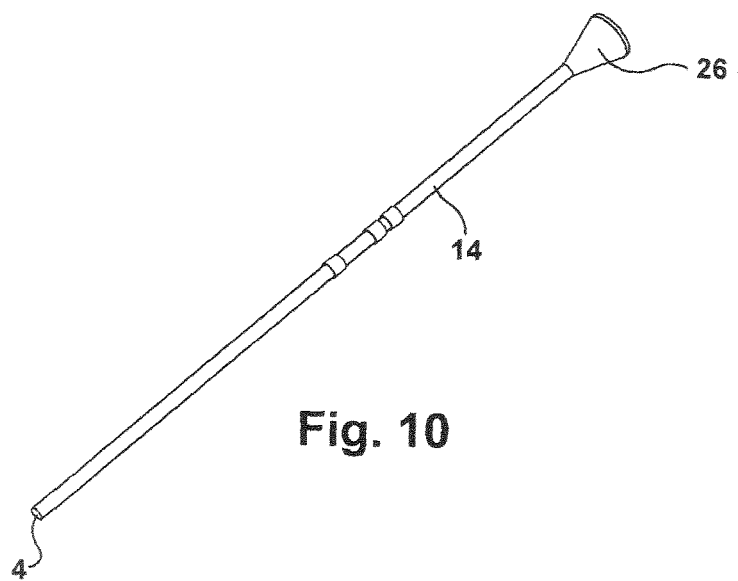
Figure 11:
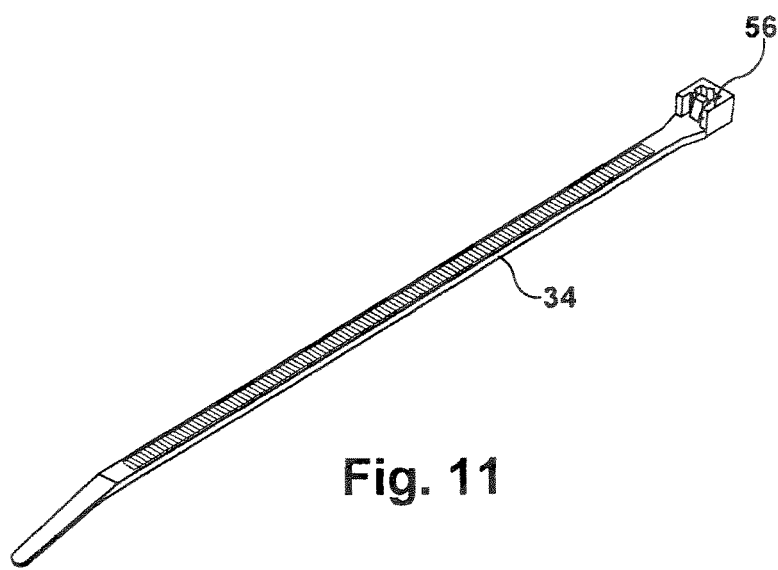
Figure 12:
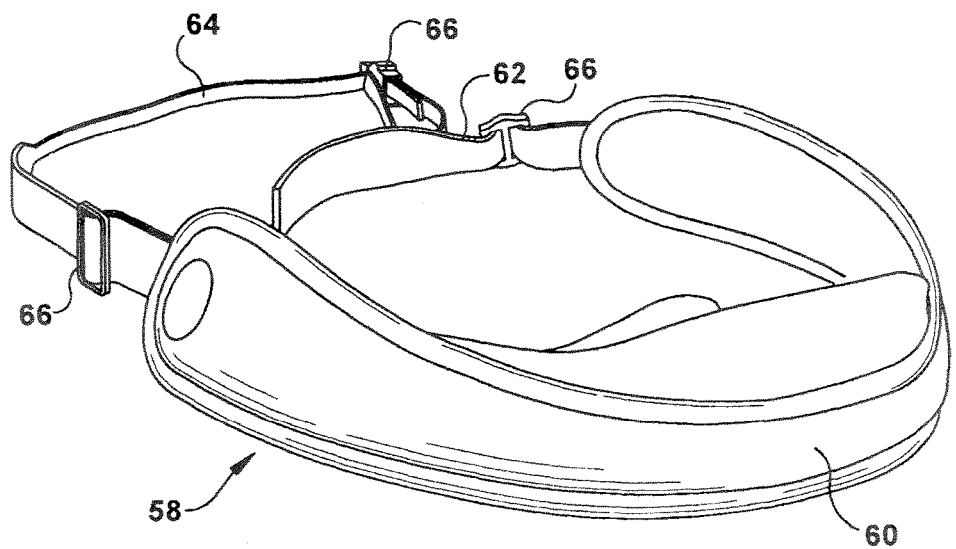
Figure 13:
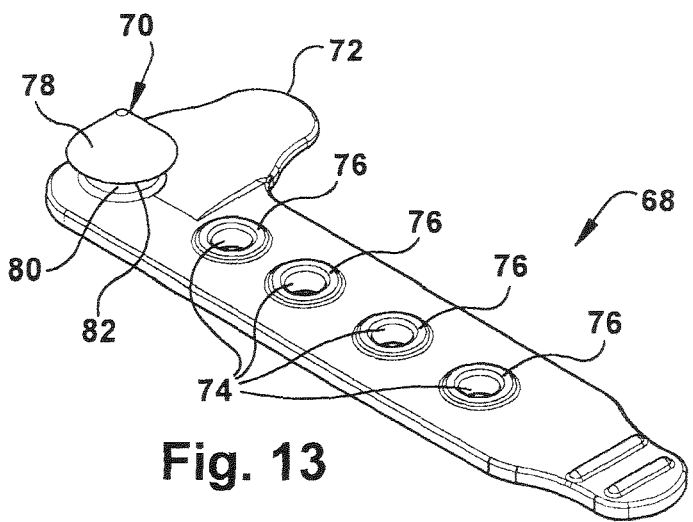
Figure 14:
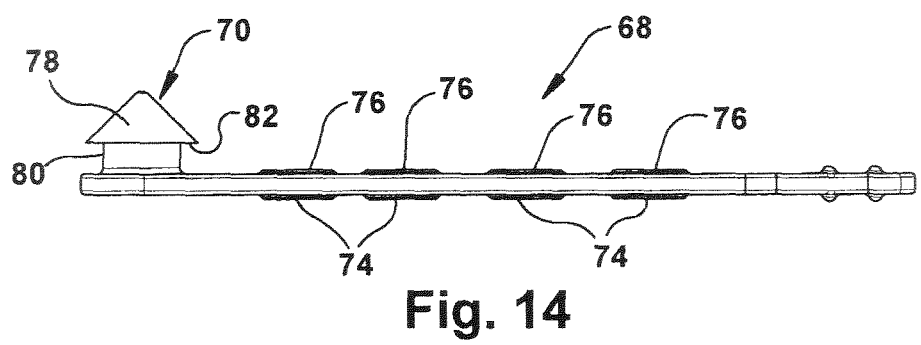
Figure 15:
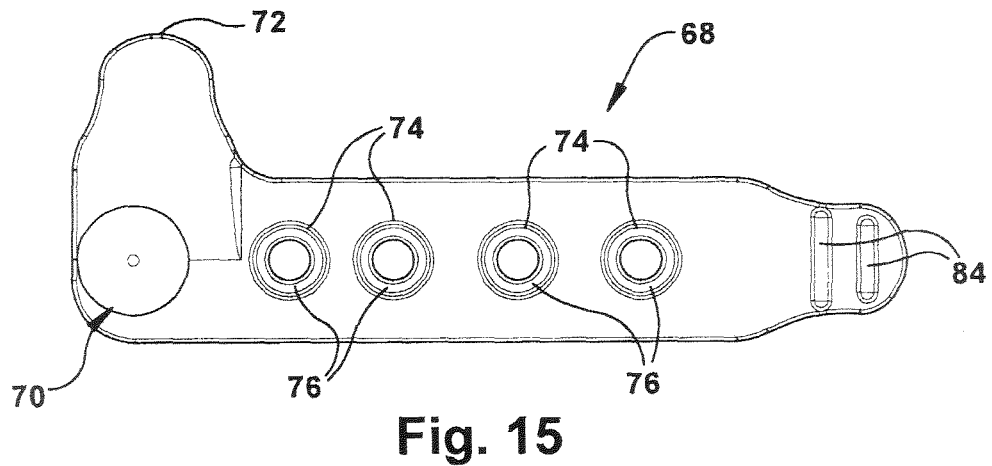
Figure 16A:
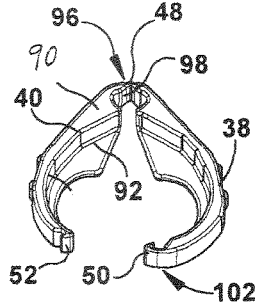
Figure 16B:
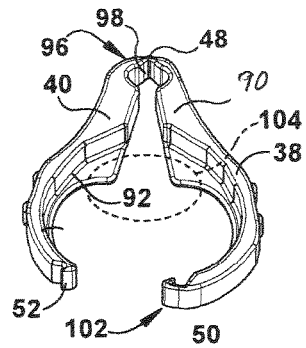
Figure 16C:
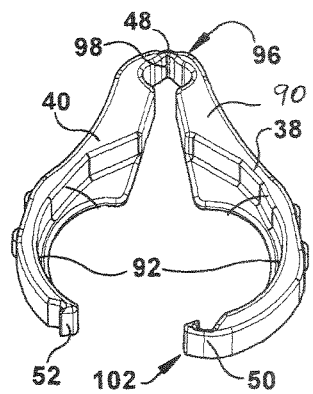
Figure 17:
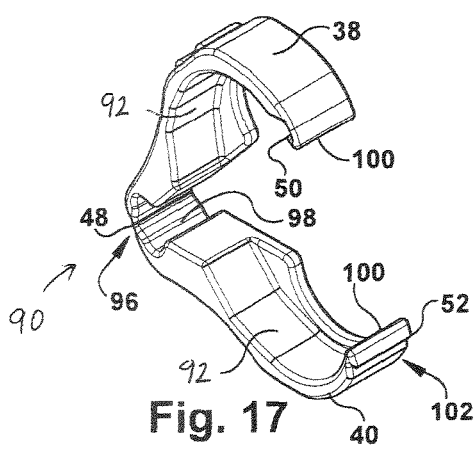
Figure 18:
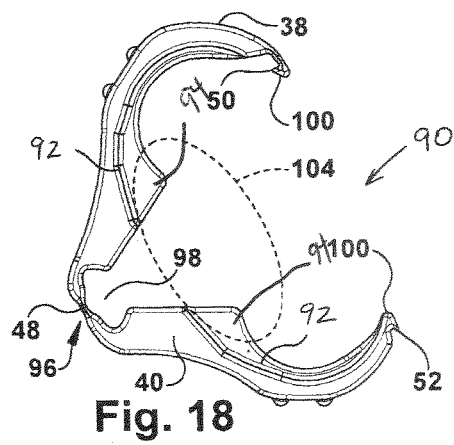
Figure 19:
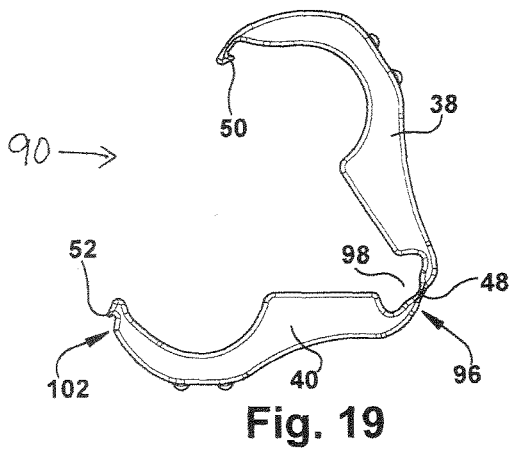
Figure 20:
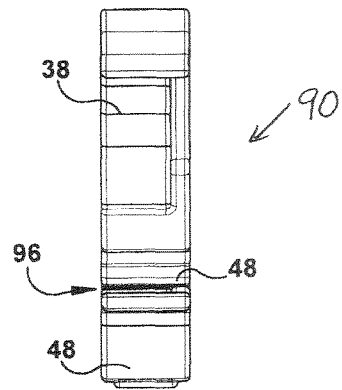
Figure 21:
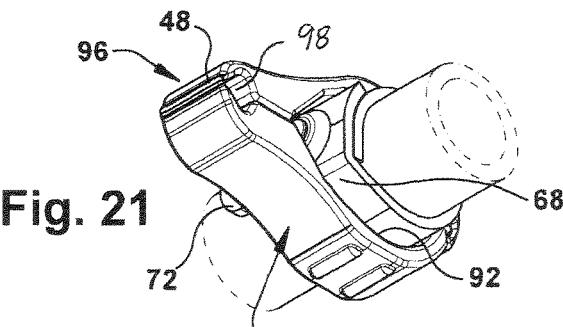
Figure 22:
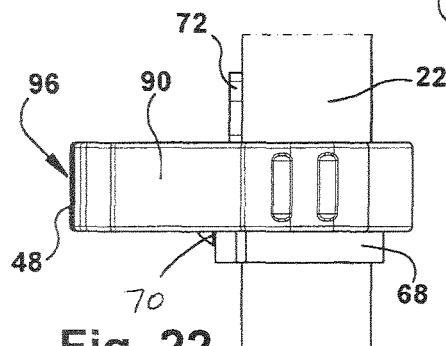
Figure 23:
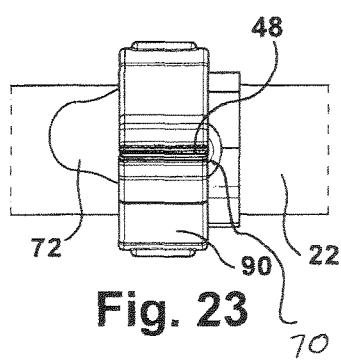
Figure 24:
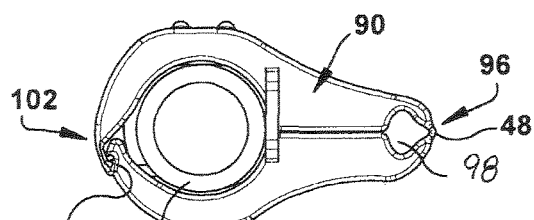
Figure 25:
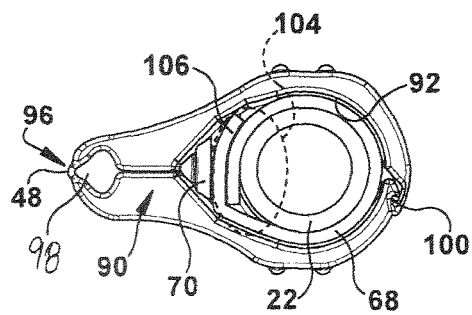
Figure 26:
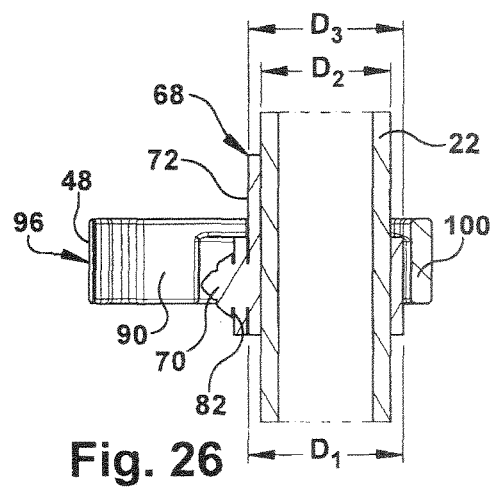
Figure 27:
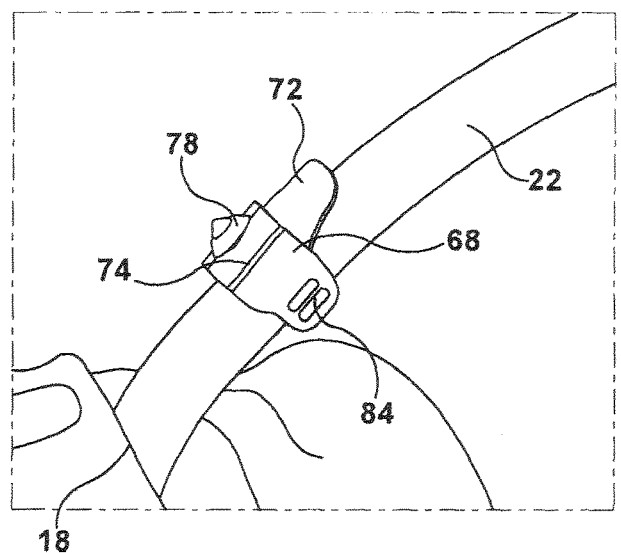
Figure 28:
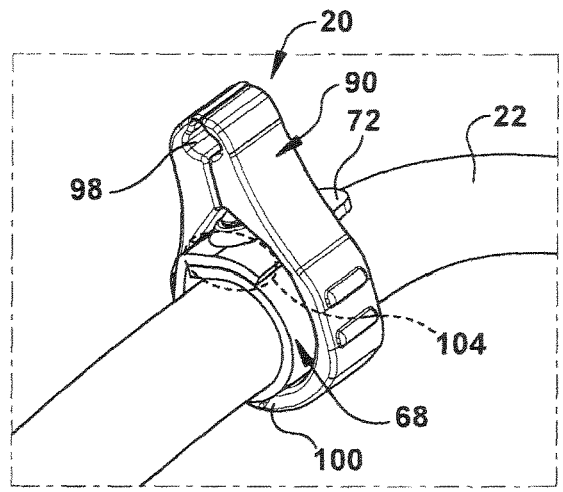
Figure 29:
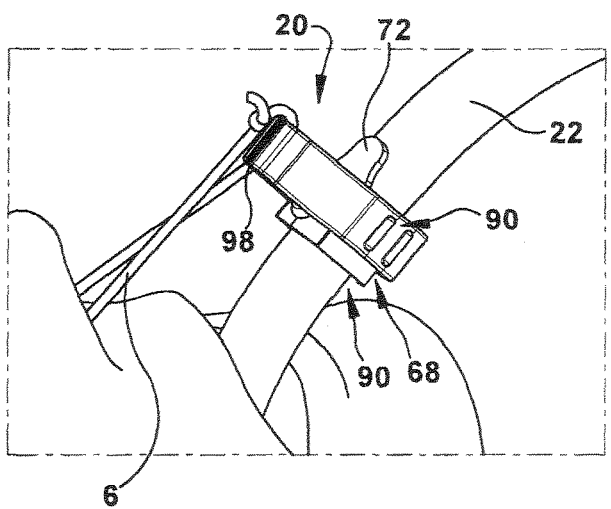
Figure 30:
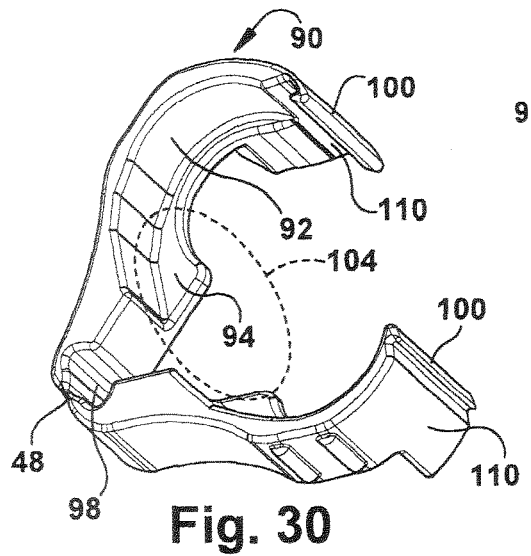
Figure 31:
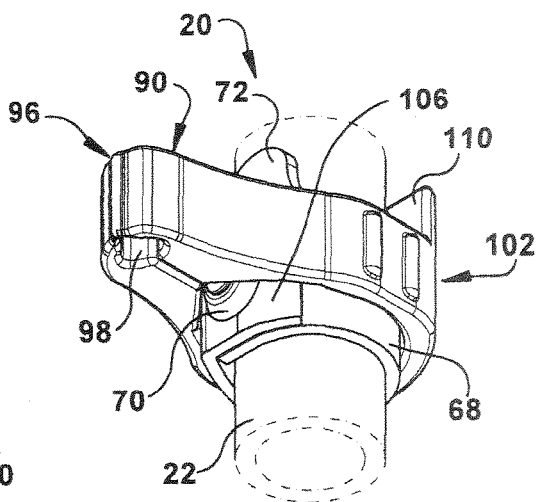
Figure 32:
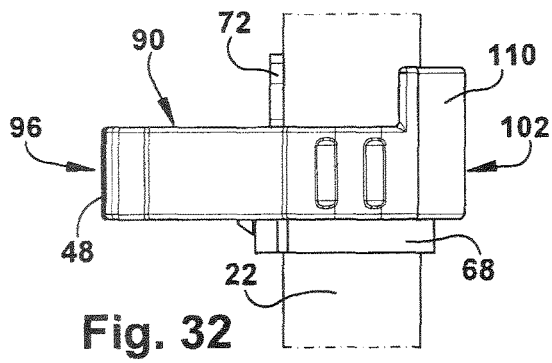
Figure 33:
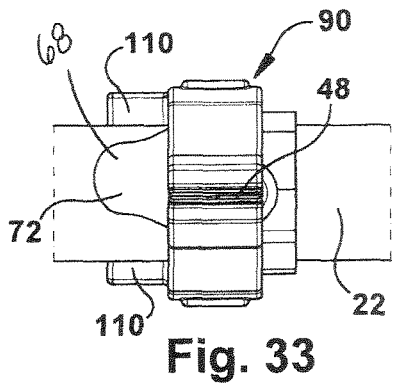
Figure 34:
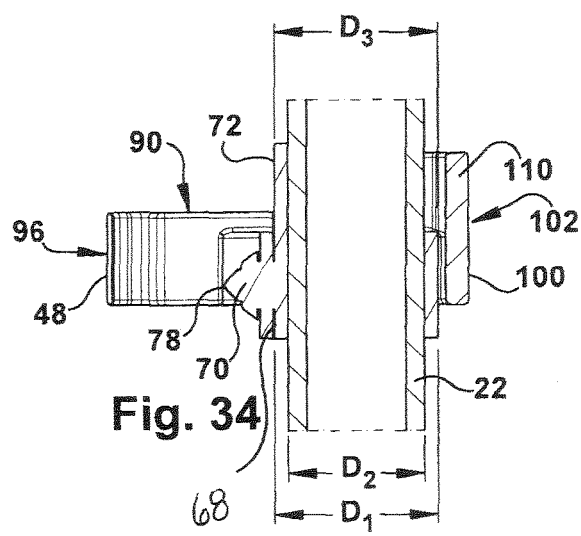
Figure 35:
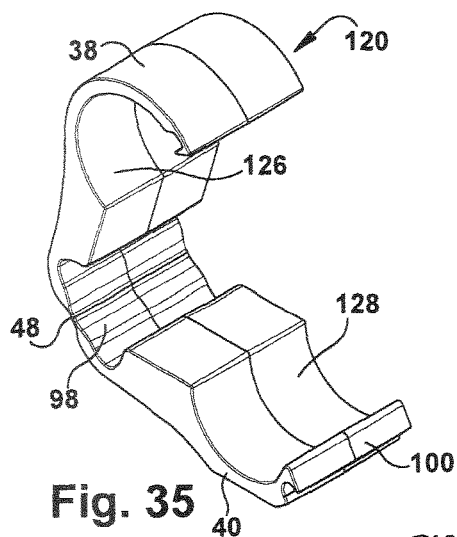
Figure 36:
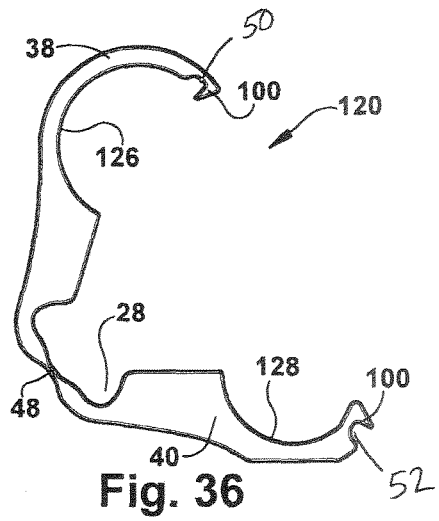
Figure 37:
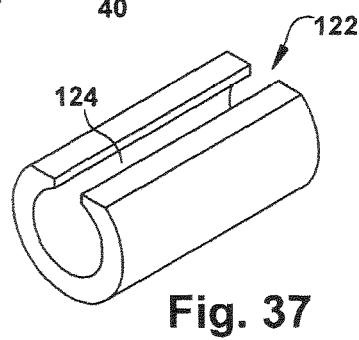
Figure 38:
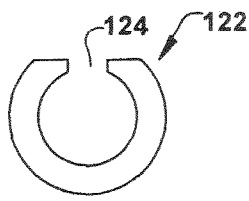
Figure 39:
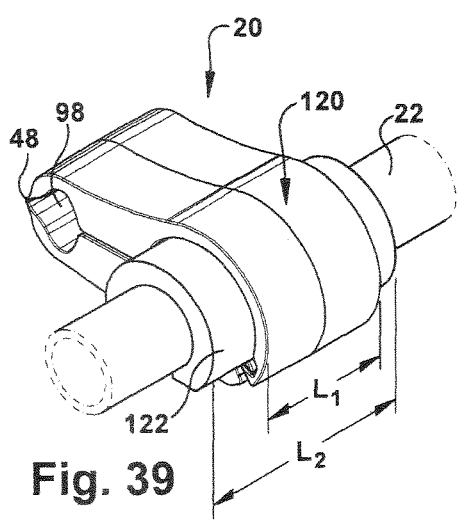
Figure 40:
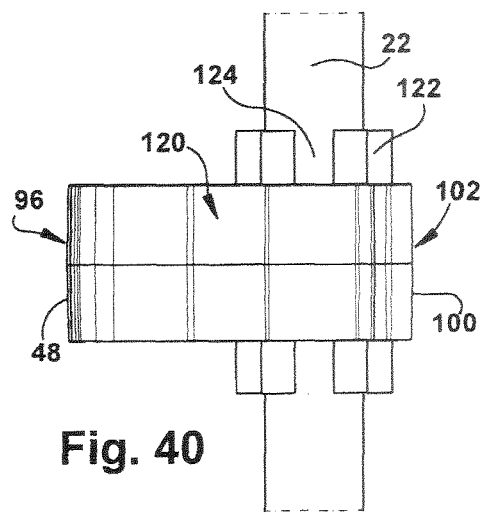
Figure 41:
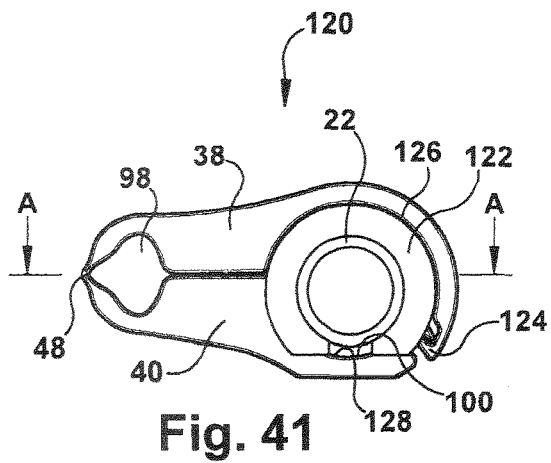
Figure 42:
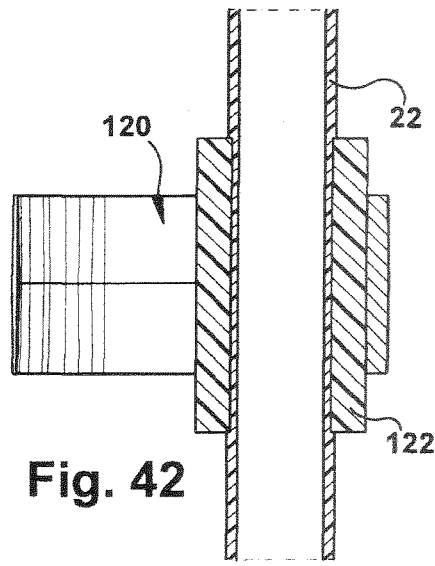
Figure 43:
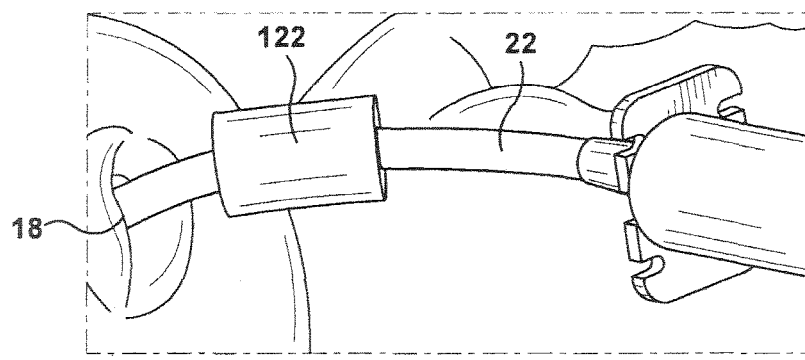
Figure 44:
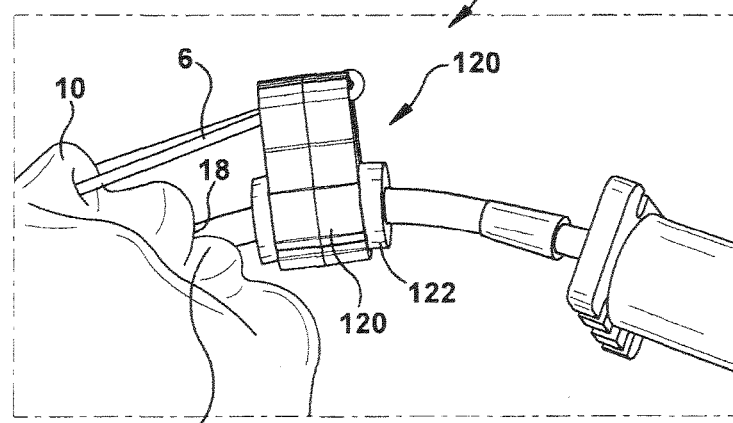
Figure 45:
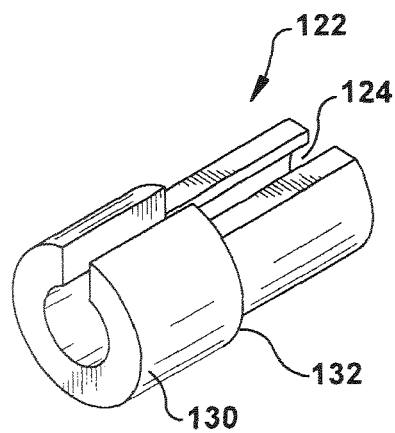
Figure 46:
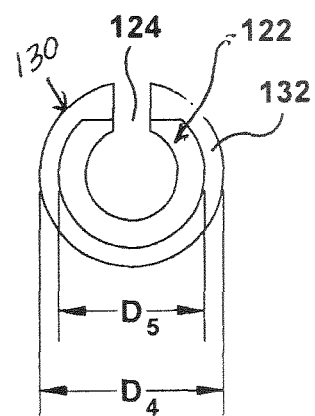
Figure 47:
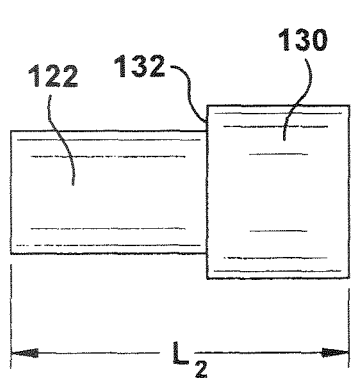
Figure 48:
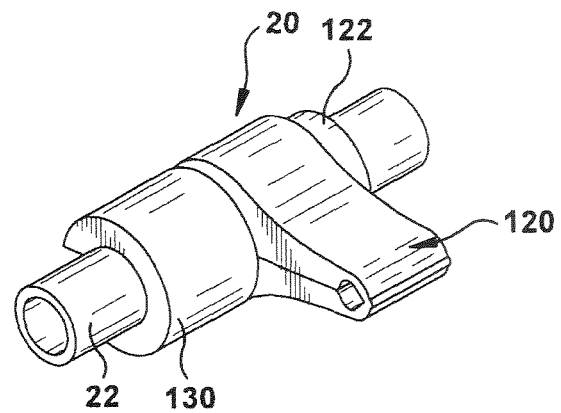
Figure 49:
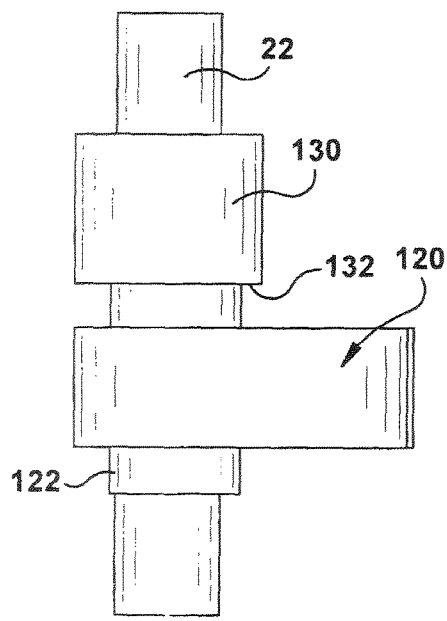
Figure 50:
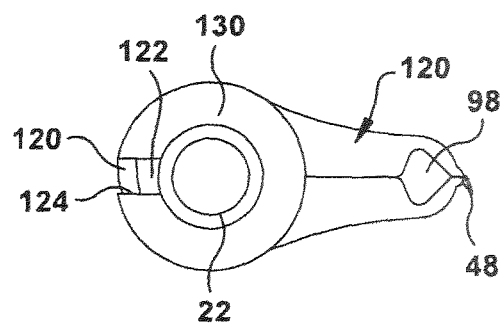
Figure 51:
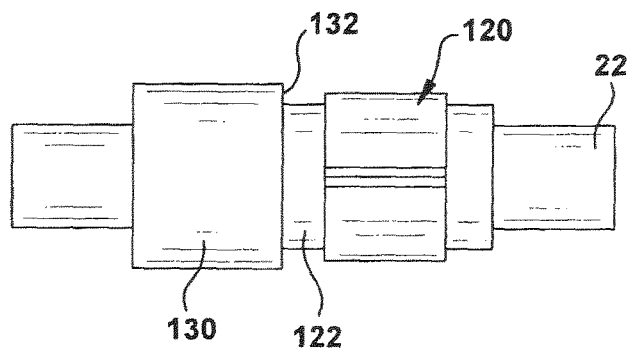
Figure 52:
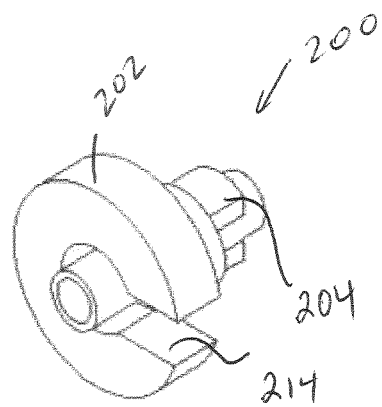
Figure 53:
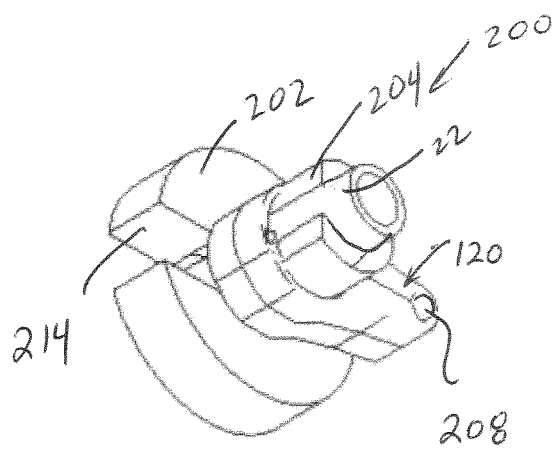
Figure 54:
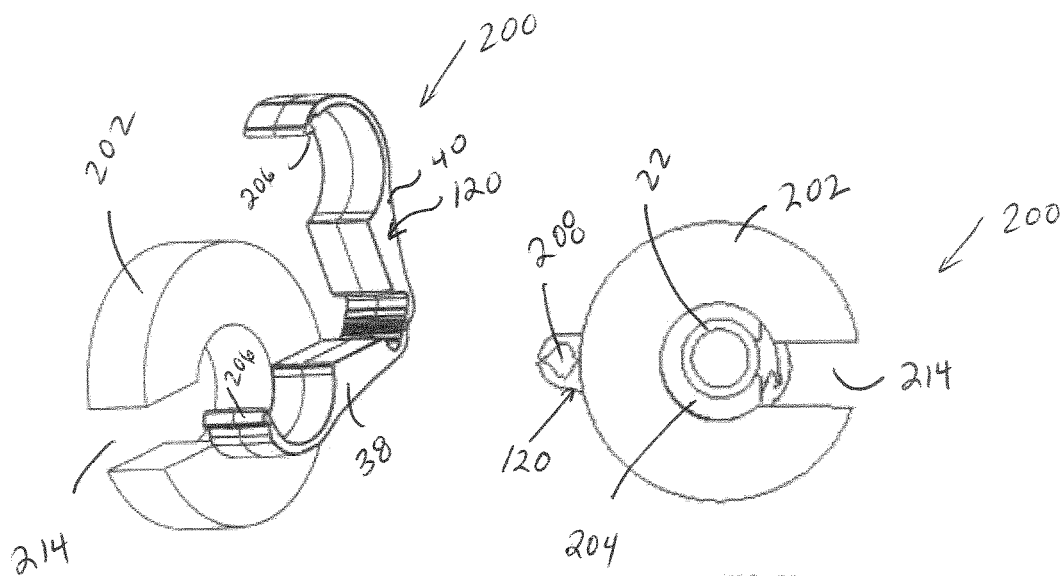
Figure 55:
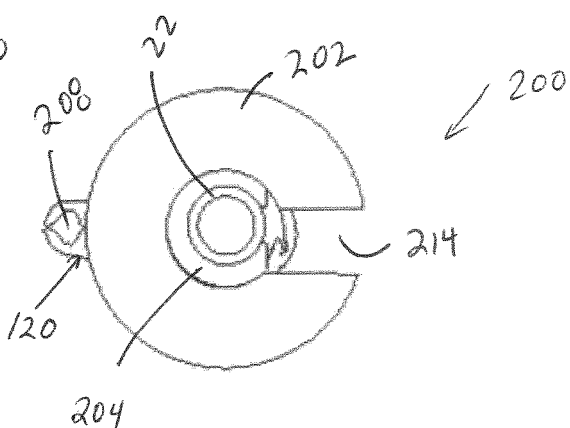
Figure 56:
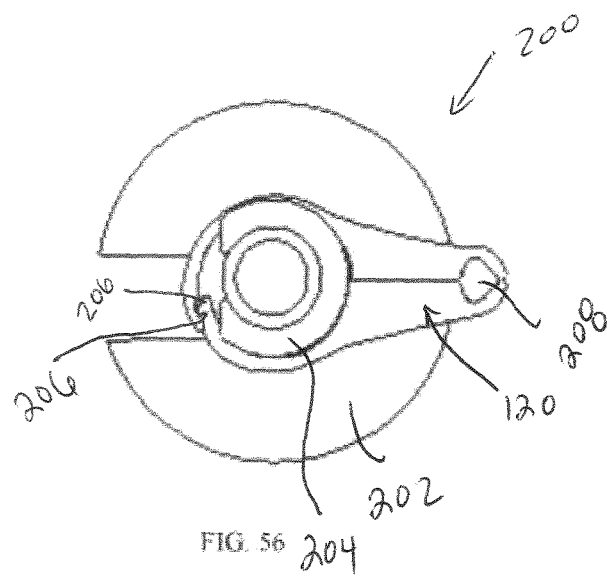
Figure 57:
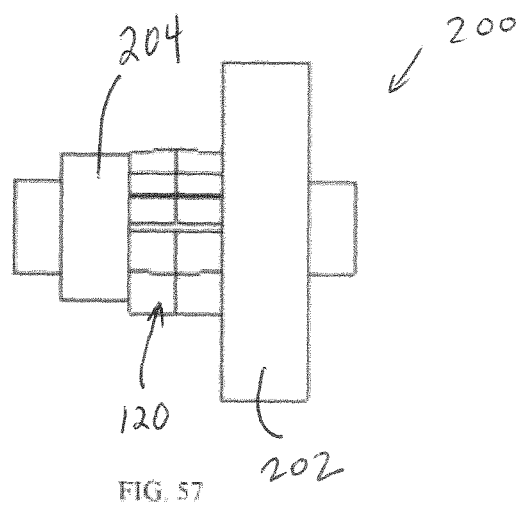
Figure 58:
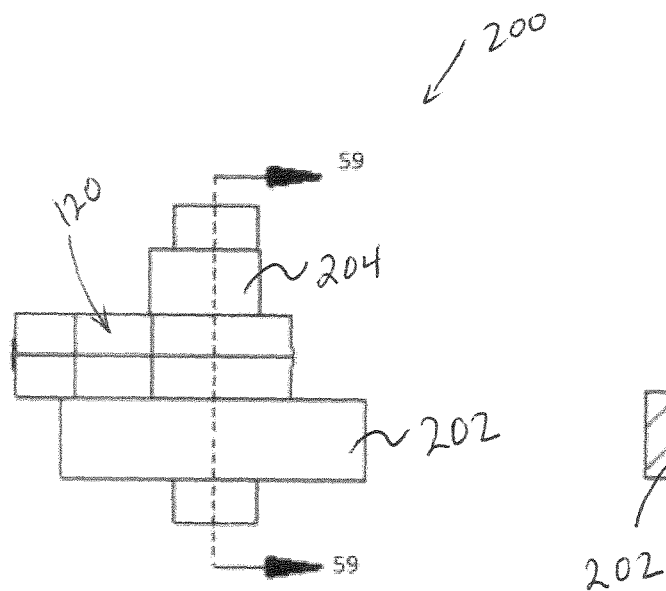
Figure 59:
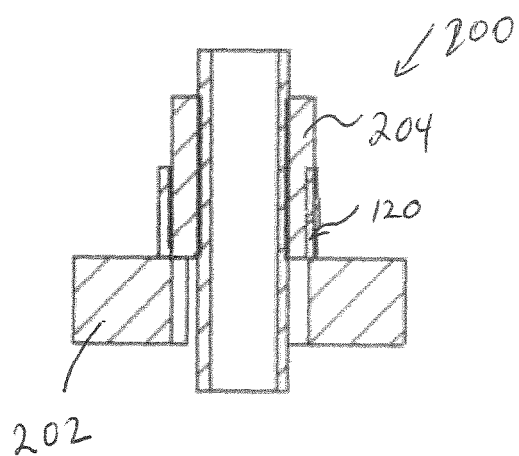
Figure 60:
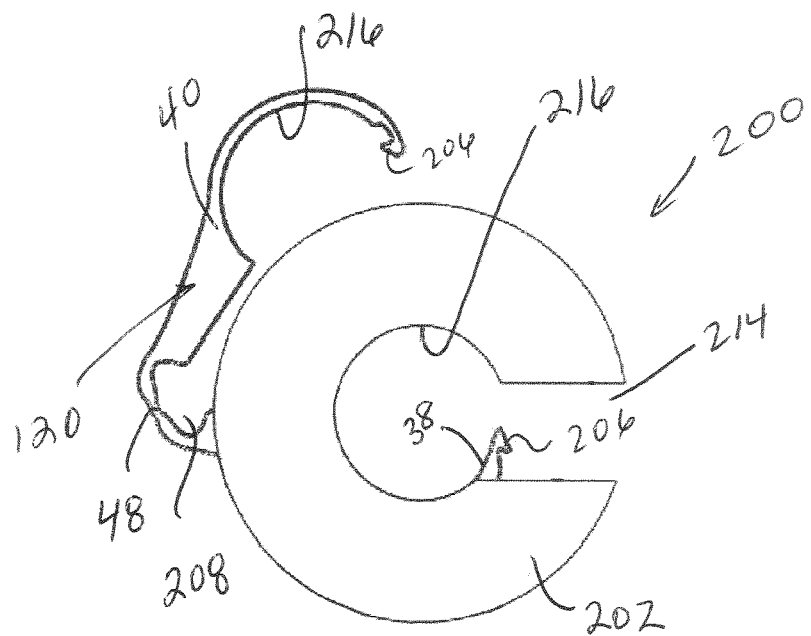
Figure 61:
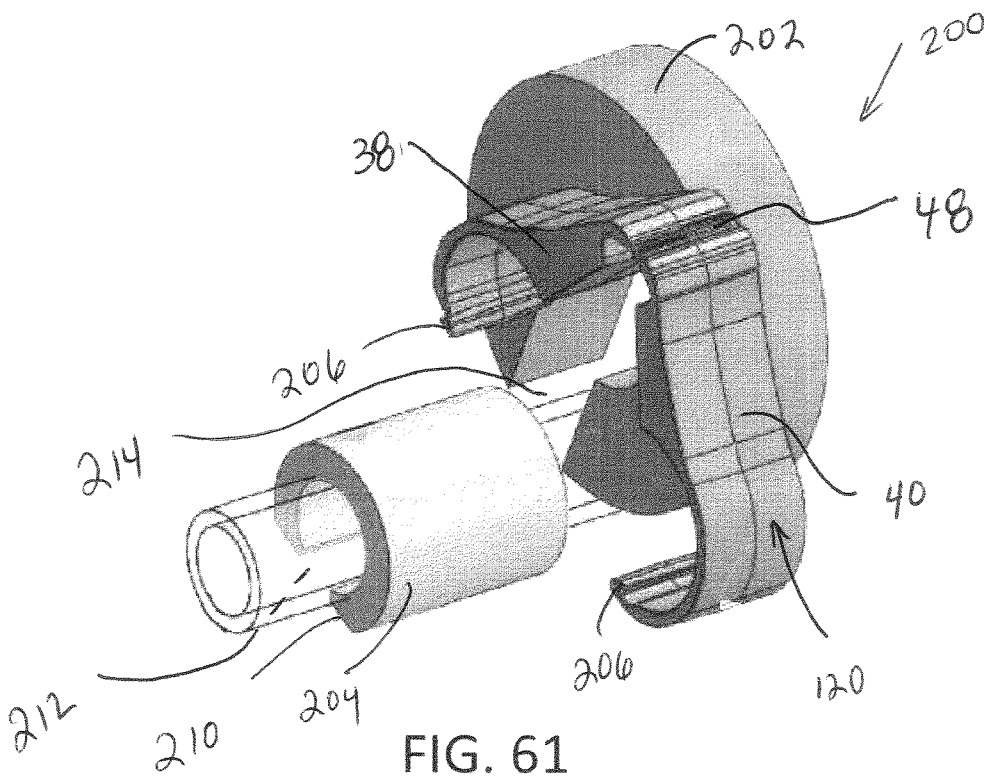

FIG. 9 is a perspective view of part of a bridle installation system in the form of a flexible member 2 having a stiffening device 12 and an umbilical tape 6 or similar flexible member 2 attached thereto that may be utilized in installing an umbilical tape 6 or similar flexible member 2 behind the vomer bone of a patient;

FIG. 10 is a perspective view of another part of a bridle installation tool in the form of a retrieving member 14 for retrieving the flexible member 2 of FIG. 9 behind the vomer bone of a patient and for pulling the flexible member 2 and tape 6 through the nose 10;

FIG. 11 is perspective view of a cable tie for use with the example endotracheal tube retention system of FIGS. 1-8;

FIG. 12 is a perspective view of a cushioned neck strap that may be utilized with the example endotracheal tube retention system of FIGS. 1-8 or any of the following embodiments;

FIG. 13 is a perspective view of an adjustable strap for use with an example endotracheal tube retention system;

FIG. 14 is a side view of the adjustable strap of FIG. 13;

FIG. 15 is a top view of the adjustable strap of FIG. 13;

FIGS. 16a-c are a series of front views of differently sized floating clips shown in an open position for use with the adjustable strap shown in FIGS. 13-15 in connection with another example endotracheal tube retention system;

FIG. 17 is a perspective view of one of the floating clips of FIGS. 16a-c, showing the clip in an open position;

FIG. 18 is a front view of the floating clip of FIG. 17;

FIG. 19 is a back view of the floating clip of FIG. 17;

FIG. 20 is top view of the floating clip of FIG. 17;

FIG. 21 is a perspective view of the endotracheal tube retention system components of FIGS. 13 and 18 coupled together around an endotracheal tube, with the right side of the tube, as shown in the drawing, being the side that extends toward a patient's face;

FIG. 22 is a right side view of the endotracheal tube system of FIG. 21;

FIG. 23 is a top view of the endotracheal tube system of FIG. 21;

FIG. 24 is a rear view of the endotracheal tube system of FIG. 21;

FIG. 25 is a front view of the endotracheal tube system of FIG. 21;

FIG. 26 is a cross-sectional side view of the endotracheal tube system of FIG. 21, taken at line A-A in FIG. 25;

FIG. 27 is a perspective view showing an endotracheal tube positioned in a patient's airway with the strap of FIG. 13 installed around the tube;

FIG. 28 is a perspective front view of an endotracheal tube showing the strap of FIG. 13 and the floating clip of FIG. 17 installed around the endotracheal tube;

FIG. 29 is a perspective side view similar to that of FIG. 28, but with a bridle positioned in a nasal cavity of a patient and coupled to the floating clip;

FIG. 30 is perspective front view of an alternative example of the floating clip having an extension on the clip to deter rotation of the clip;

FIG. 31 is a perspective front view of the clip of FIG. 30 installed on the strap of FIG. 13 around an endotracheal tube;

FIG. 32 is a right side view of the endotracheal tube system of FIG. 31;

FIG. 33 is a top view of the endotracheal tube system of FIG. 31;

FIG. 34 is a cross-sectional side view of the endotracheal tube system of FIG. 31;

FIG. 35 is a perspective view of an alternative clip for use with the example endotracheal tube system in an open position;

FIG. 36 is a front view of the clip of FIG. 35, with the opposite side view being a mirror image thereof;

FIG. 37 is a perspective view of a compressible tube for positioning around an endotracheal tube over which the clip of FIG. 35 is installed;

FIG. 38 is a front/rear view of the compressible tube of FIG. 37;

FIG. 39 is a perspective view of the clip of FIG. 35 installed on the compressible tube of FIG. 37 and installed on an endotracheal tube;

FIG. 40 is a bottom view of the endotracheal tube system of FIG. 39 installed on an endotracheal tube, but could also represent a top view if the connection portion of the clip is preferred to be positioned on top;

FIG. 41 is a front view of the endotracheal tube system of FIG. 40;

FIG. 42 is a cross-sectional top view of the endotracheal tube system of FIG. 39 taken at line A-A in FIG. 40;

FIG. 43 is a perspective view of the compressible tube of FIG. 37 installed on an endotracheal tube of a patient;

FIG. 44 is a perspective side view of the compressible tube and clip according to FIG. 39 installed on an endotracheal tube of a patient;

FIG. 45 is an alternative embodiment of the compressible tube of FIG. 37 where the compressible tube has a bumper or mouth guard;

FIG. 46 is a rear view of the compressible tube/bumper of FIG. 45;

FIG. 47 is a left side view of the compressible tube/bumper of FIG. 45;

FIG. 48 is a perspective view of the compressible tube/bumper of FIG. 45 installed on an endotracheal tube with a clip installed over the compressible tube/bumper;

FIG. 49 is a side view of an endotracheal tube system according to FIG. 48;

FIG. 50 is a front view of an endotracheal tube system according to FIG. 48;

FIG. 51 is a top view of an endotracheal tube system according to FIG. 48;

FIG. 52 is a front end perspective view of another endotracheal tube retention system;

FIG. 53 is a rear end perspective view of the endotracheal tube retention system of FIG. 52;

FIG. 54 is a rear perspective view of part of the endotracheal tube retention system of FIG. 52, shown in an open position;

FIG. 55 is a front view of the endotracheal tube retention system of FIG. 52;

FIG. 56 is a rear view of the endotracheal tube retention system of FIG. 52;

FIG. 57 is a right side view of the endotracheal tube retention system of FIG. 56, as viewed from the right side of the system;

FIG. 58 is a top view of the endotracheal tube retention system of FIG. 56, as viewed from the top of the system;

FIG. 59 is a cross-sectional view of the endotracheal tube retention system of FIG. 58, taken along line 59-59;

FIG. 60 is a front view of the example endotracheal tube retention system of FIG. 52, with the clip in an open position;

FIG. 61 is a partially exploded view of the example endotracheal tube retention system of FIG. 52;

FIG. 62 is a front perspective view of another example endotracheal tube retention system;

FIG. 63 is a rear perspective view of the endotracheal tube retention system of FIG. 62;

FIG. 64 is a partially exploded view of the endotracheal tube retention system of FIG. 62, shown positioned on an endotracheal tube;

FIG. 65 is a front perspective view of the example endotracheal tube retention system of FIG. 64, with the various parts in an installed configuration on an endotracheal tube;

FIG. 66 is a cross-sectional view of the example endotracheal tube retention system of FIG. 65, taken along line 66-66.

Figure 67:
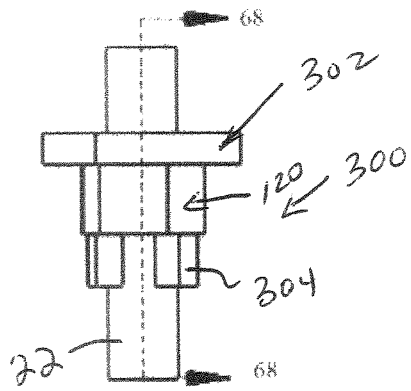
Figure 68:
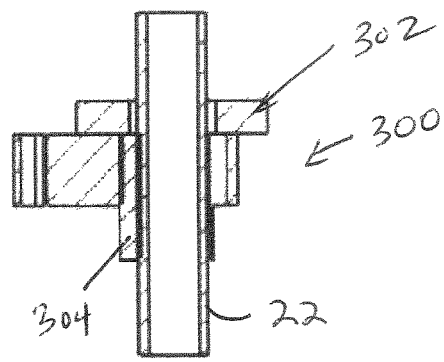
Figure 69:
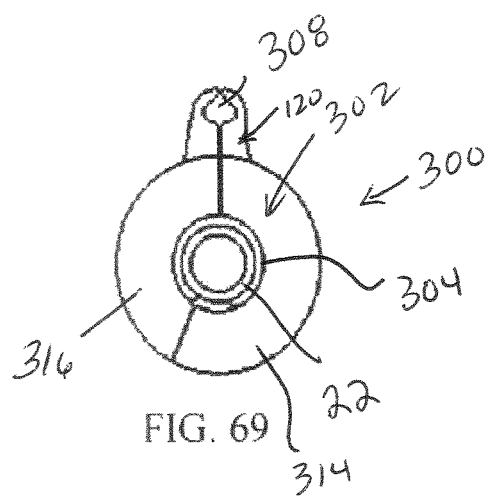
Figure 70:
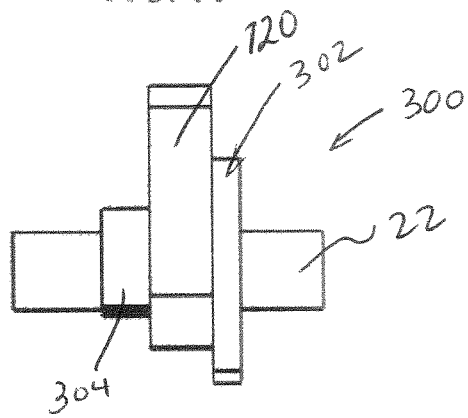
Figure 71:
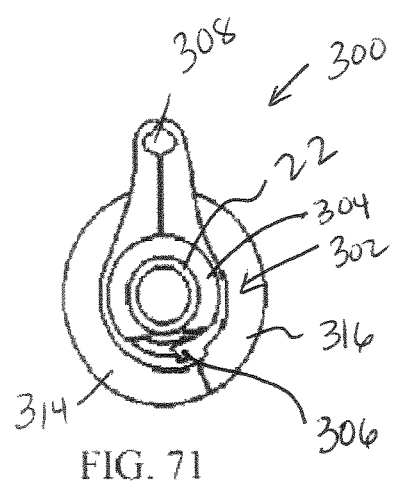
Figure 72:
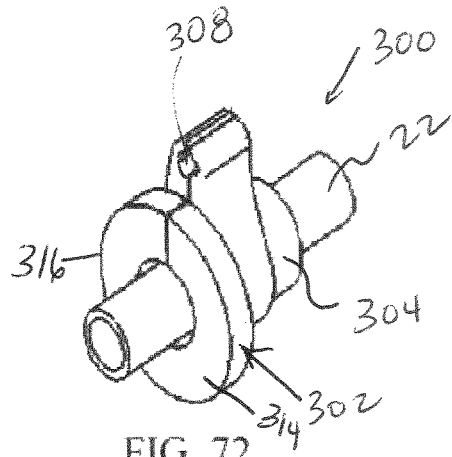
Figure 73:
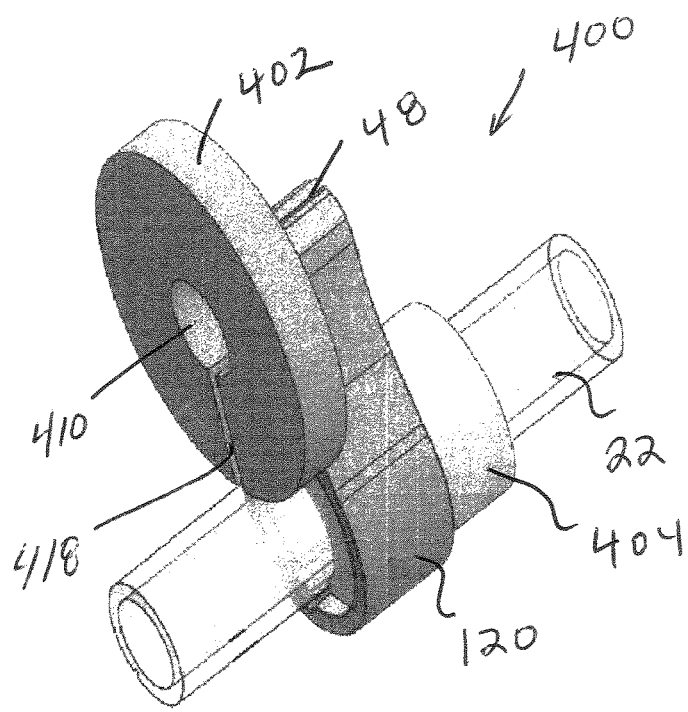
Figure 74:
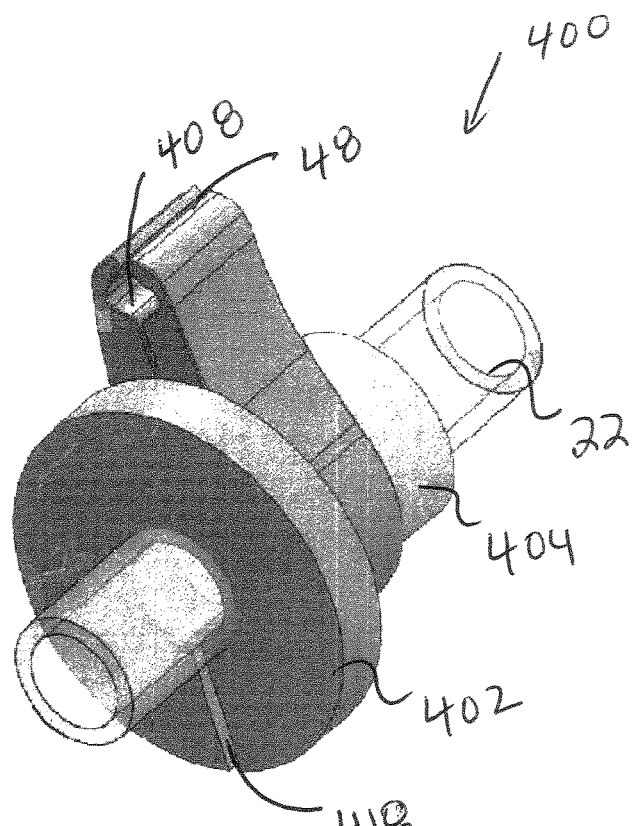
Figure 75:
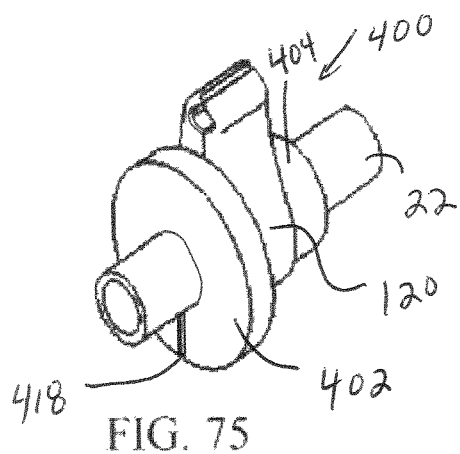
Figure 76:
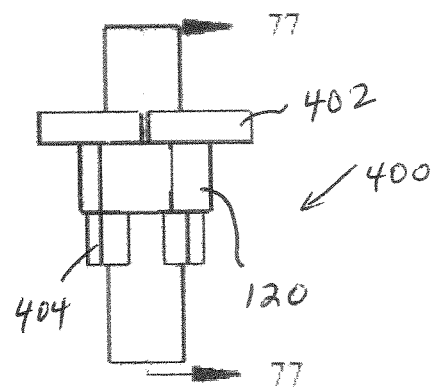
Figure 77:
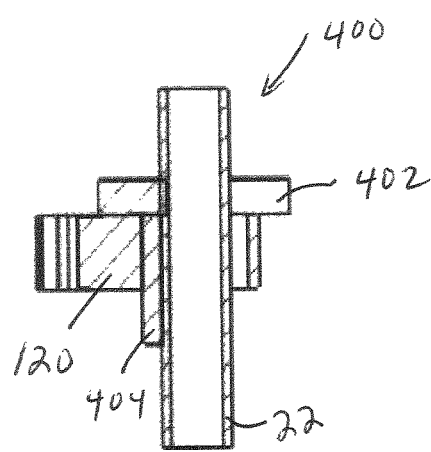
Figure 78:
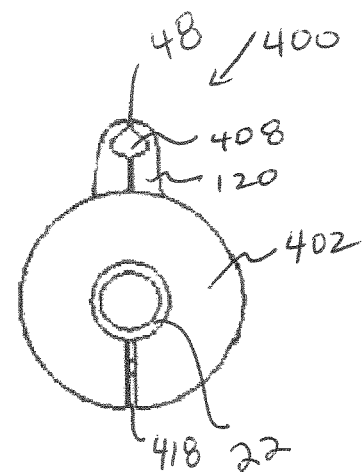
Figure 79:
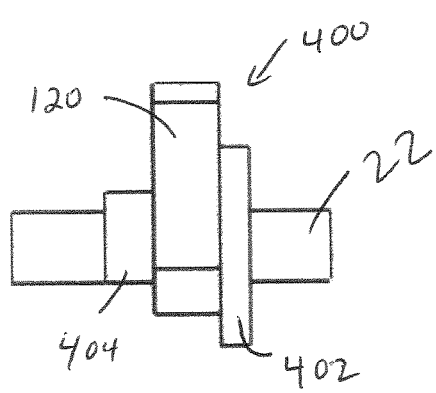
Figure 80:
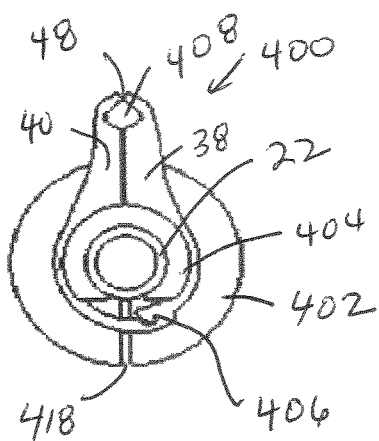
Figure 81:
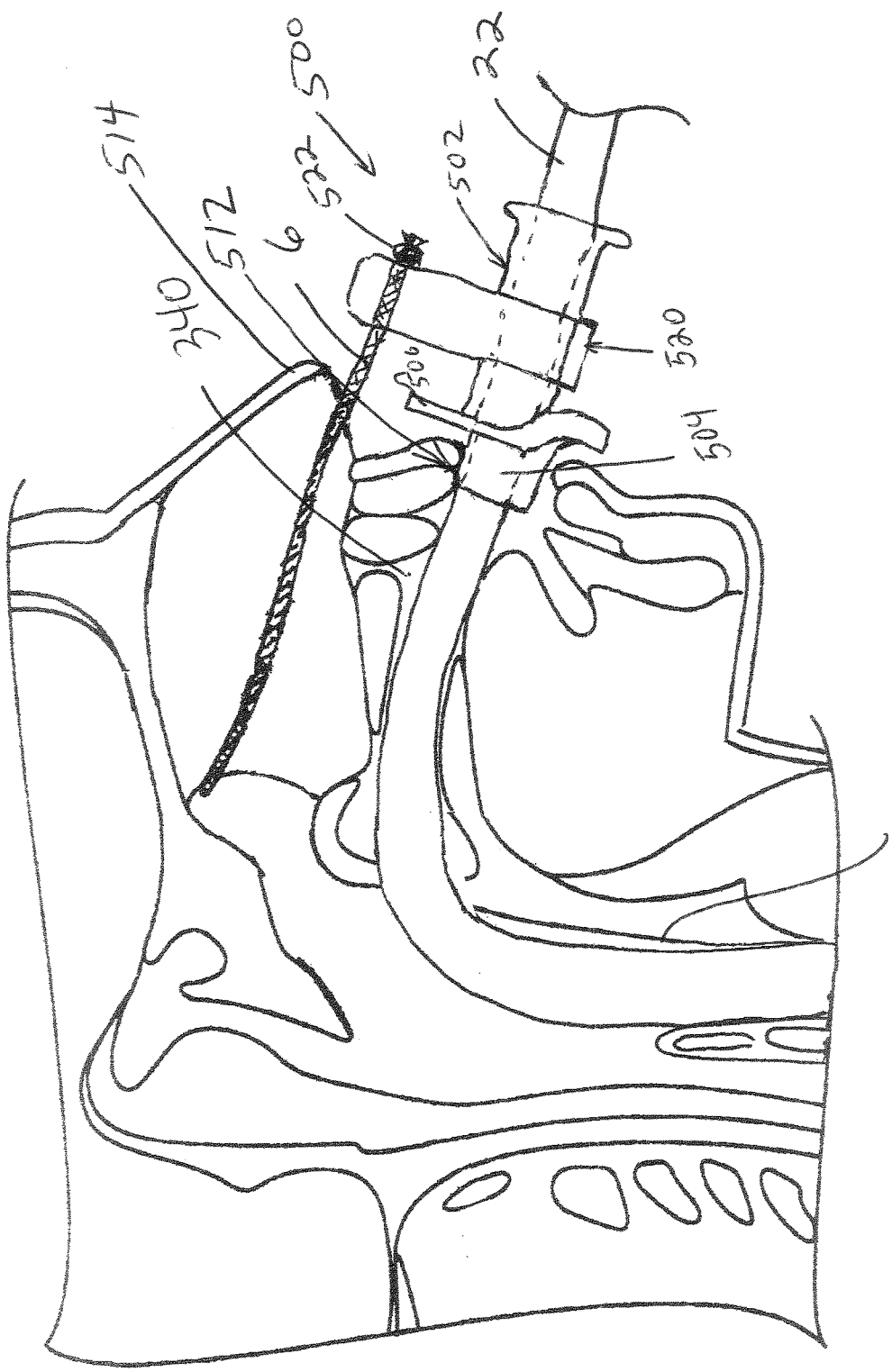
Figure 88:
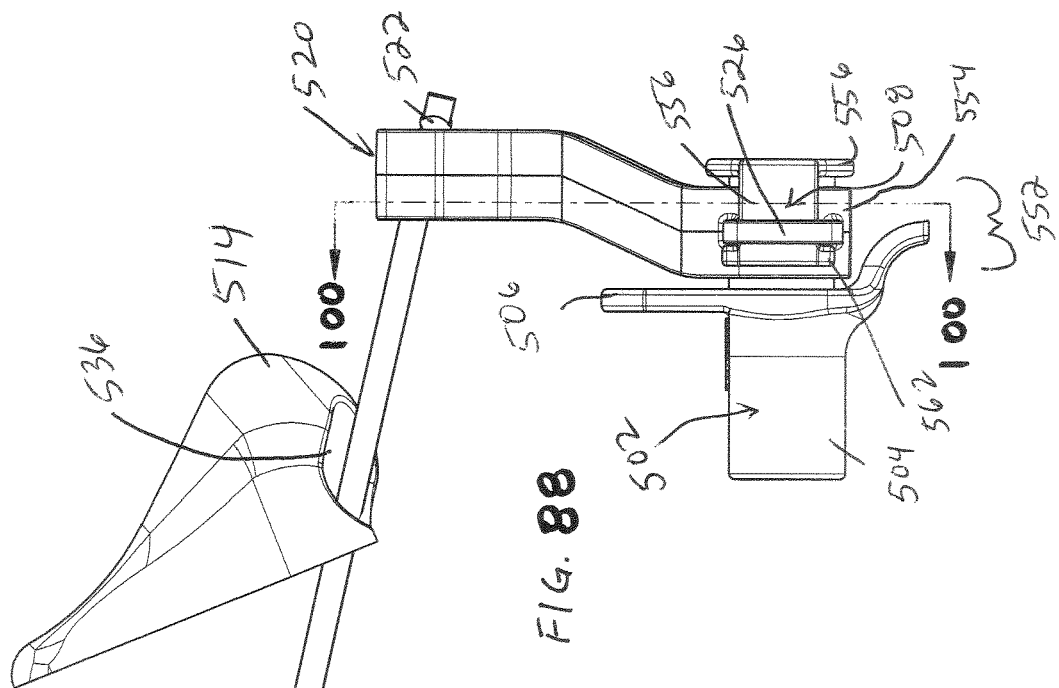
Figure 87:
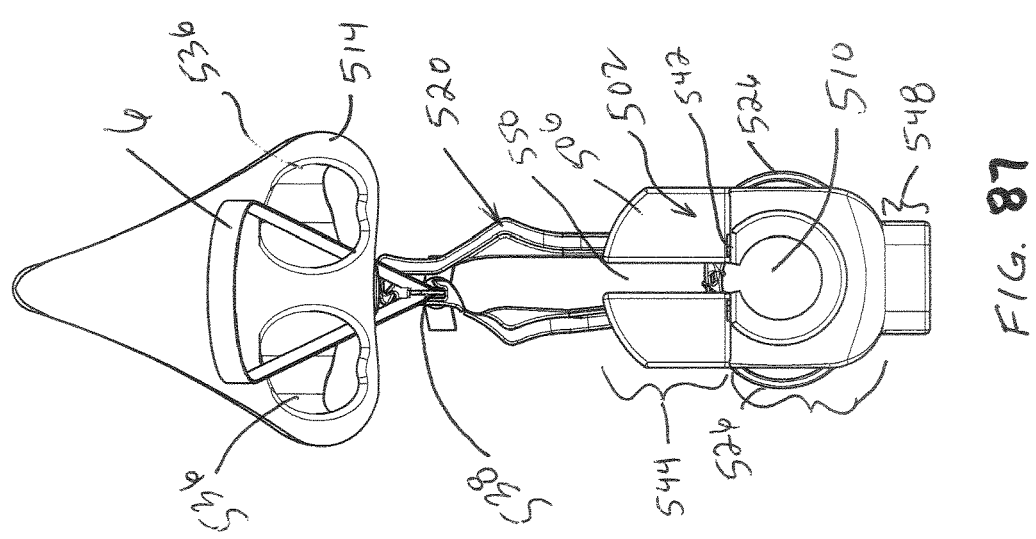
Figure 109:
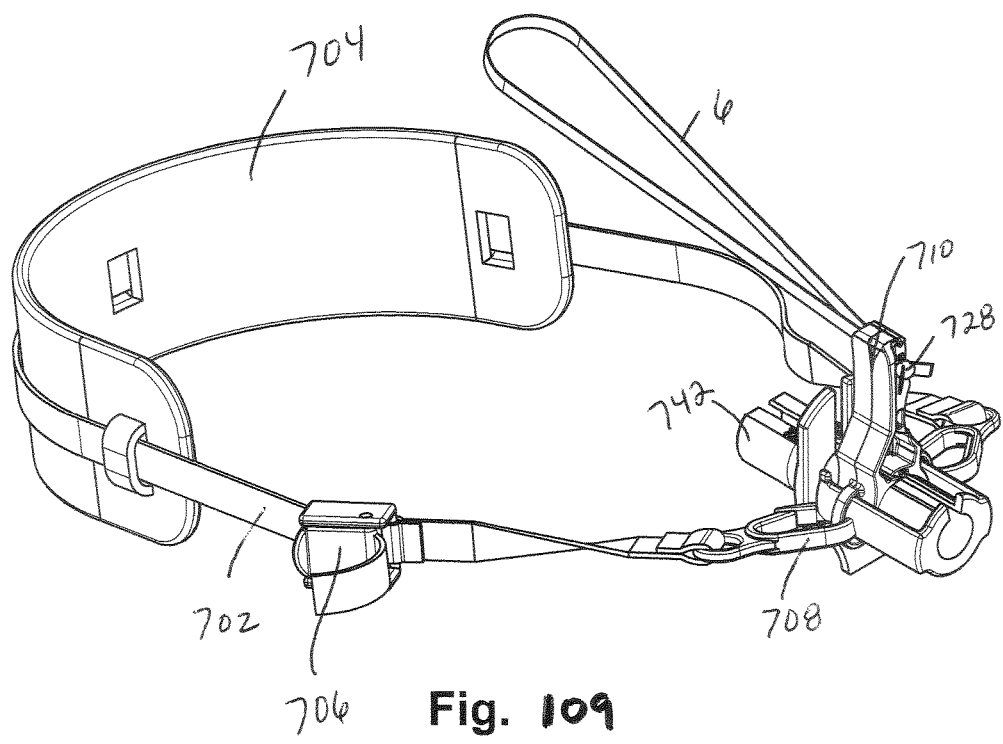
Figure 110:
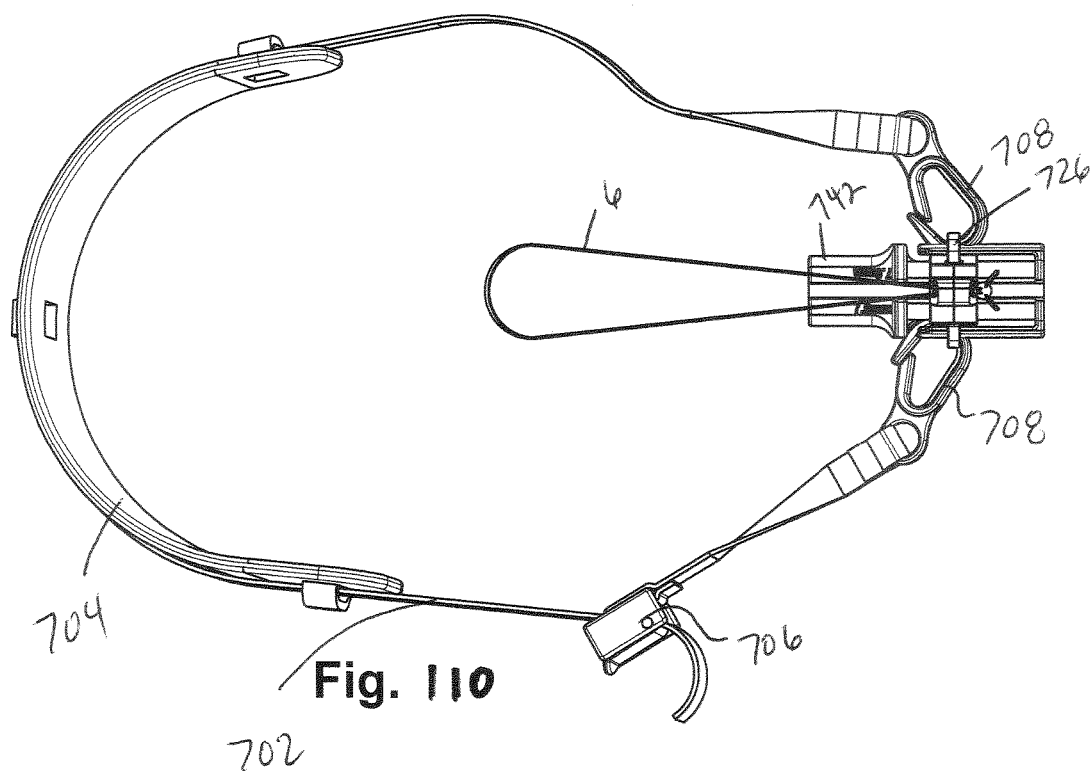
Figure 111:
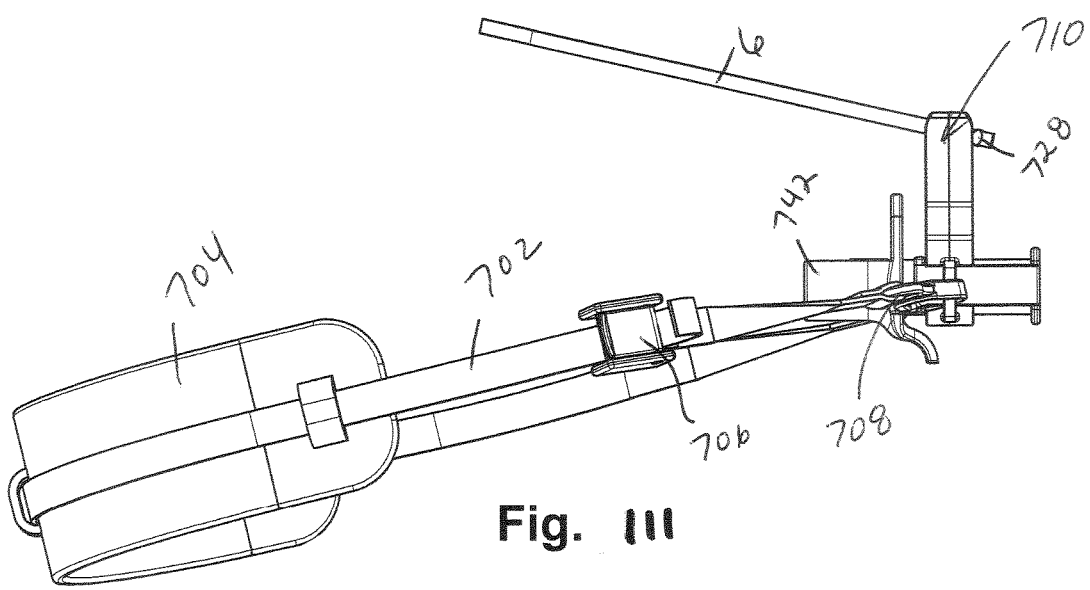
Figure 112:
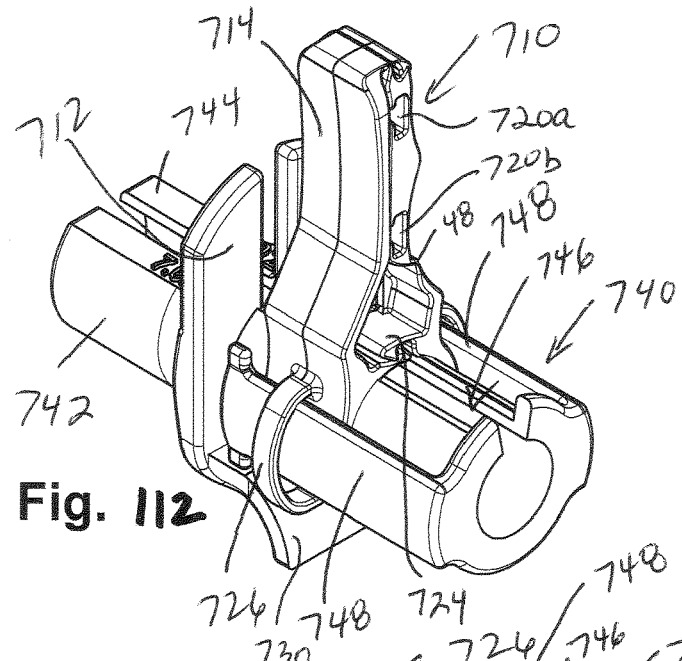

FIG. 67 is a bottom view of the endotracheal tube retention system of FIG. 62;

FIG. 68 is a cross-sectional side view of the endotracheal tube retention system of FIG. 67, taken along line 68-68;

FIG. 69 is a front view of the endotracheal tube retention system of FIG. 62;

FIG. 70 is a side view of the endotracheal tube retention system of FIG. 62;

FIG. 71 is a rear view of the endotracheal tube retention system of FIG. 71;

FIG. 72 is a front perspective view of the endotracheal tube retention system of FIG. 62;

FIG. 73 is a partially exploded perspective view of yet another endotracheal tube retention system;

FIG. 74 is a perspective view of the endotracheal tube retention system of FIG. 73, with the various parts installed on an endotracheal tube;

FIG. 75 is another perspective view of the endotracheal tube retention system of FIG. 73;

FIG. 76 is a bottom view of the endotracheal tube retention system of FIG. 73;

FIG. 77 is a cross-sectional side view of the endotracheal tube retention system of FIG. 76, taken at line 77-77;

FIG. 78 is a front view of the endotracheal tube retention system of FIG. 73;

FIG. 79 is a left side view of the endotracheal tube retention system of FIG. 73;

FIG. 80 is a rear view of the endotracheal tube retention system of FIG. 73;

FIG. 81 is a cross-sectional side view of a human head showing placement of an endotracheal tube in the mouth and throat of a patient, with yet another example endotracheal tube retention system installed in the nasal cavity and mouth of a user;

FIG. 82 is a perspective view of the example endotracheal tube retention system of FIG. 81, including the addition of a neck strap;

FIG. 83 is a perspective view of the example endotracheal tube retention system of FIG. 81 in a closed configuration, showing the placement of the system relative to a patient's nose, but without showing the endotracheal tube;

FIG. 84 is a perspective view of one of the components of the endotracheal tube retention system of FIG. 81;

FIG. 85 is a perspective view of one of the components of the endotracheal tube retention system of FIG. 81;

FIG. 86 is a perspective view of one of the components of the endotracheal tube retention system of FIG. 81, shown in an open configuration;

FIG. 87 is a front view of the endotracheal tube retention system of FIG. 81, shown installed in the nose/nasal cavity of a patient;

FIG. 88 is a side view of the endotracheal tube retention system of FIG. 87, shown installed in a nose/nasal cavity of a patient;

FIG. 89 is a front perspective view of the bite block and nesting device of the example endotracheal system shown in FIG. 82;

FIG. 90 is a side view of the bite block and nesting device of FIG. 89;

FIG. 91 is a front view of the bite block and nesting device of FIG. 89;

FIG. 92 is a perspective view of a clip utilized with the endotracheal tube retention system of FIG. 82, shown in an open position;

FIG. 93 is a front or rear view of the clip of FIG. 92;

FIG. 94 is a side view of the clip of FIG. 92;

FIG. 95 is a top view of the endotracheal tube retention system shown in FIG. 82, with the clip installed on the bite block/nest and shown with the clip in an open position;

FIG. 96 is a front view of the endotracheal tube retention system of FIG. 95;

FIG. 97 is a rear perspective view of the endotracheal tube retention system of FIG. 95;

FIG. 98 is a side view of the endotracheal tube retention system of FIG. 95;

FIG. 99 is a rear view of the endotracheal tube retention system of FIG. 95;

FIG. 100 is a cross-sectional rear view of the endotracheal tube retention system of FIG. 82, taken at line 100-100 in FIG. 88, with the clip in a closed position;

FIG. 101 is a left rear perspective view of an alternative example bite block/nest for an endotracheal tube retention system;

FIG. 102 is a top view of the bite block/nest of FIG. 101;

FIG. 103 is a right rear perspective view of the bite block/nest of FIG. 101;

FIG. 104 is a right side view of the bite block/nest of FIG. 101;

FIG. 105 is a rear view of the bite block/nest of FIG. 101;

FIG. 106 is a left side view of the bite block/nest of FIG. 101;

FIG. 107 is a bottom view of the bite block/nest of FIG. 101;

FIG. 108 is a bottom perspective view of the bite block/nest of FIG. 101;

FIG. 109 is a perspective view of an alternative example endotracheal tube retention system;

FIG. 110 is a top view of the endotracheal tube retention system of FIG. 109;

FIG. 111 is a side view of the endotracheal tube retention system of FIG. 109;

FIG. 112 is a rear perspective view of the endotracheal tube retention system of FIG. 109, without the neck strap, which is optional.

Figure 113:
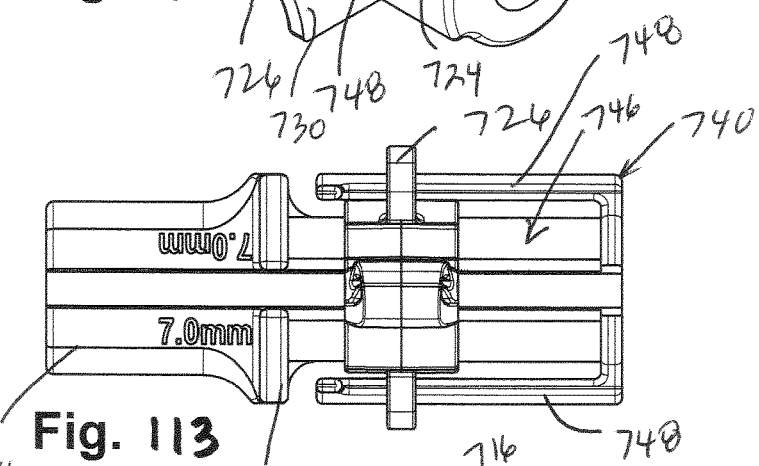
Figure 114:
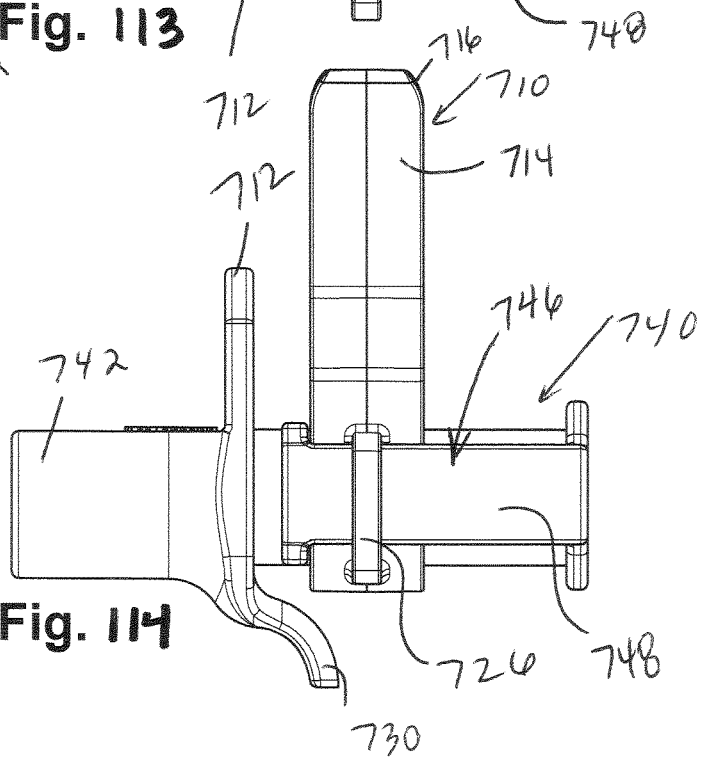
Figure 115:
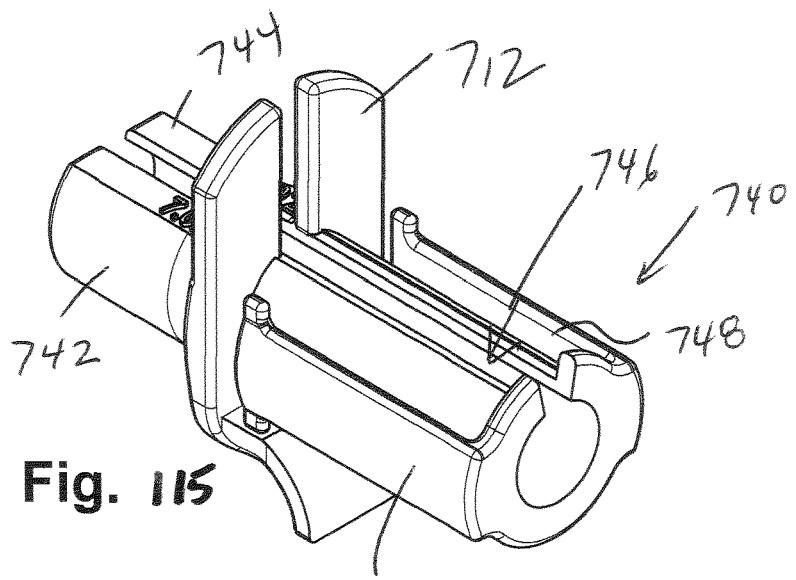
Figure 116:
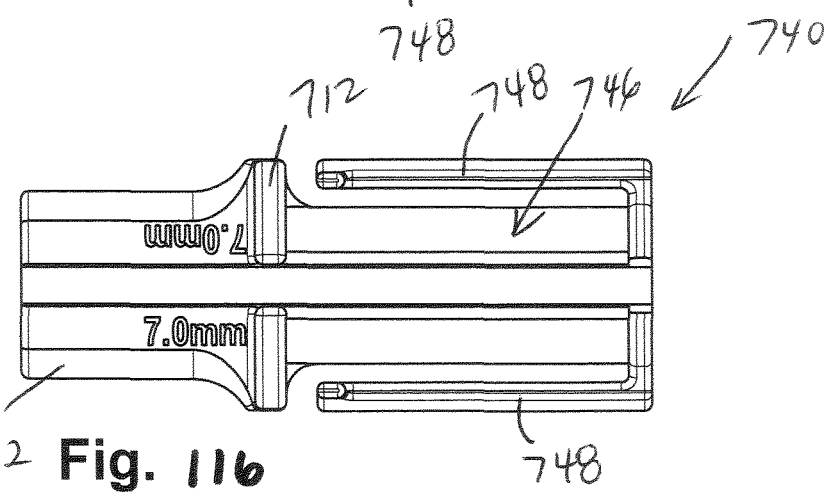
Figure 117:
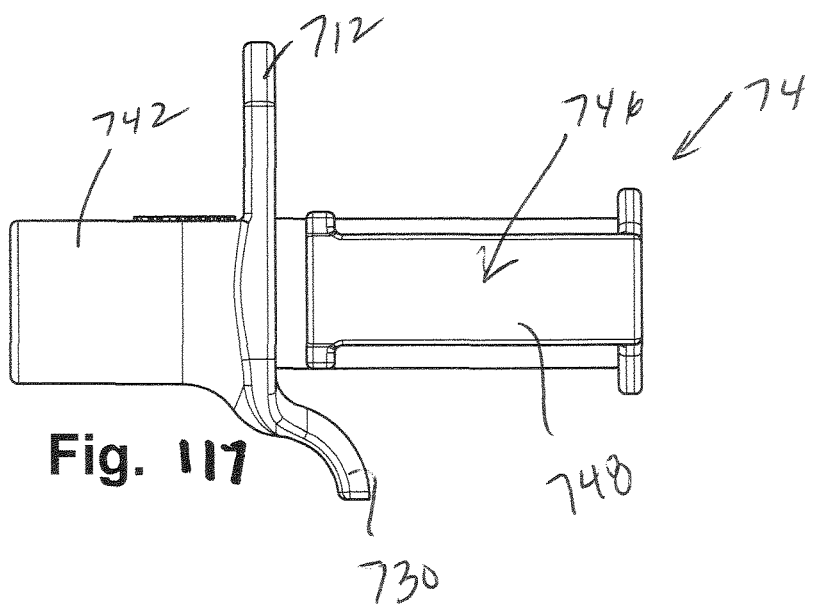
Figure 118:
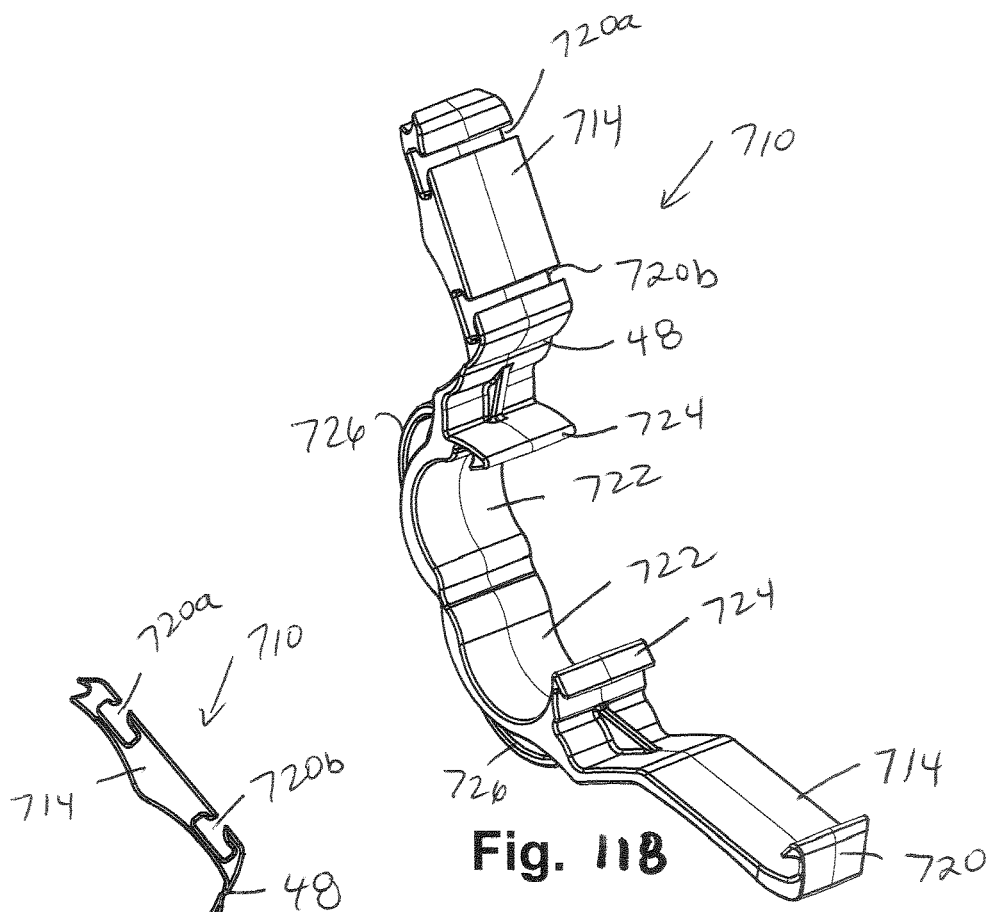
Figure 119:
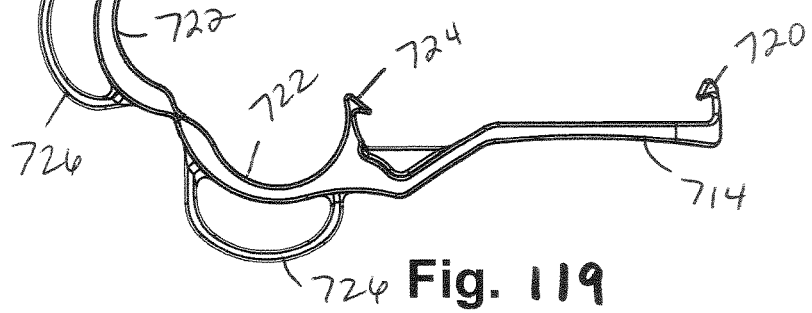
Figure 120:
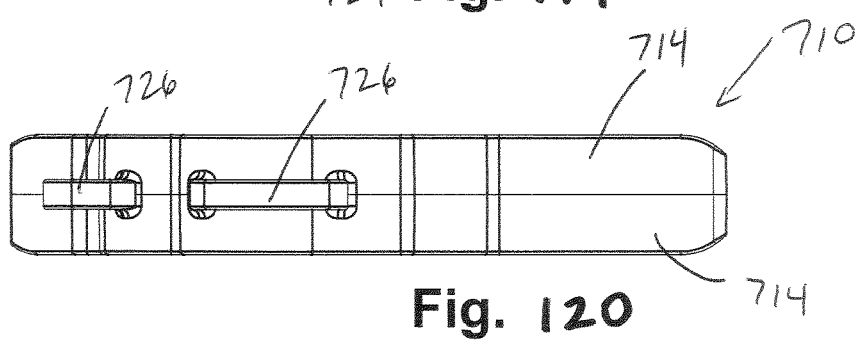

FIG. 113 is a top view of the endotracheal tube retention system of FIG. 112;

FIG. 114 is a side view of the endotracheal tube retention system of FIG. 112;

FIG. 115 is a rear perspective view of the bite block/nest of FIG. 112;

FIG. 116 is a top view of the bite block/nest of FIG. 112;

FIG. 117 is a side view of the bite block/nest of FIG. 112;

FIG. 118 is a perspective view of the clip of FIG. 112, shown in an open position;

FIG. 119 is a front or rear view of the clip of FIG. 118, shown in an open position; and FIG. 120 is a side view of the clip of FIG. 118.

DETAILED DESCRIPTION

The technology described herein relates generally to a system 20 for holding an endotracheal tube 22 or other member in suspension over a patient's face relative to an orifice of a patient's face, such as the mouth 18 or nose 10. A nasal bridle 6, as discussed above in the Background, has been previously used to secure a feeding tube in a nose 10 of a patient, but has not been used to secure an endotracheal tube 22. Moreover, the examples described herein help to suspend the bridle 6 above a patient's face so that the bridle does not irritate a patient's skin or otherwise impact a patient's recovery.

The nasal bridle 6 assists in retaining a tube 22 in position because it extends through one of the patient's nostrils 8, 16, around the vomer bone, and then out the other nostril 16, 8 of the patient 24. It is then secured to the tube 22 that is positioned in the orifice. When a patient 24 attempts to pull on the tube 22 to remove it from their mouth 18, nose 10 or other orifice, the patient 24 feels pressure on the vomer bone in their nasal cavity, which can cause discomfort or pain. As a result, a patient 24 will typically stop pulling on the bridle 6 or tube 22 in order to avoid further discomfort. Even if the patient 24 continues to pull on the bridle 6 or tube 22 to the point where they cause themselves discomfort, it is difficult to remove the bridle 6 and the associated tube 22 because the bridle 6 does not easily tear or break. Thus, the bridle 6 is useful in retaining a device in an orifice on the face or in the vicinity of the face of a patient 24. Thus, the examples described herein relate to a retention system 20 for retaining a device in an orifice on the face of a patient 24, but the technology described herein could also be used for any type of device that is positioned on or in the face of a patient 24, or in the vicinity of the nose 10.

One medical area where the technology described herein is useful is for retaining endotracheal tubes 22 in the mouth 18 of a patient 24. As discussed above, retention of an endotracheal tube 22 is very important to the health of a patient 24 because it provides a constant supply of oxygen to a patient's lungs. Advantages of the example retention system 20 include the use of a minimalistic design when compared to other devices that are presently marketed for endotracheal tube anchoring. The system 20 allows the endotracheal tube 22 to be moved from side-to-side, which provides easy access for oral care. Oral care is important for the overall health of the intubated patient 24. The system 20 does not utilize adhesive tape or other adhesives and does not use "stabilizers" that rest against a patient's face. The system 20 can be safely used with burn victims. Because of the design, the system 20 provides "negative feedback" to a patient (e.g., pain or discomfort) if the patient 24 pulls on the endotracheal tube 22, thus discouraging self-extubation. The system 20 has other advantages such as automatically marking the depth of the endotracheal tube 22, which allows healthcare professionals to easily monitor endotracheal tube 22 migration. The system 20 can be placed quickly (within a minute) after the endotracheal tube 22 is placed. The system 20 works for both adults and pediatric patients 24.

Several different examples of an endotracheal tube retention system 20 are described herein. In a first example, a floating clip 30, 90 surrounds the endotracheal tube 22 and is movable on the tube 22. In a second example, the clip 120 is immovable and is clamped to the endotracheal tube 22. Both examples allow access to a patient's mouth 18 for oral care and both are retained by a flexible member 2, 6 that is positioned around the patient's vomer bone in the nasal cavity.

Referring to FIGS. 1-8, a first example endotracheal tube retention system 20 is depicted. This example system 20 includes a floating clip 30, a strap or zip tie 34 positioned around the endotracheal tube 22, and a flexible member 2, 6 that is positioned behind a patient's nasal cavity and that extends out through the patient's nares 8, 16, where it can be coupled to the floating clip 30 via a connector 36. The zip tie or strap 34 is clamped to the endotracheal tube 22 so that it is substantially immovable and is positioned outside of the mouth 18 of the patient 24. The floating clip 30 is positioned opposite the strap 34 and includes a clip having a first clip part 38 and a second clip part 40 that surrounds the endotracheal tube 22 and at least part of the strap 34. The floating clip 30 has an inner contour 42 that allows it to move away from the strap 34 and mouth 18 of the patient 24, but cannot pass the strap 34 in a direction toward the mouth 18. Thus, the floating clip 30 is movable relative to the mouth 18 of the patient 24, but is not movable into the mouth 18 of the patient 24.

The floating clip 30 has a connection portion or connector 36 that is positioned on a top surface of the floating clip 30 and that is configured to couple with the flexible member 6 that extends from the patient's nares 8, 16. Another connector 44 may be positioned on a bottom surface of the clip 30 and can be coupled to a cord or strap 46 that extends around a patient's neck to maintain the clip 30 in relatively close proximity to the mouth 18. In addition, the cord 46 can serve as a safeguard to deter removal of the endotracheal tube 22 from the patient's airway in the unlikely event that the flexible member 6 is removed from the nasal cavity. For discussion purposes, the surfaces of the clip 30 are defined in terms of their relative position when a patient 24 is lying in a supine position.

Figure 1:
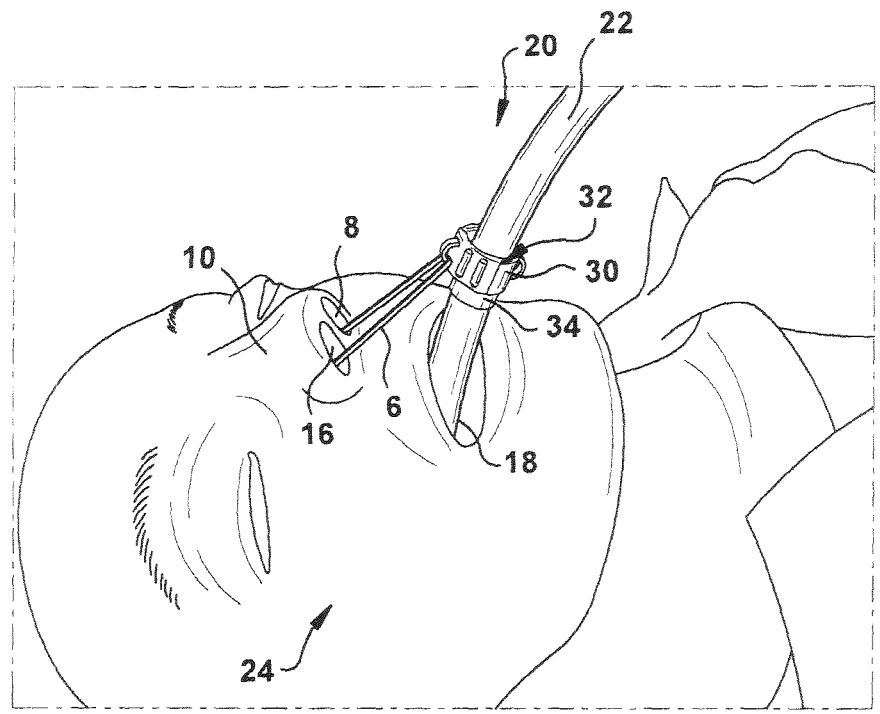
FIG. 1 is side perspective view of an example endotracheal tube retention system in use with a patient in a supine position.

FIG. 1 shows an endotracheal tube 22 inserted into the mouth 18 of a patient 24, with the floating clip 30 and strap 34 positioned around the endotracheal tube 22 and the flexible member 6 positioned behind the nasal cavity inside the patient's head. (See also FIG. 8I). The flexible member 6 extends through the connection portion 36 that is positioned on the top of the floating clip 30 and a knot is tied in the flexible member 6 to couple the two ends of the flexible member 6 together. The flexible member 6, shown in FIG. 1, is an umbilical tape 6. The flexible member 6 may be other types of materials and structures, if desired. For example, the flexible member could be polymeric or polymer coated cords.

Figure 2:
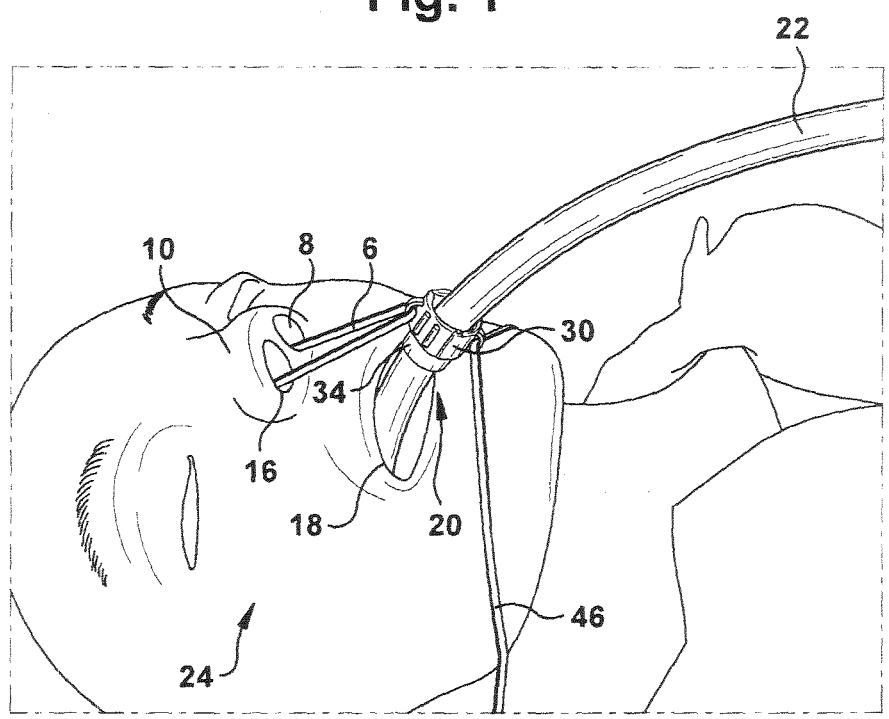
FIG. 2 is a side perspective view of an alternative example endotracheal tube retention system that further includes a strap that extends around a patient's neck, with the patient in a supine position.
Figure 3:
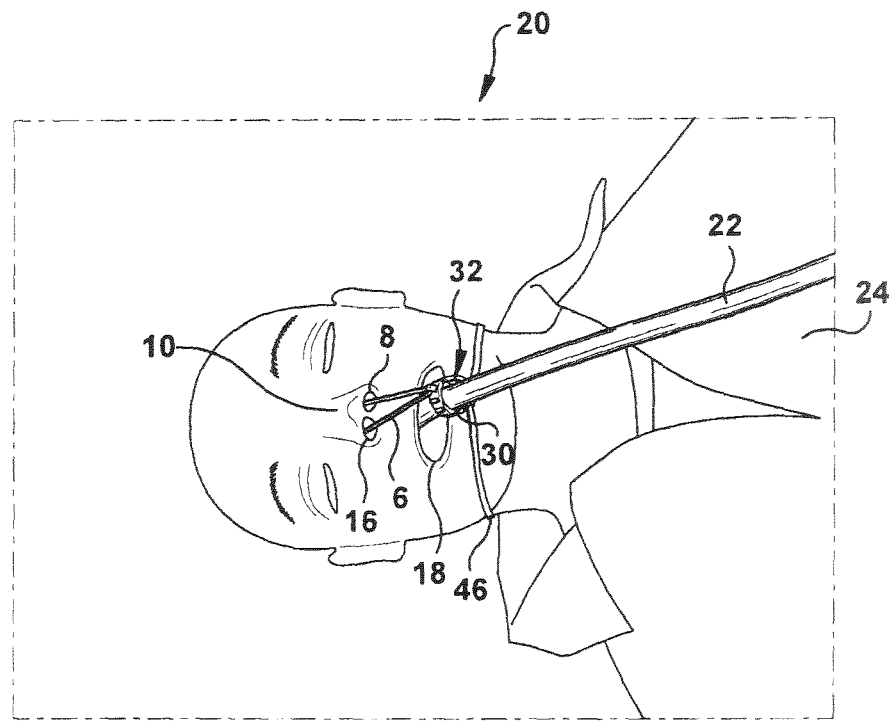
FIG. 3 is a top view of the example endotracheal tube retention system of FIG. 2.

FIG. 2 is similar to FIG. 1, but also shows the cord 46 that forms a loop around the back of the neck of the user. The cord 46 extends through the connection portion 44 that is formed on the bottom of the clip 30 and the two ends of the cord 46 may be tied or otherwise clipped together in order to couple the cord 46 to the floating clip 30. In addition to serving as a back up to the flexible member 6, the cord 46 can help to limit the movement of the floating clip 30 away from the patient's mouth 18. FIG. 3 is a top view of the endotracheal system 20 installed in a patient's head.

Figure 4:
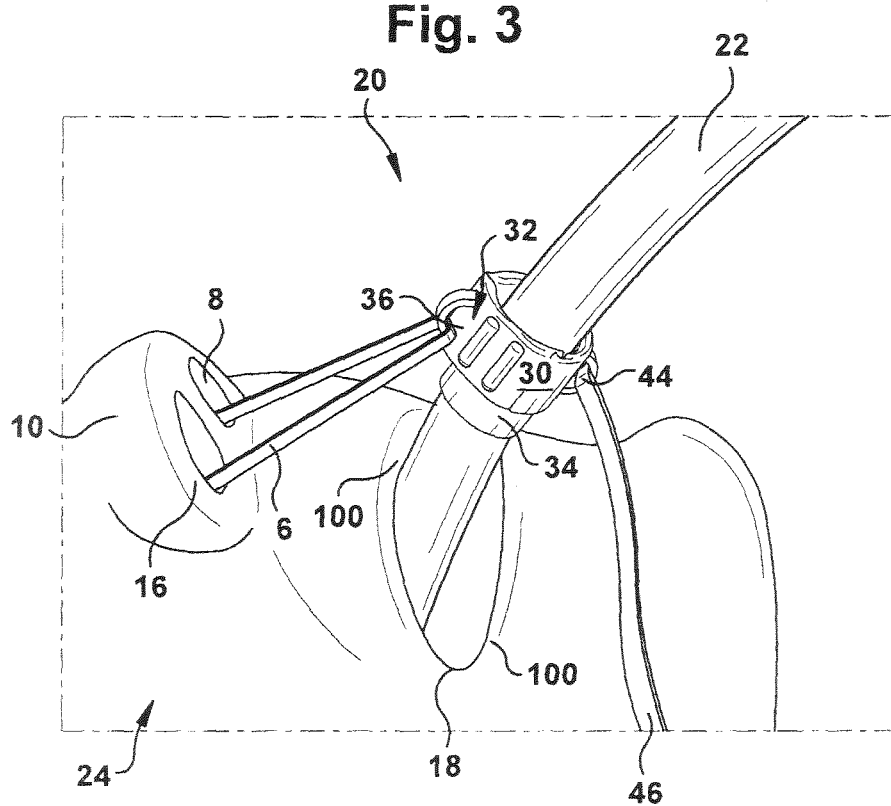
FIG. 4 is an enlarged side view of the endotracheal tube retention system of FIG. 2.
Figure 5:
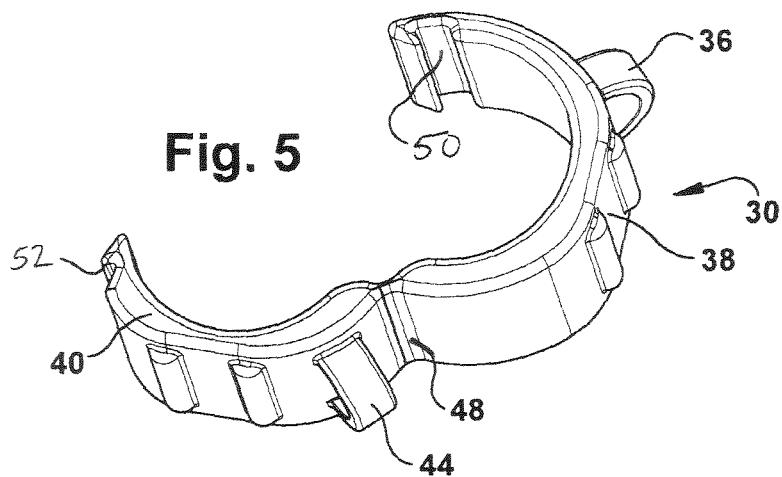
FIG. 5 is a perspective view of an example clip for use with the example endotracheal tube retention system of FIGS. 1-4 in an open position.
Figure 6:
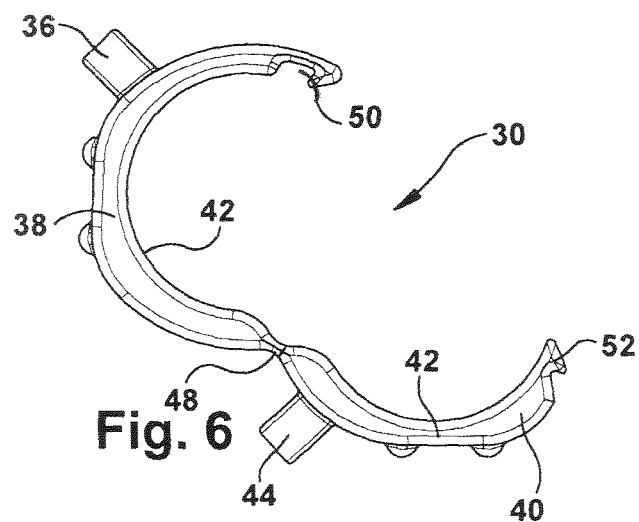
FIG. 6 is a front view of the example clip of FIG. 5 in an open position.
Figure 7:
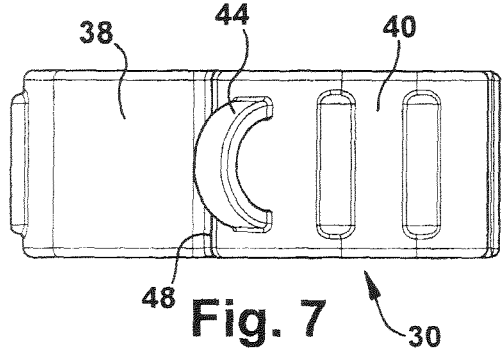
FIG. 7 is a left side view of the example clip of FIG. 5 in a closed position.
Figure 8:
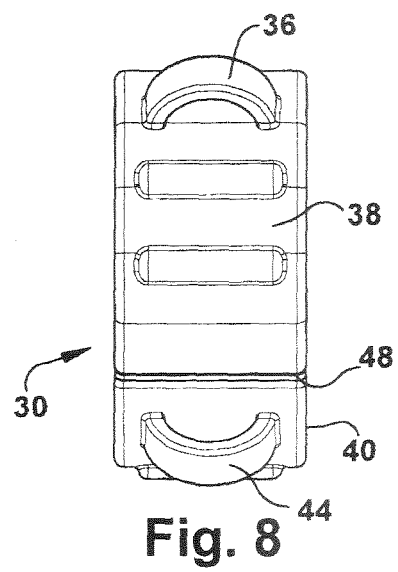
FIG. 8 is a right side view of the example clip of FIG. 5 in a closed position.

FIG. 4 is a close up view similar to FIG. 2. As is evident from FIG. 4, the flexible member 6 is elevated or suspended above the face and lips 100 of the patient 24. This helps to deter irritation of the patient's skin, among other benefits. In addition, movement of the floating clip 30 toward the mouth 18 of the patient 24 is prevented by the zip tie 34, which is clamped to the endotracheal tube 22.

FIGS. 5-8 show various views of the floating clip 30 according to the example endotracheal tube retention system 20. The floating clip 30 has a first part 38 and a second part 40 that are hinged together by a living hinge 48. Other types of hinges may alternatively be use. The first and second parts 38, 40 have an inner contour 42 that is curved or circular in order to permit ease of movement along the length of the endotracheal tube 22. A clasp or fastening member 50, 52 is associated with each free end of the first and second parts 38, 40. A top connecting portion 36 is associated with the first part 38 of the clip 30 and a bottom connecting portion 44 is associated with the second part 40 of the clip 30. As explained above, the top connecting portion 36 is utilized to couple the floating clip 30 to a flexible member 6 that extends from a patient's nose. The bottom connector 44 is used to couple with a cord 46 that extends around the back of a patient's neck. The clasp shown includes a hook 52 and groove 50. The hook 52 of the second part 40 clips into the groove 50 of the first part 38 in order to join the free ends of the first and second parts 38, 40 together when the floating clip 30 is positioned around an endotracheal tube 22. A hook is positioned adjacent the groove 50 so that the hook 52 catches in the groove 50. The floating clip 30 may be made using an injection molding process and is preferably formed of a polymeric material, such as polypropylene. Other manufacturing processes and materials may be used, as known by those of skill in the art.

FIG. 11 shows a conventional cable or zip tie 34 that is used in conjunction with the floating clip 30. The zip tie 34 is positioned around the endotracheal tube 22 at a desired position relative to the mouth 18 of the patient 24. When the zip tie 34 is initially placed on the tube, a measurement of the distance between the zip tie 34 and the mouth may be taken in order to later judge whether the tube has migrated. The floating clip 30 is positioned downstream from the zip tie 34 so that the zip tie 34 blocks movement of the floating clip 30 toward the mouth 18. The zip tie 34 is trimmed after it has been installed around the endotracheal tube 22. The floating clip 30 has an inner dimension D1 that is greater than the outer dimension D2 of the endotracheal tube 22, but smaller than the outer dimension D3 of the zip tie 34 when the zip tie 34 is installed on the endotracheal tube 22. The nub 56 on the zip tie 34 also helps to deter movement of the floating clip 30 towards the mouth 18 of the patient 24. The zip tie 34 may be made of any desirable material, such as nylon, polypropylene, PEEK, or other materials as known by those of skill in the art.

FIGS. 9 and 10 depict a bridle installation system that is used to install the flexible member 6 behind the vomer bone in a patient's nasal cavity. FIG. 9 depicts a flexible member 2 that has a magnet 4 attached to one end of the polymeric flexible member 2. The polymeric flexible member 2 is hollow and a stiffener 12 is inserted into the hollow interior of the polymeric flexible member 2 in order to allow the flexible member 2 to be inserted into the patient's nasal cavity. An umbilical tape 6 is attached to and part of the flexible member 2. The umbilical tape 6 is attached to the polymeric flexible member 2. The flexible member 2 is inserted into a first naris 8 of a patient's nose 10.

FIG. 10 depicts a retrieving member 14 that has a magnet 4 at the leading end of the retrieving member 14. The retrieving member 14 is stiffer than the flexible member 2 in order to allow insertion into the nasal cavity of a patient 24 via the nares 8, 16. The trailing end of the retrieving member 14 has an enlarged portion 26 in order to prevent over inserting the retrieving member 14 into the patient's nose 10.

For installation, the stiffening member 12 is inserted into the hollow cavity of the flexible member 2 and the flexible member 2 is inserted into a first naris 8 of a patient's nose 10 until the magnetic end 4 of the flexible member 2 is positioned behind the vomer bone of the patient 24. Then the magnetic end 4 of the retrieving member 14 is inserted into the second naris 16. As the magnetic end 4 of the retrieving member 14 reaches the vomer bone, it is attracted to the magnet 4 on the flexible member 2 until the magnets 4 on each device 2, 14 meet and attach to one another. The stiffening device 12 is then removed from the flexible member 2 and the retrieving member 14 is pulled from the second naris 16. Because the two magnets 4 are coupled together, as the retrieving member 14 is pulled from the second naris 16, the flexible member 2 bends around the vomer bone and is pulled from the nasal cavity with the retrieving member 14. The polymeric portion 2 of the flexible member may be completely removed from the nasal cavity until the umbilical tape 6 is all that remains in the cavity. Then the polymeric portion 2 can be cut from the umbilical tape 6 portion. A first end of the umbilical tape 6 extends from the second naris 16 of the nose 10 and a second end of the umbilical tape 6 extends from the first naris 8 of the nose 10. The ends of the umbilical tape 6 can be tied together around the clip 30, as discussed above.

FIG. 12 depicts an optional neck strap 58 that can be coupled to the bottom connector 44 of the floating clip 30. The neck strap 58 can be used instead of the cord 46 that was shown tied around the neck in FIGS. 2-4. As shown, the neck strap 58 can have a wide cushioned rear portion 60 that goes around the back of the neck and a first strap 62 that goes around the front of the neck. A thinner second or other strap 64 can be used to couple the neck strap 58 to the bottom connector 44. The neck strap 58 can be adjustable via a sliding fastener 66 or other means. The thinner strap 64 may also be adjustable via a sliding fastener 66 or other means. The first strap 62 is designed to be retained around the neck and the thinner strap 64 is designed to be adjustable in order to properly fit different sizes of patients 24. Both the first strap 62 and the second strap 64 can be elastomeric or non-stretchy or a combination thereof.

FIGS. 13-15 depict an adjustable strap 68 that may be positioned around an endotracheal tube 22 in order to deter movement of the floating clip 90 toward the mouth 18 of the patient 24. The adjustable strap 68 may be used instead of or in addition to the zip tie 34. The zip tie 34 is generally destroyed upon removal, but the adjustable strap 68 is removable and replaceable on the endotracheal tube 22. When placing the strap 68 on the endotracheal tube 22, it should be pulled tight so that the strap 68 is substantially fixed in position upon the exertion of a force that is normal under the circumstances.

The adjustable strap 68 is generally flat and thin and includes a post 70 at an enlarged end 72 thereof, and holes 74 are spaced along the length of the strap. The holes 74 are used for mating with the post 70 when the strap 68 is installed around an endotracheal tube 22 in order to pull the strap 68 tight around the tube 22. While four holes are shown, a different number of holes can be utilized and is a function of the length of the strap 68 and the size of the post 70. When the post 70 is installed into one of the holes 74 on the strap 68, a portion of the strap 68 will wrap around and overlap the post and part of itself. This is shown best in FIG. 25.

The strap 68 has an enlarged flattened portion 72 near the post 70. This enlarged portion 72, along with the post 70, serve as guides for the floating clip 90 on the strap 68 in order to permit the strap 68 to mate properly with the floating clip 90. The enlarged flattened portion 72 will extend across at least part of the width of the floating clip 90 when the floating clip 90 is positioned on the strap 68 and extend out the other side. The post 70 will align with the inner contour of the floating clip 90, as will be discussed in greater detail in connection with FIGS. 21-26. The holes 74 on the strap 68 have raised edges 76 in order to assist the post 70 in entering the holes 74. In addition, the post 70 has a tapered portion 78 that has a larger diameter than a shaft portion 80 that is positioned between the flat portion of the strap 68 and the tapered portion 78, such that a lip 82 is provided at the base of the tapered portion 78. The tapered portion 78 of the post 70 assists the post 70 in entering the holes 74 and the shaft portion 80 and lip 82 help to trap the post 70 in the holes 74. Ridges 84 may be provided on the end of the strap 68 opposite the post 70 in order to provide a gripping portion for the installer's fingers so that the installer can more easily pull the strap 68 tight during installation on the endotracheal tube 22. The enlarged portion 72 may also provide a gripping area for the installer's fingers during installation of the strap 68 on the endotracheal tube 22.

FIGS. 16a-20 depict an alternative example floating clip 90 for use with the strap 68 of FIGS. 13-15. The alternative example floating clip 90 may also be used with a zip tie 34 instead of a strap 68, if desired. FIGS. 16a-16c depict three different sizes of floating clips 90. Since the size of the endotracheal tube 22 is a function of the size of the patient 24 and the patient's airway, different size endotracheal tubes 22 are utilized in different patients 24. As a result, different size clips 90 are needed since the diameter D3 of the strap 68, when installed on the endotracheal tube 22, will vary based upon the diameter D2 of the tube 22. Advantageously, a single size strap 68 can be utilized with different sized tubes 22 because the strap 68 is adjustable. FIGS. 16a-16c depict the floating clip 90 in an open position. If the clip 90 was installed on an endotracheal tube 22, this view would depict the front of the clip 90, e.g., the portion that is closest to the patient's mouth 18. As is evident, the floating clip 90 has a contoured interior 92 that is in general rounded, but that includes a ledge 94 against which the strap 68 seats. The ledge 94 is positioned at the rear of the floating clip 90 and provides a stop so that the floating clip 90 cannot pass the strap 68 and enter the patient's mouth 18.

The top of the clip 90 is the portion pictured at the top of FIGS. 16a-16c and includes an opening 98 through which the flexible member 6 can extend and be secured. A hinge 48 is provided at the top of the clip 90 in order to allow first and second parts 38, 40 of the clip 90 to move apart in order to surround an endotracheal tube 22. The bottom of the clip 90 includes a clasp or fastening element 50, 52 on each end of the first and second parts 38, 40 of the clip 90. The fastening element is shown best in FIGS. 18 and 19 and may include a hook 52 and a groove 50, with the hook 52 seating in the groove 50 in order to hold the clip 90 closed. Other fastener and fastening types may be used.

FIGS. 17-20 show alternative views of the clip 90 in an opened position. FIGS. 18 and 19 show the front and back of the floating clip 90, respectively, and FIG. 20 shows a side view of the clip 90, with the hinge 48 being positioned about ¼ of the height of the clip 90 from the bottom of the clip 90. As is evident from FIG. 18, the floating clip 90 has an internal ledge 94 for abutting the strap 68 that is positioned at the rear of the clip 90. In addition, the shape of the ledge 94 is designed to accommodate the shape of the strap 68 when a portion of the strap 68 overlaps itself, as is evident by the enlarged ledge area 104 near the top of the ledge 94 on each of the first and second parts 38, 40 of the clip 90. As discussed above, a living hinge 48 is positioned between the first and second parts 38, 40 of the clip 90. Other types of hinges may alternatively be used.

The connection portion 98 is provided at the top of the clip 90 where the first and second parts 38, 40 of the clip 90 meet. The flexible member 6 may be secured to the clip 90 at the connection portion 98. The connection portion 98 is an opening that is provided between the first and second parts 38, 40 when the first and second parts 38, 40 are fastened together around the endotracheal tube 22.

Since the clip 90 is designed to float on the endotracheal tube 22, the inner contour 92 of the first and second parts 38, 40 of the clip 90 should have a greater diameter D1 than both the diameter D2 of the endotracheal tube 22 and the diameter D3 of the strap 68 so that the clip 90 may float on the tube 22 and strap 68. The ledge 94 at the rear of the floating clip 90 will prevent the clip 90 from entering the mouth 18 of the patient 24. While a bottom connector 44 is not shown for attaching to a neck strap 46, 58, a bottom connector 44 could be provided. Alternatively, a neck strap 46, 58 could be coupled to a connection portion 36 on the clip 90. The connection portion 98 could be at the top of the clip 90 or elsewhere.

FIGS. 21-26 depict the floating clip 90 installed around the strap 68. As previously mentioned, the strap 68 includes self-aligning portions 72 in the form of the tab or enlarged end 72 that extends out from the flat portion at the post end of the strap 68 and the post 70, as is evident in FIG. 21 and the top view of FIG. 23. The tab 72 has a tapered shape and when the floating clip 90 begins to seat on the strap 68, the tapered shape 72 helps to guide the clip 90 onto the strap 68 so that the overlapping portion 106 and post 70 of the strap 68 seat within the enlarged portion of the ledge area 104, directly below the connection portion 98 and opposite the clasp 50, 52, as shown best in FIGS. 25-26. The interior diameter D1 of the ledge 94 is less than the outer diameter D3 of the strap 68 when the strap 68 is installed on the endotracheal tube 22.

While FIGS. 16-26 depict a floating clip 90, the clip could be a stationary clip 120. For a stationary clip 120, the internal diameter 92 of the floating clip 90 would be smaller than a diameter of the strap 68 such that the strap 68 is compressed against the tube 22 when the clip 120 is fastened closed. If the clip 120 compresses the strap 68, it will be substantially fixed in position with the strap 68.

In the example of FIGS. 16-26, the clip 90 has an elongated body formed by the first and second parts 38, 40 of the clip 90 so that the connection portion 98 is spaced from the endotracheal tube 22. This is beneficial because it provides for the flexible member 6 to be suspended over the tube 22. By suspending the flexible member 6 over the tube 22, the flexible member 6 will generally be raised above the face and lips 100 of the patient 24. This will help to deter any irritation that would normally be caused by the association of the flexible member 6 with the patient's skin. As will be readily evident to those of skill in the art, other shapes may be used for the clip 90. For example, a separate connection portion 36 could be coupled to the exterior of the clip 90 instead of being formed between the two clip parts 38, 40. The clip 90 could be round and have an extension that provides the connection point 36. The clip could be elongated and tape could be used to couple the umbilical tape to the clip. Any number of other shapes could be utilized, the invention not being limited to the exact shape shown.

FIGS. 27-29 depict example steps involved in installing the system of FIGS. 16a-26. In FIG. 27, the endotracheal tube 22 is installed in a patient's airway and then the strap 68 is positioned around the endotracheal tube 22 in a position that is spaced from the lips 100. Then the flexible member/bridle 2, 6 is installed behind a patient's vomer bone in the nasal cavity such that both ends of the flexible member 6 extend from the patient's nose 10. Thereafter, the flexible member 6 is connected to the connection portion 98 of the clip 90. The clip 90 is positioned over the strap 68 on the endotracheal tube 22. The hinge portion 48 of the clip 90 is positioned upwardly so that the connection portion 98 is at the top of the clip 90 and spaced from the endotracheal tube 22. As is evident, the flexible member 6 remains elevated over the patient's face and lips 100. Other steps can be used in the installation, as desired.

FIGS. 30-34 depict an alternative example clip 90 that includes extensions 110 that help to deter the floating clip 90 from rotating or rocking toward the face of a patient 24 while on the endotracheal tube 22. The extensions 110 serve as stabilizers for the first and second parts 38, 40 of the floating clip 90. The extensions 110 are positioned on each of the first and second parts 38, 40 of the clip 90 opposite the hinge 48 and connection portion 98 of the clip 90. The internal diameter D1 of the extensions 110 is greater than the outer diameter D2 of the endotracheal tube 22, such that the extension portions 110 continue to permit the floating clip 90 to float.

FIGS. 35-44 depict an alternative example endotracheal tube retention system 20 where the clip 120 is stationary on the endotracheal tube 22. The stationary clip 120 is coupled to a first tubular portion or "nest" 122 that encircles a portion of the circumference of the tube 22 and is compressible so that the clip 120 can be clamped down upon the tubular portion 122 and held in a substantially immovable manner on the endotracheal tube 22, or nested on the endotracheal tube 22.

The clip 120 is depicted in FIGS. 35 and 36 and includes a first part 38 and a second part 40 that are joined together at a hinge 48, which is a living hinge, but could be other types of hinges. Both the first and the second parts 38, 40 of the clip 120 have a curved inner contour 126, 128, with a clasp 50, 52 at the free end of each part 38, 40. The clasp 50, 52, as shown, includes a hook 52 on the second part 40 and a groove 50 on the first part 38. The hook 52 mates with the groove 50 to hold the two parts 38, 40 together. A connection portion 98 is formed adjacent the hinge 48 between the first and second parts 38, 40 for coupling with a flexible member 6.

FIGS. 37 and 38 depict the tubular portion or nesting tube 122. The tubular portion 122 may be made from a soft elastomeric material. The nesting tube 122 has a slit 124 down the side so that the tubing 122 can be place over the endotracheal tube 22. When the nesting tube 122 is installed around the endotracheal tube 22, the slit 124 remains positioned adjacent the tube 22. The slit 124 will typically be positioned so that it is on the bottom of the endotracheal tube 22, but it could be positioned on the side. Referring again to FIG. 36, the first part 38 of the clip 120 includes a curved opening 126 that is larger than a curved opening 128 that is included on the second part 40 of the clip 120. This is in part due to the shape of the tubular nest portion 122, which has a slit 124 down the side which results in a longitudinal opening positioned adjacent the tube 22.

The clip 120 clamps down upon the tubular portion 122 in order to hold the tubular portion 122 in a substantially immovable position on the endotracheal tube 22, as shown in FIGS. 39-42. FIG. 39 shows how the clip 120 can be positioned so that the elongated portion of the clip 120 is positioned to the top of the endotracheal tube. The clip 120 has a length L1 that is less than the length L2 of the tubular portion 122 so that the clip 120 clamps down on the tubular portion 122 in the middle region thereof and part of the tubular portion 122 sticks out from each end of the clip 120. Again, as shown in FIG. 41, because the nesting tube 122 has a slit 124 on one side, the second part 40 of the clip 120 has a smaller inner radius than the first part 38 of the clip 120 so that the clip 120 may clamp down on all sides of the tubular portion 122. When the clip 120 is closed over the nesting tube 122, the tubing 122 is compressed and is substantially immovable. The clip 120 then holds the flexible member 6 away from the skin and provides retention to prevent inadvertent displacement or removal of the endotracheal tube 22.

FIG. 43 depicts a method of installing the endotracheal tube retention system 20 of FIGS. 35-42. In FIG. 43, the nesting tube 122 is installed around an endotracheal tube 22 with the slit 124 in the nesting tube 122 being positioned on the bottom. Then the flexible member 6 is threaded through the connection portion 98 that is formed between the first and second parts 38, 40 adjacent the hinge 48. The clip 120 is closed around the nesting tube 122 so that the fastening element 100 of the clip 120 is positioned near the slit 124 in the nesting tube 122. The flexible member 6 may be tied off after clip closure. As is evident from FIG. 44, the clip 120 design helps to maintain the flexible member 6 above the patient's face. In addition, the end of the nesting tube 122 serves as a buffer between the patient's face and the clip 120.

FIGS. 45-51 depict an alternative example endotracheal tube retention system 20 where the clip 120 is stationary on the endotracheal tube 22 and the tubular member includes a bumper portion 130 that is positioned adjacent the mouth 18 of the patient 24. The bumper portion 130 is axially coupled to the nesting tube 122, which is shown in FIGS. 45-47. The bumper portion 130 provides a first front portion that has a first diameter D4 and the nesting tube 122 provides a second rear portion that has a second diameter D5. The second diameter portion D5 is smaller in diameter than the first diameter portion D4, and a ledge 132 is provided between the first and second diameter portions D4, D5. The ledge 132 provides a surface against which the clip 120 may abut.

As shown in FIG. 50, the clip 120 has a first part 38 and a second part 40. The first and second parts 38, 40 may have a similar inner contour (not shown) or may have different inner contours 126, 128. The first and second parts 38, 40 of the clip 120 are coupled together by a living hinge 48 and a connection portion 98 is provided adjacent the living hinge 48 in order to couple to a flexible member 6. The clip 120 is positioned adjacent the bumper 130 and clamps down on the nesting tube 122. The bumper 130 serves as a mouth guard and provides additional protection to the patient's face and lips 100 in case the endotracheal tube 22 and resulting clip 120 and nest assembly 122 were to be displaced or pulled against the face. As with the prior example, the clip 120 compresses the nesting tube 122, but it does not compress the mouth guard/bumper portion 130. Thus, the mouth guard/bumper 130 remains between the patient's face and the hard plastic clip 120.

FIGS. 52-61 depict an alternative example of the endotracheal tube retention system 200. The design shown includes a bumper 202 that is mechanically attached to the clip 120 and the bumper 202 opens and closes with the clip 120, as shown in the drawings. The bumper 202 is designed to abut a patient's face in order to provide greater comfort to a patient. The bumper 202 rests against the nest tubing 204 when the clip 120 is in place on the endotracheal tube 22, but the bumper 202 is not connected to the nest tubing 204. The nest tubing 204 is shown best in FIGS. 52, 53, and 55 and may be similar to any of the nest tubing 204 depicted above in connection with other embodiments. The bumper 202 is attached to one of faces of one of the clip parts 38, but not to the other clip part 40, so the other clip part 40 is free to move relative to the bumper 202 and to the other clip part 38. The clip 120 may be positioned around the nest tubing 204 to hold the clip 120 in position on the tube 22. Alternatively, the nest tubing 204 may be excluded.

The clip 120 is similar to that shown in prior embodiments. The bumper 202 may be coupled to the clip part 38 in any known manner, such as via an adhesive. The bumper 202 has a substantial "C" shape, with the opening 214 of the "C" permitting entry of the endotracheal tube 22 therein. Once the endotracheal tube 22 is positioned inside the bumper 202 and clip 120 (and nesting tubing 204, if provided), the free arm 40 of the clip 120 can be moved downwardly until the connector's 206 at the end of the clip 120 couple together in order to encircle the endotracheal tube 22 and hold it in position in the clip 120. Prior to closing the clip 120, a knotted end of the bridle 6 should be installed in the closed end of the clip 120 (not shown). Once the clip 120 is closed, the knotted end of the bridle 6 is trapped in the opening 208 of the clip 120. FIGS. 55 and 56 show a position for the end of the clip when the clip is closed, such that the end of the clip is positioned to the side. In other embodiments, the end of the clip 120 could be positioned upwardly (not shown). The endotracheal tube 22 may be press fit into the clip 120 (and nest tubing 204, if included). Alternatively, the endotracheal tube 22 may float inside the clip 120 and bumper 202.

When the nest tubing 204 is used, the bumper 202 abuts an end of the nest tubing 204 and does not encircle the nest tubing 204. FIGS. 56-59 show how the nest tubing 204 interacts with the bumper 202 and clip 120. The clip 120 encircles the nest tubing 204 adjacent the bumper 202 and the endotracheal tube 22 extends through the nest tubing 204. The nest tubing 204 is preferably pliable and permits the clip 120 to press inwardly on the nest tubing 204 in order to trap the nest tubing 204 and the endotracheal tube 22 inside the clip 120. The connectors 206 on the clip 120 may be hooks that mate together. Any known type of connectors may be used.

FIG. 60 shows the clip 120 coupled to the bumper 202 with the clip 120 in an open position and showing the connectors 206 of the clip 120 as well as the opening 208 for receiving the knot of the bridle 6. The arms of the clip 38, 40 are connected at the closed end of the clip via a living hinge 48. FIG. 61 depicts how the system 200 couples together around an endotracheal tube 22. The nest tubing 204 is a cylindrical member that has a top part 210 of the cylinder removed so that a slot 212 is formed in the top part of the cylinder. First the neat tubing 204 is installed on the endotracheal tube 22 at a desired position of the tube 22 by sliding the endotracheal tube 22 into the slot 212 in the nest tubing 204. Then the opening 214 in the bumper 202 is slid over the endotracheal tube 22 and the circular inner portion 216 of the bumper 202 is positioned directly adjacent the end of the nest tubing 204. Since the clip 120 is mechanically coupled to the bumper 202, as the bumper 202 is slid onto the endotracheal tube 22, a cylindrical inner portion 216 of the clip 120 is positioned around part of the nest tubing 204. Once the bumper 202 and part of the clip 120 are installed on the nest tubing 204, a free end of a bridle 6 may be installed into the opening 208 in the end of the clip 120. The bridle 6 may be installed by positioning an enlarged portion of the bridle 6 through the opening 208 in the clip 120, such as a knot, or one arm of the bridle 6 can be threaded into the opening 208 and the other end can be tied to the part that extends through the opening 208. Then the other arm 40 of the clip 120 is closed down upon the nest tubing 204 until the hooks 206 at the end of the clip arms 38, 40 mate together.

FIGS. 62-72 depict another alternative example of the endotracheal tube retention system 300. The design shown incorporates a mouth guard/bumper 302 for the same purpose—to protect the mouth/lip area. However, the bumper 302 for this design is formed in two parts 314, 316 and each of the parts is attached directly to the arms 38, 40 of the clip. 120 The bumper 302 can serve as a guide for the nest tubing 304—the clip 120 is inserted onto the nest tubing 304 until the end of the tubing 304 contacts the bumper 302. In this example, the bumper 302 is in two parts 314, 316, and each part is mechanically attached to one side of the clip 38, 40. The clip 120 shown in the figures is not symmetrical. In particular, the clip 120 forms a cylindrical opening 318 for encasing the nest tubing 304 or endotracheal tube 22 and part of the cylindrical opening 318 is larger than the other part of the cylindrical opening 318. The bumper 302 is fitted to each arm 38, 40 based upon the length of the cylindrical opening such that one of the bumpers 314 is longer than the other bumper 316. As shown in FIGS. 62 and 63, hooks 306 at the end of the arms 38, 40 of the clip 120 extend past the ends of the bumper 302. These hooks 206 couple together when the clip 120 is closed around the nest tubing 304 or endotracheal tube 22 so that the ends of the bumper 314, 316 abut or nearly abut one another when the clip 120 is closed.

FIG. 64 depicts how the parts of the system are installed together. First the nest tubing 304, which is similar to the nest tubing 204 described in the prior embodiment, is installed around the endotracheal tube 22. Then the cylindrical opening 318 of the clip 120 is positioned around the nest tubing 304. Before the clip 120 is closed, a knotted end of the bridle 6 (not shown) may be installed through the opening 308 of the clip 120. Alternatively, after the clip 120 is closed, the bridle 6 can be threaded through the opening 308 in the clip 120. As the clip 120 is closed around the nest tubing 304, the bumper sections 314, 316 abut or nearly abut an end of the nest tubing 304 and the connectors 306 at the ends of the clips 38, 40 mate together.

FIGS. 65-72 depict the system 300 installed on an endotracheal tube 22. The bumper 302 abuts a patient's mouth. The bumper 302 closes around the tubing 304 so that a large gap is not present between the ends of the bumper sections 314, 316. The bumper sections 314, 316 may entirely close the gap, or a small gap may be present between the ends of the bumper sections 314, 316. The opening 318 in the clip 120 may be positioned at the top of the system 300, as shown in FIGS. 69-72, or could be positioned at the side, as with prior embodiments.

FIGS. 73-80 depict another alternative example of the endotracheal tube retention system 400. This design includes a one part bumper 402 that is not attached to the clip 120 or the nest tubing 404. The bumper 402 is a separate component that is placed onto the endotracheal tube 22 in front of the clip 120 and nest tubing 404. The bumper 402 still extends toward the mouth of the patient and the purpose is to protect the mouth/lip area. The bumper 402 is held in place due to a friction fit on its interior cylindrical surface 410 with the endotracheal tube 22.

In this example, the nest tubing 404 is used to surround the endotracheal tube 22 and the clip 120 is positioned around the nest tubing 404. The nest tubing 404 may be installed on the endotracheal tube 22 first and the clip 120 may be installed around the nest tubing 404. The bridle 6 knotted ends (not shown) may be extended through the opening 408 in the clip 120 before closing the clip 120, or the bridle 6 ends may be threaded through the opening 408. For example, one end of the bridle 6 may be threaded through the opening 408 while the other end is simply knotted to the end that is threaded through the opening 408, such that both ends do not need to be threaded through the opening 408 (not shown).

The bumper 402 in this example is circular and includes a circular inner opening 410 for surrounding the endotracheal tube 22. The opening 410 inside the bumper 402 is sized to fit tightly against an endotracheal tube 22. The bumper 402 has a slit 418 formed through the bumper 402 that permits the bumper 402 to slide over the endotracheal tube 22. The bumper 402 is made of a pliable material, such as a foam material, that permits the bumper 402 to be opened at the slit 418 in order to allow the bumper 402 to surround the endotracheal tube 22. Once the nest tubing 204 and clip 120 are installed around the endotracheal tube 22, the bumper 402 may be positioned around the endotracheal tube 22 at a position that is closer to the face of the patient than the clip 120. A small opening may be present in the slit portion of the bumper when it is installed. The opening 408 in the clip 120 extends upwardly past the outer edge of the bumper 402 in order to elevate the bridle 6 above the bumper 402. The opening 408 in the clip 120 may be positioned vertically above the endotracheal tubing 22 or it may be positioned to the left or right side of the endotracheal tubing 22. The clip 120 is similar to that described in prior embodiments and includes two hook-like connectors 406 at the ends thereof for coupling the clip 120 together.

For the mechanical attachment between the bumper and the clip 120, the bumper may be glued to the clip with an adhesive. The bumper may be molded or welded to the clip with ultrasonic welding. Any type of known attachment technique may be utilized. The bumper may be made of a closed cell foam and the nesting tube may be made of silicone or an elastomeric material such as SEBS (Styrene Ethylbutylene Styrene). Other types of compressible materials may be used instead of the nesting tube as long as the compressible materials help to retain the clip 120 in a fixed position on the endotracheal tube 22. Other types of polymeric or elastomeric materials may be used for the bumper as long as they are soft against a patient's skin. The bumper/nesting tube may be made of two different materials that are joined together, if desired, or of the same material.

Other types of devices may be clamped under the clip 30, 90, 120 of the present invention. For example, feeding tubes could be attached to the clip 30, 90, 120 and could be clamped at the same time that the endotracheal tube 22 is clamped by the clip 30, 90, 120. As long as flow through the feeding tube is not blocked, the clip 30, 90, 120 can clamp both tubes at the same time. Another type of tubing that could be clamped by the clip is an ET cuff line, or inflation cuff line. Thus, if a patient 24 requires both a feeding tube and an endotracheal tube 22, the example clip 30, 90, 120 described herein can be used for both and help to avoid the need for adhesive tape on the skin of the patient 24. Modifications may be made, if necessary, to cover different tubes.

FIG. 81 depicts an endotracheal tube 22 installed in a mouth 340 and airway 360 of a patient. The endotracheal tube 22 is retained in the airway 360 of the user using a bridle 6 system and the endotracheal tube retention system 500 shown in FIGS. 82-100. As is evident, the endotracheal tube retention system 500 includes a bite block/nesting fixture 502 that includes a bite block 504, a flange 506, a retaining portion 508 for coupling the clip to the fixture and a tubular nesting portion 510 that permits entry and retention of an endotracheal tube 22 therein. The bite block/nesting fixture 502 has a length that extends from the face/teeth 512 of a user away from the face and past the end of the nose 514. In use, a flange or an abutting plate 506 abuts a patient's lips and mouth.

The system 500 includes a bite block 504 at the front end that serves as a resting place for the teeth 512 during use of the system 500. A clip 520 extends upwardly from the nesting fixture 502 and is coupled to the nesting fixture 502 by inserting the clip 520 under several extension members or arms 516. The clip 520 is shown spaced from the nose 514, but the end of the clip 520 is elevated over the lips of the patient. A bridle 6 extends though each of the naris of the nose behind the vomer bone, with the ends of the bridle 6 extending from each naris. The ends of the bridle 6 are coupled to the top end of the clip 520 and a knot 522 maintains the bridle 6 in connection with the clip 520. As shown, the example system 500 permits the bridle 6 to be positioned above the lips of the user so that it does not cause pain or discomfort to the lips. Each of the features of the various parts of the system are discussed in detail below.

FIGS. 82-100 depict the various parts of an alternative endotracheal tube retention system 500. FIG. 82 depicts the bite block/nest 502 and clip 520 coupled to a bridle 6 as well as coupled to a neck strap 524. The neck strap 524 is optional and includes a strap 526 that couples to two sides of the clip 520 via a loop 526 that is formed on the clip 520. The strap 526 includes removable connectors or clips 528 that couple the ends of the strap 526 to the loops 526. The connectors 528 may be made of a hard plastic material, while the strap 526 may be pliable and fabric-like. The strap 526 includes a widened cushion 530 at the rear thereof that is for positioning around the rear of a patient's neck. The cushion 530 is padded and may be padded in any known manner. The cushion 530 may include loops 532 for sliding the strap 526 through in order to couple the cushion 530 to the strap 526. The strap 526 may be coupled to the cushion 530 in any known manner. The strap 526 includes a fastener 534 that permits the ends of the strap 526 to be adjustable in length. The fastener 534 may be any known type of fastener. The fastener 534 depicted is a buckle, such as a cam buckle.

FIGS. 83-88 depict the system 500 in relation to a nose 514 of a patient. The bridle 6 shown in the figures is exemplary of a bridle 6 installed behind the vomer bone of a patient (not shown) and extending out from each of the naris 536 of the nose 514. FIG. 83 depicts the bite block/nest portion 502 of the example retention system 500 coupled to the clip 520, with the clip 520 being in a closed position and a knot 522 that couples together the ends of the bridle 6 is coupled to an opening 538 defined in the top end of the clip 520 in order to retain the clip 520 on the bridle 6. FIG. 84 depicts the bridle 6 in a configuration where it would be installed behind a vomer bone such that the ends of the bridle 6 are coupled together, such as via a knot 522 or a separate connector. FIG. 85 depicts the bite block 504, flange 506, and nest 510, which are formed as an integral part. FIG. 86 depicts the clip 120 in an open, uninstalled position.

FIG. 87 depicts a view of the retention system 500, as viewed outwardly from a patient's head or sinus cavity and FIG. 88 depicts a view of the retention system 500 as viewed from the side, where the patient's lips and teeth 512 would surround the bite block 504 and the flange 506 would abut a patient's lips and face 512. In practice, the loop end 540 of the bridle 6 would be installed behind the vomer bone. The bite block 504 is shown as facing the face of a user and the user's teeth 512 can be positioned around the bite block 504. The flange 506 faces a patient's skin and lips 512 and will abut the face of a user in use. The clip 520 is shown in a closed position, and the free ends of the bridle 6 are knotted together 522 and positioned though an opening 538 formed in the top end of the arms of the clip 520, in the vicinity of where the free ends of the clip 520 couple the clip together.

FIG. 89-91 depict the bite block/nest portion 502 of the system 500. The bite block/nest 502 includes a cylindrical/tubular channel 510 that extends through the length of the bite block/nest 502. The cylindrical channel 510 is utilized for positioning, or nesting, an endotracheal tube 22 therein and has an opening extending along the length of the channel for permitting entry of the tube 22 therein. The opening 510 is positioned on a top side of the device 502. The cylindrical channel 510 has a size capable of accepting the endotracheal tube 22 in tight relation, so that the tube 22 is not occluded, but does not easily slide within the channel 510. The bite block/nest portion 502 of the system 500 is soft and flexible and is made of material such as silicone, polyurethane, block co-polymers, a thermoplastic elastomer, or other soft plastic materials. The bite block/nest portion 502 is formed as an integral part.

At a front end of the device, where the bite block 504 is positioned, the channel 510 is surrounded by a cylindrical portion that serves as the bite block 504 for a patient's teeth 512. The bite block 504 is round, with a flat top surface 542. The flat top surface 542 includes the opening 510 for receiving an endotracheal tube 22. A flange 506 is coupled to the bite block 504. The flange includes a first portion 544 that extends upwardly, a second portion 546 that extends around the sides and bottom of the bite block 504, and a third portion 548 that is coupled to the bottom of the second portion, as shown best in FIG. 87. The first portion 544 that extends upwardly is in the form of two parallel wings that have an opening 550 defined there between for receiving the endotracheal tube 22. The side and bottom front surfaces of the second portion 546 are substantially planar or nearly planar with the front surfaces of the first portion 544 of the flange 506. The various surfaces are blended together in order to provide a device with smooth outer surfaces. The third portion 548 of the flange 506 extends downwardly and is curved outwardly and downwardly in order to provide a surface that substantially matches the contours of a patient's lower lip. The lower, third portion 548 of the flange 506 abuts a patient's lower lip. The first portion 544 of the flange 506 abuts a patient's upper lip and face, and the second portion 546 may abut the top or bottom lip, or may not abut the lips at all in the case where the patient's mouth is open.

The rear portion of the device 552 is positioned adjacent the rear surface of the flange 506. The rear surface of the flange 506, at the first and second portions 544, 546 is substantially planar and the rear surface of the third portion 548 of the flange 506 has a curvature similar to the front surface of the third portion 548. A cylindrical member 554 extends rearwardly from the flange 506 and is axially aligned with the bite block 504. A pair of arms 556 is connected to the rear end of the cylindrical member 554 on either side of the slot 510 and extend towards the flange 506, but a space 560 is maintained between an inner surface of the arms 556 and the outer surface of the cylindrical member 554. This spacing 560 is provided in order to position the clip 520 under the arms 556 so that the clip 520 can be maintained on the cylindrical member 554. The arms 556 have a portion of greater width 562 at the ends adjacent the flange 506. This portion 562 helps to maintain the clip 520 on the arms 556 once the clip 520 is slid past the portion of greater width 562. The clip 520 includes loops 526 that are positioned on the sides of the clip 520 and the loops 526 have a dimension so that they are pressed over the soft material of the arms 556. The arms 556 have a portion 566 at the rear end thereof that is enlarged and helps to maintain the loops 526 of the clip 520 on the arms 556. The cylindrical portion 554 also has the portion 566 of greater diameter at the rear end of the cylindrical portion 554 in order to assist in maintaining the clip 520 on the cylindrical portion 554.

FIGS. 92-94 depict the clip 520 of the system. The clip 520 is formed of two halves 520a, 520b that are coupled together via a living hinge 48. The two halves 520a, 520b serve as arms that move towards one another. At a bottom end of the clip, an inner cylindrical opening 570 is formed that is positioned around the cylindrical portion of the nest 554. Mating connectors 572, 574 are formed on the inner surfaces of the arms 520a, 520b in order to connect the two arms together. A first mating connector 572 is positioned directly adjacent the cylindrical opening 570. A second mating connector 574 is positioned at the top end of the arms 520a, 520b. The mating connectors 572, 574 are hooks that mate together. A central part 576 of each arm is planar in order to permit the arms to extend upwardly from the nest 554. Loops 526 extend outwardly from the bottom of each arm 520a, 520b adjacent the cylindrical opening 570. These loops 526 mate with the arms 556 of the nest portion. As shown in FIG. 94, the arms 520a, 520b may have a first perpendicular portion 578 that mates with the nest 554 so that it extends perpendicularly relative to the axis of the nest, a second angled portion 580 that extends at an angle relative to the first perpendicular portion 578, and a third perpendicular portion 582 that is coupled to the second angled portion 580 and that is parallel to the first perpendicular portion 578, as shown best in FIG. 94. The angled second portion 580 permits the top end of the arms 520a, 520b to either be positioned closer or farther away from the nose 514 during use, depending upon the orientation of the arms. If the second portion 580 is positioned such that it angles away from the flange 506, then the third portion 582 will be farther away from the nose 514.

The upper connector 574b of one of the arms of the clip includes an opening 538 for receiving an end 522 of the bridle 6 in order to hold the bridle 6 in position within the arms 520a, 520b. The opening 538 accepts a narrow portion of the bridle 6 and holds a knotted or enlarged portion 522 of the bridle 6 when closed. The upper end of the arm that includes the opening 538 is coupled to the remainder of the arm via a living hinge 48 so that the connector 574b can bend relative to the remainder of the arm 520b. The upper end of the other arm 520a has a connector 574a that is fixed relative to the arm and does not bend significantly. The bending upper connector 574b permits the lower connector 572 of the arms 520a, 520b to couple together first once the cylindrical opening 570 is positioned around the nest 554. Then after the bridle knot or enlarged end portion (not shown) is prepared, the knot can be slid into the opening 538 formed in the upper connector 574b and the upper connector 574b can be clipped into the fixed connector 574a in order to couple the end of the bridle 6 to the upper end of the clip 520.

FIGS. 95-100 depict how the clip 520 is coupled to the cylindrical portion of the nest 554. In particular, the clip 520 is positioned over the arms 556 of the cylindrical portion 554 and the arms 556 are bent outwardly and inserted into the loops 526 on the clip 520. The enlarged portions 566 at the ends of the arms 556 on the cylindrical portion 554 are slid into the loops 526. The widened portion on the arms 562 is press fit through the loops 526 until the loops 526 extend past the widened portion 562 and abuts the enlarged diameter portion 566 at the rear of the nest 554. Then the arms 520a, 520b of the clip 520 are moved toward one another until the connectors 572, 574 clip together.

FIG. 100 shows how the various parts of the clip interact with the nest 554 and with other parts of the clip 520. To the extent that interferences are shown, this is meant to show how the parts press fit together. The parts will not overlap one another in the manner shown in reality. Instead, the parts will press against each other in the areas of interference.

FIGS. 101-108 depict an alternative bite block/nest 600. The bite block/nest 600 shown includes a centrally located, longitudinally extending, cylindrical opening 602 that serves as the nest for endotracheal tube 22. The cylindrical opening 602 has an inner diameter that permits the endotracheal tube 22 to be held within the opening 602. Alternatively, the cylindrical opening 602 could have an inner diameter that permits the endotracheal tube 22 to float within the opening 602. A slot 604 extends along the length of the upper part of the cylindrical opening 602 for receiving the endotracheal tube 22 into the cylindrical opening 602.

A bite block 606 is positioned at one end of the bite block/nest 600 and a cylindrical member 608 is positioned at the other end of the bite block/nest 600 for receiving a clip 520. A flange 610 separates the bite block 606 from the cylindrical member 608. The flange 610 is substantially planar and has a larger lateral dimension than the bite block 606 and the cylindrical member 608. The flange 610 has a substantially oval shape or egg shape, with part of the oval extending around all sides of the bite block 606 and nest 602. The upper part of the flange 610 has a slot 604 therethrough that aligns with the slot 604 that is positioned along the length of the bite block/nest 600 for receiving the endotracheal tube 22. The flange 610 has a substantially even thickness. The rear portion 608 of the nest 602 includes the cylindrical member 608 for receiving the clip 520. As with FIGS. 89-91, the cylindrical member includes arms 612 that extend from a rear end towards the flange 610. The arms 612 are coupled to the cylindrical member 608 at the rear end and are spaced from the cylindrical member 608 along their length, but remain substantially parallel to the cylindrical member 608. The arms 612 accept the loops 526 that are formed on the clip 520, shown in prior embodiments.

FIGS. 109-120 depict another alternative embodiment 700 that is similar to the embodiment 500 shown in FIGS. 82-100, but includes some additional features. As with the embodiment 500 shown in FIGS. 82-100, the device may optionally include a neck strap 702 that has a cushion 704. The neck strap may include a buckle 706, such as a cam buckle, that permits the neck strap 702 to be easily adjusted in length. Other types of buckles 706 may alternatively be used. The cushion 704 is not absolutely necessary and the strap 702 could be used without it, although the cushion 704 is designed to provide additional comfort to the user. The ends of the strap 702 include clips 708 for coupling with the loops 726 on the clip 710. The clips 708 may be removed from the loops 726 in order to remove the strap from the system 700. Any known type of clips 708 can be used to couple the strap 702 to the loops 726. However, it is preferred that the clips 708 on the strap have a thinner dimension in order to permit them to be coupled easily to the loops 726 on the clip 710.

The bite block/nest portion 740 of the embodiment 700 shown in FIGS. 109-120 are similar to that shown in FIGS. 82-100, although the bite block 742 is shown as being slightly longer than that shown in FIGS. 82-100. As with the embodiment shown in FIGS. 82-100, the bite block 742 has a flattened upper surface 744 that permits the front teeth to easily rest against the upper surface 744 of the bite block 742.

The rear portion 746 of the bite block/nest portion 740 is significantly longer in length that the example shown in FIGS. 82-100 and includes similar arms 748 to that of FIGS. 82-100. The longer length permits the clip 710 to be positioned either closer to the flange 712 or farther away from the flange 712. Depending upon the shape of the face and nose of the patient, the longer cylindrical member 746 permits greater flexibility in positioning of the clip 710 relative to the nose so that interference between the top part 714 of the clip 710 and the nose is deterred. It is desirable to avoid contact between the nose and the top part 714 of the clip 710 during use. The upper end 714 of the clip includes rounded top corners 716 so that when the upper part of the clip 710 is coupled together, the rounded top corners 716 provide a smoother surface. In the event of contact between the top of the clip 714 and the face of a patient, the smooth, rounded 716 surfaces provide a greater comfort to a patient.

The clip of FIGS. 109-120 is similar to the design shown in FIGS. 82-100, but includes two positions or openings 720 for anchoring an end of the bridle 6 to the clip 710, including an upper position 720a and a lower position 720b. The upper position 720a is at the top end of the clip 710 and the lower position 720b is at a more central height location of the clip 710. A living hinge 48 is associated with one of the arms of the clip 710 directly below the lower position 720b. Once the loops 726 on the clip 710 are fitted over the arms 748 on the cylindrical portion 746 of the nest, the cylindrical opening 722 is closed using the lower connector 724. Then, once the bridle knot 728 is prepared, the knot 728 can be positioned in either the upper position 720a or the lower position 720b and the arm that includes the living hinge 48 can be moved toward the other arm until the connectors 720, 720a couple together. This design permits the bridle 6 to be positioned at different height positions relative to the clip 710, which provides greater flexibility depending upon the anatomy of a patient's face and the size of the patient. The clinician is given some variability in the angle that the bridle 6 leaves the patient's nose by raising and lowering the attachment point for the bridle, which helps to prevent or at least deter ulceration. This variability is desirable in order to accommodate faces and noses of different shapes and sizes.

As previously explained, the cylindrical portion 746 of the design of FIGS. 109-120 is longer in order to permit greater variability of placement of the clip 710 relative to a patient's nose. This permits the angle that the bridle 6 leaves the patient's nose to be adjusted. The flange 712 of this design is similar to the flange 712 shown in FIGS. 82-100 and includes a curved third portion 730 that may rest against a patient's lower lip.

The entire design is metal free so that the device can be MRI safe.

In one method according to the invention, a method for retaining or suspending an endotracheal tube 22 includes first installing an endotracheal tube 22 in an airway of a patient 24. Then a strap 68 or cable tie 34 is positioned around the exterior of the endotracheal tube 22 at a position that is slightly beyond the lips 100 of the patient 24. The strap 68 or cable tie 34 is tightened around the endotracheal tube 22 so that it is substantially immovable. The cable tie 34 or strap 68 is preferably soft to the touch and does not have any sharp surfaces. The strap 68 is held against the endotracheal tube 22 by friction. The position of the strap 68 advantageously can visually mark the current depth of the endotracheal tube 22 placement for the healthcare professionals.

As described above, in one embodiment, the internal diameter D1 of the closed "floating" clip 30, 90 is slightly larger than the outside diameter D2 of the endotracheal tube 22. This allows the system to be utilized with different endotracheal tubes 22 of various diameters. The "floating" clip 30, 90 is placed around the portion of the endotracheal tube 22 away from the patient 24, but against the locked cable tie 34 or strap 68.

There may be two connection portions 36, 44, in the form of loops, coupled to an exterior surface of the clip 30, 90 or a connection area 98 at the top of the clip 30, 90 where the first and second parts 38, 40 of the clip 30, 90 meet. One of these connection portions may be used with the nasal bridle 6 and umbilical tape 6. The ends of the umbilical tape 6 are tied through the connection portion 36/98 in order to connect the floating clip 30, 90 to the vomer bone, which serves as an anchor for the clip 30, 90. When the endotracheal tube 22 is pulled upon by the patient 24, the bulk of the cable tie 34 or strap 68 makes it impossible for the floating clip 30, 90 to advance beyond the cable tie 34 or strap 68, and the "floating" clip 30, 90 remains in place because it is anchored to the vomer bone. This tension created on the umbilical tape 6 will result in a pain sensation for the patient 24, who will immediately cease pulling or tugging on the endotracheal tube 22.

A second connector on the floating clip 30, 90, or loop, may or may not be used. If there is a likelihood of aggression on the part of the patient 24 a cushioned neck strap can be implemented and tied to the clip 30, 90 through this optional second loop. If the endotracheal tube 22 needs to be adjusted or replaced, the "floating" clip 30, 90 can be easily opened by a healthcare professional, leaving the umbilical tape 6 and neck strap (if applicable) in place on the patient 24. After the new tube 22 is positioned, a new cable tie 34 or strap 68 can be tightened around the tube 22, and the clip 30, 90 can be closed once again to complete the retention system 20.

In another embodiment of the method, a non-floating clip 120 can be utilized. In this example, a compressible tubular member 122 is installed around the endotracheal tube 22 in the vicinity of the mouth 18 of the patient 24. Then the clip 120 is closed around the tubular member 122 in order to substantially fix the location of the tubular member 122 and clip 120 on the endotracheal tube 22. In this example, the internal diameter D1 of the closed clip 120 is slightly smaller than the outside diameter D2 of the compressible tubular member 122 such that the force applied by the clip 120 on the compressible tubular member 122 compresses the tubular member 122 onto the endotracheal tube 22. Different sized tubular members 122 and clips 30, 90, 120 may be designed based upon the size of the endotracheal tube 22, if desired.

There may be two connection portions 36/98, 44, in the form of loops or recesses formed on the clip 30, 90, 120 for coupling with the nasal bridle 6 and with the neck strap 58. Alternatively, a single connector can be used for coupling to both the bridle 6 and the neck strap 58. The ends of the nasal bridle 6 are tied together through the connection portion 36/98 so that the umbilical tape 6 is raised above a patient's face during use.

In a third example system, a compressible tubular member that has a bumper 130 installed on one end thereof is used instead of a constant outer diameter tubular member 122. In this example, the clip 120 is positioned around the smaller diameter portion 122 of the tubular member and the enlarged diameter portion 130 is used as a mouth guard or bumper 130 against the patient's face.

While the methods described above involve installing the endotracheal tube 22 before the bridle 2, 6 is installed in the nasal cavity, the nasal bridle 2, 6 could alternatively be installed first, if desired. In each of the above-described devices, the optional neckband 58, shown in FIG. 12, may be utilized.

According to another method, an endotracheal tube 22 is first inserted into an airway of a patient. Then an end of the endotracheal tube 22 that extends from a patient's mouth is coupled to a nest that includes an elongated cylindrical opening for receiving the endotracheal tube 22 in either a fitted or floating position within the nest. The nest includes a clip that is positioned around the nest and that is movable along the length of the nest. The opposite end of the nest includes a bite block for positioning inside a mouth of a patient. A flange is positioned between the bite block and the other end of the nest and abuts at least part of a patient's face of mouth. A bridle 6 is installed in a patient's nose so that it extends around the vomer bone inside the nasal cavity and the ends of the bridle 6 extend out from each naris of a patient. A knot can be formed in the ends of the bridle 6 in order to couple the ends of the bridle 6 together. Alternatively, a coupling device may be used to couple together the ends of the bridle 6.

Once the knotted end of the bridle 6 is formed, it may be coupled to the clip by positioning the bridle 6 ends through an opening formed in the clip. Then the clip can be closed around the knot of the bridle 6 so that the knot is positioned on a side of the clip that is opposite the side of the clip that faces a patient's face. Depending upon the length of the nest, the clip may be moved toward and away from the face adjacent the flange in order to provide proper orientation for the bridle 6 as it exits the nose of the patient.

A floating clip 30, 90 for holding a tube 22 that is inserted into a facial orifice of a patient 24 includes a first part 38 having a curved shape, a second part 40 having a curved shape, a coupling portion 48 positioned between the first part 38 and the second part 40 to couple first ends of the first and second parts 38, 40 together, and a fastening portion 50, 52 between the first and second parts 38, 40 to removably couple the second ends of the first and second parts 38, 40 together. The first and parts 38, 40 have an internal space D1 that is greater than the diameter D2 of a tube 22 in order to allow the clip 30, 90 to float relative to the tube 22.

The floating clip 30, 90 may further comprise a first connector 36/98 coupled to one or both of the first part 38 and the second part 40 for coupling with a support member 2, 6. The first connector 36 may be positioned on an outer surface of the first part 38 such that when the clip 30, 90 is coupled to a support member 6, the first connector 36 is positioned on a top surface of the first part 38 when a patient 24 is in a supine position.

The floating clip 30, 90 may further comprise a member 34, 68 positioned around the tube 22 in a substantially immovable manner. The member 34, 68 may have an external dimension D3 that is smaller than an inner dimension D1 of the first and second clip parts 38, 40. The first and second clip parts 38, 40 may be movable longitudinally and rotationally relative to the tube 22 when not coupled to the member 34, 68 and movable in one longitudinal direction when coupled to the member 34, 68. Alternatively, the clip 30, 90 may be movable longitudinally and rotationally relative to the tube 22 when not coupled to the member 34, 68 and movable in one longitudinal direction and rotationally when coupled to the member 34, 68.

At least one of the first and second clip parts 38, 40 may have an interior shape that serves as a stop so that the first and second clip parts 38, 40 cannot move past the member longitudinally on the tube 22. At least one of the first and second clip parts 38, 40 may have an extension 110 extending longitudinally at the second end thereof, said extension 110 assisting in preventing rotation of the clip 30, 90 when the first and second parts 38, 40 are positioned around the endotracheal tube 22. The first connector 36/98 may be positioned in the vicinity between the first and second clip parts 38, 40.

In an alternative example, a clip system 20 for holding a tube 22 that is inserted into a facial orifice of a patient 24 includes a first clip part 38 having a contoured inner shape 126, a second clip part 40 having a contoured inner shape 128, a coupling portion 48, a fastening portion 50, 52, a connecting portion 36/98, 44, and a tubular member 34, 68, 122. The coupling portion 48 is positioned between the first clip part 38 and the second clip part 40 to couple together first ends of the first and second clip parts 38, 40. The fastening portion 50, 52 is associated with second ends of the first and second clip parts 38, 40 for mating the second ends together around a tube 22. The connecting portion 36/98, 44 is coupled to at least one or both of the first and second clip parts 38, 40 for coupling a support member 2, 6 to a tube 22. The tubular member 34, 68, 122 is positioned at least in part around the tube 22 and coupled to the tube 22 in a non-movable manner, with the first and second clip parts 38, 40 at least partially surrounding the tubular member 34, 68, 122.

The first and second clip parts 38, 40 may have an inner shape that is larger than the tubular member 34, 68 such that the first and second clip parts 38, 40 are movable away from the tubular member 34, 68 when installed on the tube 22. Alternatively, the first and second clip parts 38, 40 may have an inner shape that is smaller than the tubular member 122 such that the first and second clip parts 38, 40 clamp down upon the tubular member 122 so that both the tubular member 122 and the first and second clip parts 38, 40 are immovable on the tube 22.

The connecting portion 36/98, 44 may be positioned on the clip parts 38, 40 such that it is elevated above the tube 22 in order to position the support member 2, 6 in spaced relation above the tube 22 when a patient 24 is in a supine position. The tubular member 122 may be substantially cylindrical and may have a first end and a second end. Alternatively, the tubular member 68 may be a removable strap 68 that is positioned around the tube 22 in a substantially immovable manner. Alternatively, the tubular member 34 may be a zip tie 34 that is clamped around the tube 22 in a substantially immovable manner.

The tubular member 130 at the first end thereof may have a first outer diameter D4 portion. A second outer diameter portion D5 that is smaller than the first outer diameter portion D4 may be positioned at the second end of the tubular member 122. The first and second clip parts 38, 40 may be positioned around the second smaller diameter portion D5 at the second end, with the first diameter portion D4 at the first end serving as a bumper 130 to a patient's face. The first and second clip parts 38, 40 have an external shape such that the connecting portion 36/98, 44 is spaced from the tube 22.

An example system 20 for suspending a tube 22 that is inserted into a facial orifice of a patient 24 includes a holder 30, 90, 120 and a flexible member 2, 6 coupled to the holder. The holder 30, 90, 120 is for coupling with a tube 22 that is inserted into a facial orifice of a patient 24. The flexible member 2, 6 is coupled to the holder 30, 90, 120 and coupled around a body part of a patient 24. The flexible member 2, 6 has an installed length that is shorter than a distance measured from ear to ear across the face of a patient 24.

In one example, the facial orifice is a mouth 18 and the flexible member 2, 6 is positioned around the vomer bone of a patient's nasal cavity. The flexible member may be one or both of an umbilical tape 6 and a flexible polymeric strap 2. The holder 30, 90 may include a first part 34, 68 that is substantially fixed positionally on the tube 22 and a second part 30, 90 that is movable on the tube 22 and relative to the fixed part 34, 68. Alternatively, the holder 120 may include a first part 122 that is substantially fixed positionally on the tube 22 and a second part 120 that is fixed positionally on the tube 22 and clamped around the first fixed part 122. Alternatively, the holder 30, 90 may include a part that is movable longitudinally and rotationally on the tube 22.

The first fixed part 34, 68, 122 may be removable from the tube 22 when the second part 30, 90, 120 is not installed around the first fixed part. The first fixed part may be a resilient, compressible member 122 and the second fixed part 120 may compress the first fixed part 122 when installed thereon. The first fixed part of the holder may comprise a first portion 130 at one end and a second portion 122 at a second end, with the first portion 130 having a first outer diameter D4 and the second portion 122 having a second outer diameter D5. The second outer diameter D5 may be smaller than the first outer diameter D4, and the holder 120 is clamped around the second portion 122 of the first fixed part.

Another example system for suspending a tube 22 that is inserted into the mouth 18 of a patient 24 includes a holder 30, 90, 120 for holding a tube 22 that is inserted into the mouth 18 of a patient 24 and a flexible member 6 coupled to the holder that 30, 90, 120 extends substantially upwardly toward the nose 10 of the patient 24. The flexible member 2, 6 is provided for extending around a body part of a patient 24 in order to suspend the holder 30, 90, 120 in position below a patient's nose 10. The flexible member 2, 6 may be suspended by the holder 30, 90, 120 so that it does not normally touch the lips 100 of a patient 24. The holder 30, 90, 120 may have an elongated shape and a connecting portion 36/98 may be coupled to the holder 30, 90, 120 for coupling with the flexible member 2, 6. The elongated shape may allow the connecting portion 36/98 of the holder 30, 60, 120 to be spaced from the tube 22. The flexible member 2, 6 may be one or both of a tape portion 6 and a flexible polymeric elongated member 2.

In another example, a system for suspending a tube 22 that is inserted into the mouth 18 of a patient 24 includes a holder 30, 90, 120 for coupling to a tube 22 that is positioned in a patient's mouth 18, and a flexible support member 2, 6 positioned around a patient's vomer bone and having two ends. Each end of the flexible support member 2, 6 extends out of a patient's nares 8, 16 and the ends are coupled to the holder 30, 90, 120. The holder 30, 90, 120 may be one of fixed or movable relative to the tube 22.

The holder 30, 90, 120 may have an exterior connector 36/98, 44 coupled thereto. The system may also include a bridle installing system comprising a flexible member 2 and a retrieving member 14, with magnets 4 positioned at the ends of both the flexible member 2 and the retrieving member 14. The flexible member 2, 6 is pulled through the nasal cavity of a patient 24 in order to install the flexible member 2, 6 behind the vomer bone of a patient 24. After the flexible member 2, 6 is installed behind the vomer bone of a patient 24, a first end of the flexible member 2, 6 extends from a first naris 8 of a patient 24 and a second end of the flexible member 2, 6 extends from a second naris 16 of a patient 24. Both ends are coupled to the connector 36/98, 44 on the holder 30, 90, 120 to hold a tube 22 that is inserted into a facial orifice of a patient 24.

The holder 30, 90 may be a clamp that surrounds the tube 22 and is movable longitudinally and rotationally relative to the tube 22. The system may further include a fixed member 34, 68 positioned around the tube 22 for mating with the holder 30, 90 in order to deter longitudinal movement of the holder 30, 90, 120 toward a patient's face. The fixed member 34, 68 may further deter rotational movement of the holder 30, 90 when the holder 30, 90 is positioned at least in part around the fixed member 34, 68.

The fixed member 122 may be a resilient compressible member 122 and the holder 120 may clamp and compress the fixed member 122 around the tube 22 in order to deter movement of the fixed member 122 and the holder 30, 90, 120 toward the mouth 18 of the patient 24. The fixed member 122 may have an enlarged diameter portion 130 that is positioned adjacent to the mouth 18 of the patient that serves as a bumper 130 or mouth guard.

A method for suspending a tube 22 that is inserted into the mouth 18 of a patient 24 above a patient's skin includes the steps of installing an endotracheal tube 22 into the airway of a patient 24 and installing a nasal bridle 2, 6 in the nasal cavity of a patient 24 so that one end of a flexible member 2,6 extends from a first naris 8 of a patient's nose 10, a portion of the flexible member 2, 6 is wrapped around the patient's vomer bone, and the other end of the flexible member 2, 6 extends from a second naris 16 of a patient's nose 10. The method also includes positioning a member 34, 68, 122 around the endotracheal tube 22 in the vicinity of a patient's mouth 18 and installing a clip 30, 90, 120 over the member. The clip 120 is one of clamped over the member 122 so that the member and the clip are substantially immovable, or the member 34, 68 is substantially immovable and the clip 30, 90 is movable on the tube 22 and relative to the member.

While the first and second parts 38, 40 of the clip were described as having a curved inner contour, other shapes could also be utilized. For example, the inner contour could be rectangular or not rounded. The inner contour could be convex or concave. The inner contour could vary and have different shapes. The first part 38 of the clip could have a rounded or curved contour while the second part 40 of the clip could have a different shape, such as a flat shape. The invention is not limited to the shape of the contour of the clip unless claimed.

Another example retention system for use with a bridle 6 installed in a nose of a patient includes a member coupled to a medical device and a connector for coupling to a bridle 6 that is installed in a nose of a patient. The member is suspended from a nose of a patient and the medical device extends into the mouth of a patient or is suspended adjacent the face of a patient.

The medical device may be an endotracheal tube 22 that is installed in an airway of a patient and the connector may be coupled to the endotracheal tube 22. The member may include a first part that extends around the endotracheal tube 22, and a second part that is clipped to the first part. The second part includes a portion for coupling to the bridle 6. The second part may extend upwardly from the endotracheal tube 22 towards a patient's nose. The first part of the member may include a bite block for positioning in a patient's mouth, a flange coupled to the bite block for positioning against a patient's face, and a cylindrical member positioned on the opposite side of the flange for coupling with the second part.

Another example endotracheal tube retention system includes a longitudinal member for receiving an endotracheal tube 22 therein, a clip, and a bridle 6. The clip is for positioning around an outer portion of the longitudinal member and has at least one coupling mechanism for closing the clip around the longitudinal member. The bridle 6 is for coupling to the clip and for suspending the bridle 6 above the lip and below the nose of a patient.

The longitudinal member may have a substantially cylindrical internal channel for receiving the endotracheal tube 22 therein and may include a slot extending along the length thereof for receiving an endotracheal tube 22 therein. The longitudinal member may have an inner diameter for grasping the endotracheal tube 22.

The clip may have a first arm and a second arm that are coupled together by a living hinge. The first and second arms may each include an inner portion positioned adjacent the living hinge that defines a circular opening for seating around the longitudinal member, a connector for coupling the first and second arms together in a closed position, and an opening for coupling with an end of the bridle 6. The opening may be spaced from the living hinge.

The clip may have a first opening for coupling with an end of the bridle 6 and a second opening for coupling with an end of the bridle 6, with the first and second openings being spaced from one another so that the first opening is positioned at an upper end of the clip and the second opening is positioned towards a more centrally disposed location on the clip. The first and second openings permit the bridle 6 to be coupled to the clip at different heights.

The longitudinal member may include a substantially centrally located flange that is substantially perpendicular to a longitudinal axis of the longitudinal member. The flange may have a first upper part that extends upwardly from the longitudinal member and may include a slot that is aligned with the slot of the longitudinal member. The flange may include a second part that extends outwardly from the sides and bottom of the longitudinal member, with the flange being substantially planar and for abutting a patient's face and/or lips.

The flange may further include a curved portion extending from the second portion and having a contour for mating with a lower lip of a patient. The user's mouth may be accessible when the endotracheal tube retention system is installed in a patient's mouth. The longitudinal axis of the clip may be positioned substantially parallel to the first and second parts of the flange when the clip is installed around the longitudinal member. The clip may be positionable at different positions along the length of the longitudinal member.

The longitudinal member may include arms that extend from one end toward a central location of the longitudinal member, with part of the clip fitting under the arms and part of the clip fitting over the arms. The clip may include outwardly extending loops that are positioned on opposite sides of the clip and the loops fit over the arms.

The clip may include a first arm and a second arm that are coupled together via a living hinge, with a cylindrical opening provided between the first and second arms in the vicinity of the living hinge for surrounding the longitudinal member. A first connector may includes a first part that is coupled to the first arm and a second part that is coupled to the second arm opposite the living hinge adjacent the cylindrical opening for closing the clip around the longitudinal member. The first part of the first connector may be a hook and the second part of the first connector may be a hook and the first and second parts of the first connector connect together.

The first and second arms of the clip may include at least one second connector for coupling the first and second arms together at a position that is spaced from the first connector. The second connector may include a recess for receiving the bridle 6. Either the first or the second arms may include a portion with a living hinge that permits the second connectors to rotate towards one another once the bridle 6 is positioned in the recess.

While the above-description was generally in the context of endotracheal tube 22 retention, as mentioned above, other types of devices may also derive a benefit from the technology, including those relating to feeding tubes, or other tubes that may be positioned in the mouth 18, nose 10, or positioned on the face or neck, or in the vicinity of the face. Thus, the examples described and claimed herein are not limited to use solely with an endotracheal tube 22.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What is claimed is:

1. An endotracheal tube retention system comprising:
   a longitudinal member for receiving an endotracheal tube therein;
   a clip for positioning around an outer portion of the longitudinal member and having at least one coupling mechanism for closing the clip around the longitudinal member; and
   a nasal bridle for coupling to the clip;
   wherein the endotracheal tube retention system is configured for suspending the bridle above the lip and below the nose of a patient, and
   further wherein the clip includes a first arm and a second arm that are coupled together via a living hinge, with a cylindrical opening provided between the first and second arms in the vicinity of the living hinge for surrounding the longitudinal member, with a first connector that includes a first part that is coupled to the first arm and a second part that is coupled to the second arm opposite the living hinge adjacent the cylindrical opening for closing the clip around the longitudinal member.

2. The system of claim 1, wherein the longitudinal member has a cylindrical internal channel for receiving the endotracheal tube therein and includes a slot extending along the length thereof for receiving an endotracheal tube therethrough, with the longitudinal member having an inner diameter for grasping the endotracheal tube.

3. The system of claim 2, wherein the longitudinal member includes a centrally located flange that is perpendicular to a longitudinal axis of the longitudinal member, with the flange having a first upper part that extends upwardly from the longitudinal member and includes a slot that is aligned with the slot of the longitudinal member, and a second part that extends outwardly from the sides and bottom of the longitudinal member, wherein the flange is planar.

4. The system of claim 3, wherein the flange further comprises a curved portion extending from the second portion and having a contour configured for mating with a lower lip of a patient.

5. The system of claim 3, wherein a longitudinal axis of the clip is positioned parallel to the first and second parts of the flange when the clip is installed around the longitudinal member.

6. The system of claim 5, wherein the clip is positionable at different positions along the length of the longitudinal member.

7. The system of claim 1, wherein the clip further includes an opening for coupling with an end of the bridle, with the opening for coupling with the end of the bridle being spaced from the living hinge.

8. The system of claim 1, wherein the clip has a first opening for coupling with an end of the bridle and a second opening for coupling with an end of the bridle, with the first and second openings being spaced from one another so that the first opening is positioned at an upper end of the clip and the second opening is positioned towards a centrally disposed location on the clip, with the first and second openings permitting the bridle to be coupled to the clip at different heights.

9. The system of claim 1, wherein the endotracheal tube retention system is configured so that the mouth of a patient is accessible when the endotracheal tube retention system is installed in the mouth of the patient.

10. The system of claim 1, wherein the longitudinal member includes arms that extend from one end thereof towards a central location of the longitudinal member, with part of the clip fitting under the arms and part of the clip fitting over the arms.

11. The system of claim 10, wherein the clip includes outwardly extending loops that are positioned on opposite sides of the clip and the arms fit into the loops.

12. The system of claim 1, wherein the first part of the first connector is a hook and the second part of the first connector is a hook and the first and second parts of the first connector connect together.

13. The system of claim 1, wherein the first and second arms of the clip include at least one second connector for coupling the first and second arms together at a position that is spaced from the first connector, with a part of the second connector being positioned on the first arm and a part of the second connector being positioned on the second arm, with the part of the second connector on one of the arms including a recess for receiving the bridle and a portion with a living hinge that is positioned in the vicinity of the part of the second connector on the one of the arms that permits the part of the second connector on the one of the arms to rotate towards the part of the second connector on the other arm once the bridle is positioned in the recess.

14. A method of use of the endotracheal tube retention system of claim 1, the method comprising steps of:
   (1) installing an endotracheal tube into an airway of a patient;
   (2) installing the nasal bridle in in a nasal cavity of the patient such that a first end of the nasal bridle extends from a first naris of a nose of the patient, a portion of the nasal bridle is wrapped around a vomer bone of the patient, and a second end of the nasal bridle extends from a second naris of the nose of the patient;
   (3) positioning the longitudinal member around the endotracheal tube;
   (4) installing the clip over the longitudinal member; and
   (5) coupling the nasal bridle to the clip.

15. The method of claim 14, wherein the longitudinal member has a cylindrical internal channel for receiving the endotracheal tube therein and includes a slot extending along the length thereof for receiving an endotracheal tube therethrough, with the longitudinal member having an inner diameter for grasping the endotracheal tube.

16. The method of claim 14, wherein the clip further includes an opening for coupling with an end of the bridle, with the opening for coupling with the end of the bridle being spaced from the living hinge.

17. The method of claim 14, wherein the clip has a first opening for coupling with an end of the bridle and a second opening for coupling with an end of the bridle, with the first and second openings being spaced from one another so that the first opening is positioned at an upper end of the clip and the second opening is positioned towards a centrally disposed location on the clip, with the first and second openings permitting the bridle to be coupled to the clip at different heights.

18. The method of claim 14, wherein the first part of the first connector is a hook and the second part of the first connector is a hook and the first and second parts of the first connector connect together.

19. The method of claim 14, wherein step (1) is carried out before step (2).

20. The method of claim 14, wherein step (2) is carried out before step (1).

* * * * *